United States Patent
Wang et al.

(10) Patent No.: US 12,312,585 B2
(45) Date of Patent: May 27, 2025

(54) OLIGONUCLEOTIDES TARGETING FRATAXIN AND RELATED METHODS

(71) Applicant: UNIVERSITY OF MASSACHUSETTS, Boston, MA (US)

(72) Inventors: Feng Wang, Worcester, MA (US); Jonathan Watts, Worcester, MA (US)

(73) Assignee: UNIVERSITY OF MASSACHUSETTS, Westborough, MA (US)

(*) Notice: Subject to any disclaimer, the term of this patent is extended or adjusted under 35 U.S.C. 154(b) by 85 days.

(21) Appl. No.: 17/175,156

(22) Filed: Feb. 12, 2021

(65) Prior Publication Data

US 2021/0285002 A1 Sep. 16, 2021

Related U.S. Application Data

(60) Provisional application No. 62/976,647, filed on Feb. 14, 2020.

(51) Int. Cl.
C12N 15/11 (2006.01)
C12N 15/113 (2010.01)

(52) U.S. Cl.
CPC ...... *C12N 15/1135* (2013.01); *C12N 2310/11* (2013.01); *C12N 2310/313* (2013.01); *C12N 2310/3145* (2013.01); *C12N 2310/321* (2013.01); *C12N 2310/322* (2013.01); *C12N 2310/3231* (2013.01); *C12N 2310/3233* (2013.01); *C12N 2310/3341* (2013.01); *C12N 2310/346* (2013.01); *C12N 2310/3513* (2013.01); *C12N 2320/30* (2013.01); *C12N 2330/30* (2013.01)

(58) Field of Classification Search
CPC ........ C12N 2310/11; C12N 2310/3231; C12N 2310/3341
See application file for complete search history.

(56) References Cited

U.S. PATENT DOCUMENTS

| | | |
|---|---|---|
| 4,522,811 A | 6/1985 | Eppstein et al. |
| 5,684,143 A | 11/1997 | Gryaznov et al. |
| 5,858,988 A | 1/1999 | Wang |
| 6,168,587 B1 | 1/2001 | Bellhouse et al. |
| 6,194,389 B1 | 2/2001 | Johnston et al. |
| 6,291,438 B1 | 9/2001 | Wang |
| 6,471,996 B1 | 10/2002 | Sokoll et al. |
| 6,472,375 B1 | 10/2002 | Hoon et al. |
| 7,399,845 B2 | 7/2008 | Seth et al. |
| 7,427,672 B2 | 9/2008 | Imanishi et al. |
| 2004/0171570 A1 | 9/2004 | Allerson et al. |
| 2005/0130923 A1 | 6/2005 | Bhat et al. |
| 2017/0145414 A1 | 5/2017 | Collard et al. |
| 2019/0160186 A1 | 5/2019 | Lundberg et al. |

FOREIGN PATENT DOCUMENTS

| | | | |
|---|---|---|---|
| WO | WO 1999/014226 A2 | 3/1999 | |
| WO | WO 2003/004602 A3 | 11/2004 | |
| WO | WO 2007/134181 A2 | 11/2007 | |
| WO | WO 2008/101157 A1 | 8/2008 | |
| WO | WO 2008/150729 A2 | 12/2008 | |
| WO | WO 2008/154401 A2 | 12/2008 | |
| WO | WO 2009/006478 A2 | 1/2009 | |
| WO | WO 2012/170771 A1 | 12/2012 | |
| WO | WO-2015023939 A1 * | 2/2015 | ............. A61P 21/00 |
| WO | WO 2017/030973 A1 | 2/2017 | |
| WO | WO 2017/186815 A1 | 11/2017 | |
| WO | WO-2018002783 A1 * | 1/2018 | ............... C12N 9/22 |
| WO | WO 2018/031933 A2 | 2/2018 | |
| WO | WO 2018/098587 A1 | 6/2018 | |
| WO | WO 2019/126641 A2 | 6/2019 | |
| WO | WO-2019140452 A1 * | 7/2019 | ......... A61K 31/7088 |
| WO | WO 2021/163564 A1 | 8/2021 | |

OTHER PUBLICATIONS

Biscans, et al., Diverse Lipid Conjugates for Functional Extra-Hepatic siRNA Delivery in Vivo, Nucleic Acids Research, vol. 47, No. 3, pp. 1082-1096, Dec. 14, 2018.

Clark, et al., Role of Frataxin Protein Deficiency and Metabolic Dysfunction in Friedreich Ataxia, an Autosomal Recessive Mitochondrial Disease, Neuronal Signal, vol. 2, No. 4, pp. 1-11, Nov. 2, 2018.

Crooke, et al., Antisense technology: A review, Antisense Research and Applications, CRC Press, Boca, Raton, pp. 276-278, 1993.

Doğan-Aslan, et al., Demographic and Clinical Features and Rehabilitation Outcomes of Patients With Friedreich Ataxia: a Retrospective Study, Turkish Journal of Physical Medicine and Rehabilitation, vol. 64, No. 3, pp. 230-238, Sep. 2018.

Eckstein, Phosphorothioate Oligodeoxynucleotides: What Is Their Origin and What Is Unique About Them?, Antisense and Nucleic Acid Drug Development, vol. 10, Issue 2, pp. 117-121, 2000.

Golberg, et al., Engineering a Targeted Delivery Platform Using Centyrins, Protein Engineering, Design and Selection, vol. 29, Issue 12, pp. 563-572, Dec. 28, 2016.

Groh, et al., R-loops Associated with Triplet Repeat Expansions Promote Gene Silencing in Friedreich Ataxia and Fragile X Syndrome, PLOS Genetics, vol. 10, Issue 5, pp. 1-14, May 1, 2014.

(Continued)

*Primary Examiner* — Ekaterina Poliakova-Georgantas
(74) *Attorney, Agent, or Firm* — LATHROP GPM LLP; James H. Velema, Esq.; Michael J. Spellberg, Esq.

(57) ABSTRACT

The present disclosure provides antisense compounds, methods, and compositions for increasing FXN gene expression. The present disclosure provides antisense compounds, methods, and compositions for the treatment, prevention, or amelioration of diseases, disorders, and conditions associated with FXN in a subject in need thereof. Also contemplated are antisense compounds and methods for the preparation of a medicament for the treatment, prevention, or amelioration of a disease, disorder, or condition associated with FXN.

18 Claims, 15 Drawing Sheets

Specification includes a Sequence Listing.

(56) References Cited

OTHER PUBLICATIONS

Hamajima, et al., Intranasal Administration of HIV-DNA Vaccine Formulated with a Polymer, Carboxymethylcellulose, Augments Mucosal Antibody Production and Cell-Mediated Immune Response, Clinical Immunology and Immunopathology, vol. 88, Issue 2, pp. 205-210, Aug. 1, 1998.

Harlow, et al., Antibodies: A Laboratory Manual, Chapter 14, Cold Spring Harbor Laboratory, Second Edition, 2013.

Herdewijn, Heterocyclic Modifications of Oligonucleotides and Antisense Technology, Antisense and Nucleic Acid Drug Development, vol. 10, Issue 4, pp. 297-310, Jul. 8, 2004.

Hostetler, et al., In Vitro and in Vivo Activity of 1-O-Hexadecylpropane-Diol-3-Phospho-Ganciclovir and 1-O-Hexadecylpropanediol-3-Phospho-Penciclovir in Cytomegalovirus and Herpes Simplex Virus Infections, Antiviral Chemistry and Chemotherapy, vol. 12, No. 1, pp. 61-70, Feb. 2001.

International Search Report & Written Opinion Received for PCT Application No. PCT/US2021/017960, mailed on Jul. 22, 2021.

Ittig, et al., Nuclear Antisense Effects In Cyclophilin A pre-mRNA Splicing By Oligonucleotides: A Comparison Of Tricyclo-DNA With LNA, Nucleic Acids Research, vol. 32, Issue 1, pp. 346-353, 2004.

Ittig, et al., Oligonucleotide Analogues: From Supramolecular Principles to Biological Properties, Academy of Sciences of the Czech Republic, Collection Symposium Series, vol. 7, pp. 21-26, 2005.

Ivanova, et al., Tricyclo-DNA Containing Oligonucleotides as Steric Block Inhibitors of Human Immunodeficiency Virus Type 1 Tat-Dependent Trans-Activation and HIV-1 Infectivity, Oligonucleotides, vol. 17, No. 1, pp. 54-65, Apr. 26, 2007.

Leumann, DNA Analogues: From Supramolecular Principles to Biological Properties, Bioorganic & Medicinal Chemistry, vol. 10, Issue 4, pp. 841-854, Apr. 2002.

Li, et al., Activating Frataxin Expression by Repeat-targeted Nucleic Acids, Nature Communications, vol. 7, No. 10606, pp. 1-8, Feb. 4, 2016.

McCaffrey, et al., Gene Expression: RNA Interference in Adult Mice, Nature, vol. 418, No. 6893, pp. 38-39, Jul. 4, 2002.

Prakash, et al., Targeted Delivery Of Antisense Oligonucleotides To Hepatocytes Using Triantennary N-Acetyl Galactosamine Improves Potency 10-Fold In Mice, Nucleic Acids Research, vol. 42, Issue 13, pp. 8796-8807, Jul. 29, 2014.

Putnam, Antisense Strategies and Therapeutic Applications, American Journal of Health System Pharmacy, vol. 53, No. 2, pp. 151-160, Jan. 15, 1996.

Putnam, et al., Antisense Strategies And Therapeutic Applications—Correction, American Journal of Health-System Pharmacy, vol. 53, No. 3, p. 325, 1996.

Renneberg, et al., Antisense Properties of Tricyclo-DNA, Nucleic Acids Research, vol. 30, Issue 13, pp. 2751-2757, Jul. 2002.

Renneberg, et al., Exploring Hoogsteen and Reversed-Hoogsteen Duplex and Triplex Formation with Tricyclo-DNA Purine Sequences, Chembiochem, vol. 5, Issue 8, pp. 1114-1118, Aug. 2, 2004.

Renneberg, et al., Watson-Crick Base-Pairing Properties of Tricyclo-DNA, Journal of the American Chemical Society, vol. 124, No. 21, pp. 5993-6002, May 7, 2002.

Rusckowski, et al., Biodistribution and Metabolism of a Mixed Backbone Oligonucleotide (GEM 231) Following Single and Multiple Dose Administration in Mice, Antisense and Nucleic Acid Drug Development, vol. 10, Issue 5, pp. 333-345, Oct. 2000.

Schulz, et al., Induction of Oxidative Metabolism by Mitochondrial Frataxin Inhibits Cancer Growth: Otto Warburg Revisited, Journal of Biological Chemistry, vol. 281, Issue 2, pp. 977-981, Jan. 13, 2006.

Shen, et al., Efficient Electroporation of Neuronal Cells Using Synthetic Oligonucleotides: Identifying Duplex RNA and Antisense Oligonucleotide Activators of Human Frataxin Expression, RNA, vol. 25, No. 9, pp. 1118-1129, May 31, 2019.

Smith, et al., Comparison of Biosequences, Advances in Applied Mathematics, vol. 2, No. 4, pp. 482-489, Dec. 1981.

Sørensen, et al., α-L-ribo-Configured Locked Nucleic Acid (α-L-LNA): Synthesis and Properties, Journal of the American Chemical Society, vol. 124, No. 10, pp. 2164-2176, 2002.

Stein, et al., Inhibition of Vesivirus Infections in Mammalian Tissue Culture With Antisense Morpholino Oligomers, Antisense and Nucleic Acid Drug Development, vol. 11, No. 5, pp. 317-325, Oct. 2001.

Virmouni, et al., A Novel GAA-repeat-expansion-based Mouse Model of Friedreich's Ataxia, Disease Models & Mechanisms, vol. 8, No. 3, pp. 225-235, Mar. 1, 2015.

Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.

Wolfrum, et al., Mechanisms And Optimization Of In Vivodelivery Of Lipophilic siRNAs, Nature Biotechnology, vol. 25, No. 10, pp. 1149-1157, Sep. 2007.

Woolf, et al., Specificity Of Antisense Oligonucleotides In Vivo, Proceedings of the National Academy of Sciences, vol. 89, No. 16, pp. 7305-7309, Aug. 15, 1992.

Xia, et al., siRNA-Mediated Gene Silencing in Vitro and In Vivo, Nature Biotechnology, vol. 20, No. 10, pp. 1006-1010, Sep. 16, 2002.

Zhang, et al., PowerBLAST: A New Network BLAST Application for Interactive or Automated Sequence Analysis and Annotation, Genome Research, vol. 7, No. 6, pp. 649-656, Jun. 1, 1997.

Li et al., "Activation of Frataxin Protein Expression by Antisense Oligonucleotides Targeting the Mutant Expanded Repeat", Nucleic Acid Therapeutics, Feb. 2018, 28(1): 23-33.

* cited by examiner

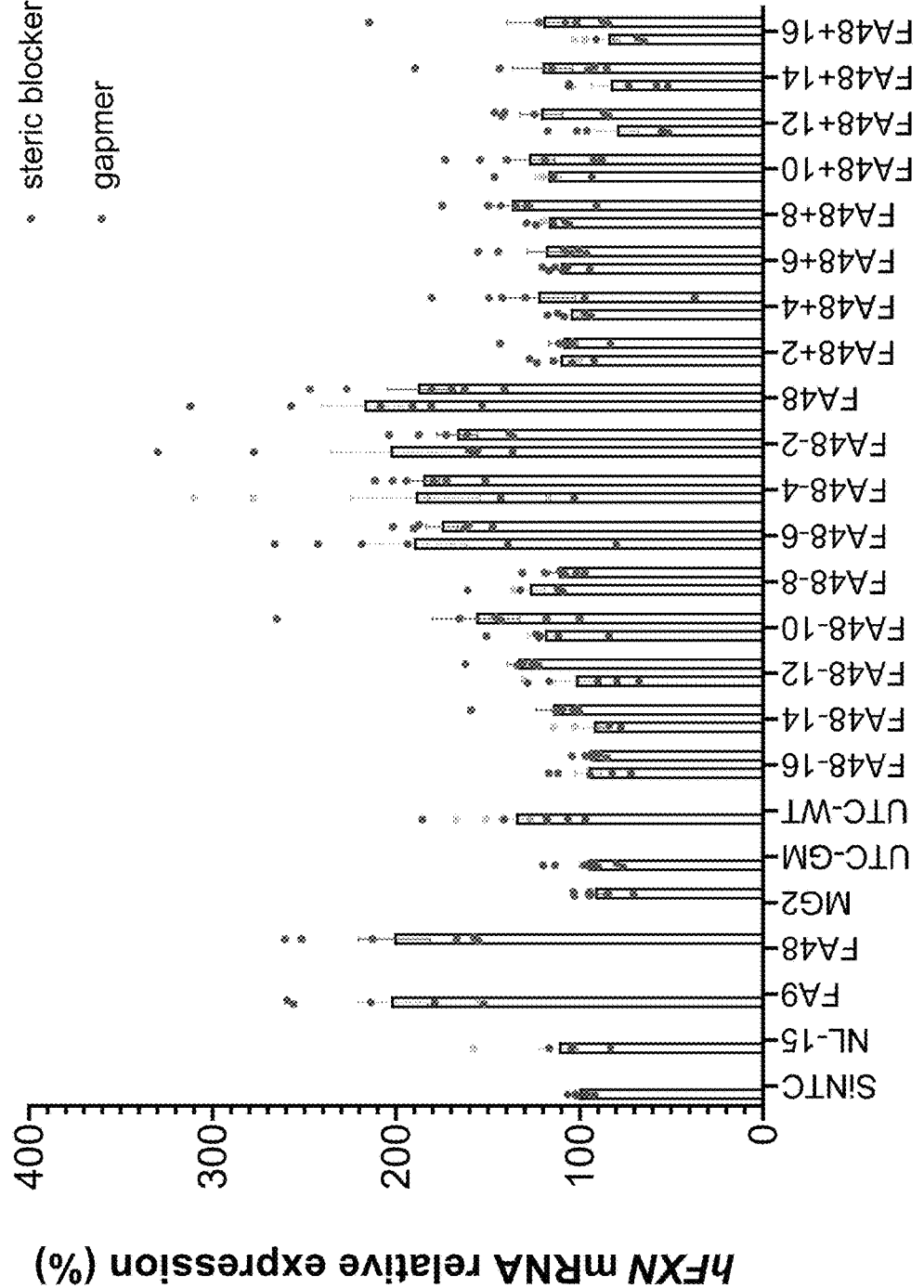

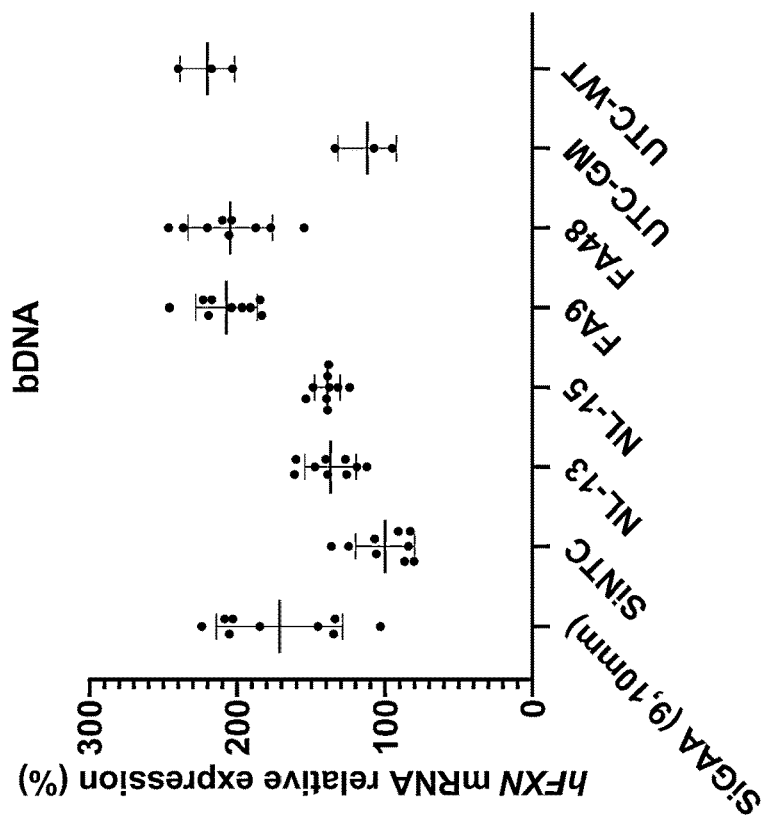
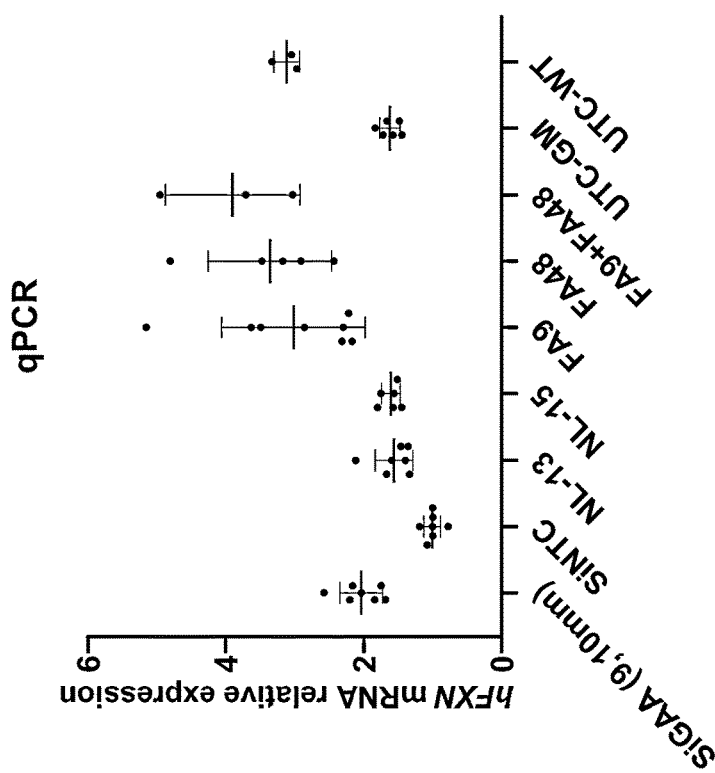
Fig. 7B
Fig. 7A

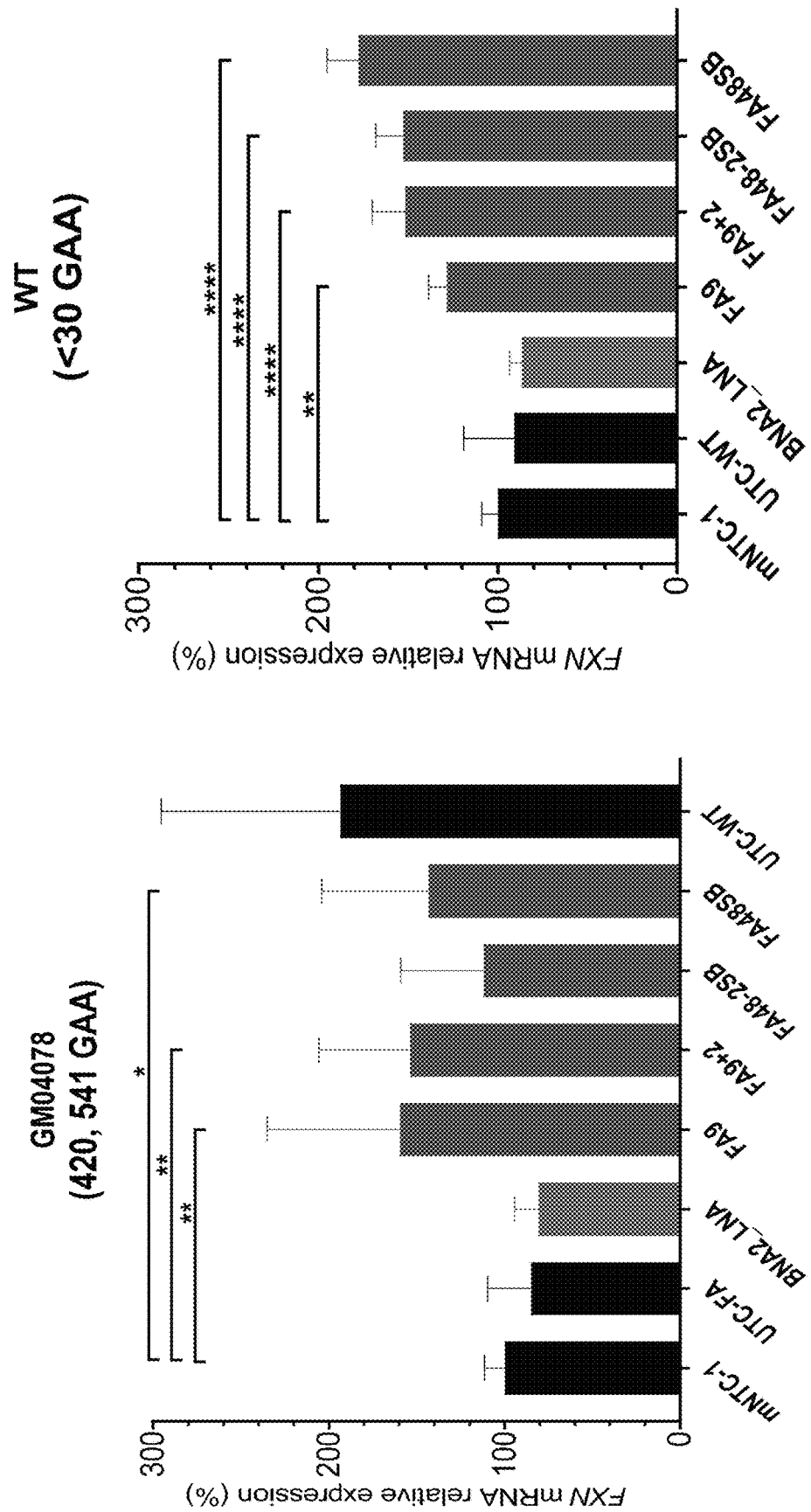

SEQUENCE LISTING

<160> NUMBER OF SEQ ID NOS: 48

<210> SEQ ID NO 1
<211> LENGTH: 11920
<212> TYPE: DNA
<213> ORGANISM: Homo sapiens

<400> SEQUENCE: 1

| | | | | | |
|---|---|---|---|---|---|
| aagaaaactt | tcacaatttg | catcccttg | taatatgtaa | cagaaataaa | attctctttt | 60 |
| aaaatctatc | aacaataggc | aaggcacggt | ggctcacgcc | tgtcgtctca | gcactttgtg | 120 |
| aggcccaggc | gggcagatcg | tttgagccta | gaagttcaag | accaccctgg | gcaacatagc | 180 |
| gaaaccccct | ttctacaaaa | aatacaaaaa | ctagctgggt | gtggtggtgc | acacctgtag | 240 |
| tcccagctac | ttggaaggct | gaaatgggaa | gactgcttga | gcccgggagg | gagaagttgc | 300 |
| agtaagccag | gaccacacca | ctgcactcca | gcctgggcaa | cagagtgaga | ctctgtctca | 360 |
| aacaaacaaa | taaatgaggc | gggtggatca | cgaggtcagt | agatcgagac | catcctggct | 420 |
| aacacggtga | aacccgtctc | tactaaaaaa | aaaaaaaaat | acaaaaaatt | agccaggcat | 480 |
| ggtggcgggc | gcctgtagtc | ccagttactc | gggaggctga | gcaggagaa | tggcgtgaaa | 540 |
| ccgggaggca | gagcttgcag | tgagccgaga | tcgcaccact | gccctccagc | ctgggcgaca | 600 |
| gagcgagact | ccgtctcaat | caatcaatca | atcaataaaa | tctattaaca | atatttattg | 660 |
| tgcacttaac | aggaacatgc | cctgtccaaa | aaaactttta | cagggcttaa | ctcattttat | 720 |
| ccttaccaca | atcctatgaa | gtaggaactt | ttataaaacg | cattttataa | acaaggcaca | 780 |
| gagaggttaa | ttaacttgcc | ctctggtcac | acagctagga | agtgggcaga | gtacagattt | 840 |
| acacaaggca | tccgtctcct | ggccccacat | acccaactgc | tgtaaaccca | taccggcggc | 900 |
| caagcagcct | caatttgtgc | atgcacccac | ttcccagcaa | gacagcagct | cccaagttcc | 960 |
| tcctgtttag | aattttagaa | gcggcgggcc | accaggctgc | agtctcccctt | gggtcagggg | 1020 |
| tcctggttgc | actccgtgct | ttgcacaaag | caggctctcc | attttttgtta | aatgcacgaa | 1080 |
| tagtgctaag | ctgggaagtt | cttcctgagg | tctaacctct | agctgctccc | ccacagaaga | 1140 |
| gtgcctgcgg | ccagtggcca | ccaggggtcg | ccgcagcacc | cagcgctgga | gggcggagcg | 1200 |
| ggcggcagac | ccggagcagc | atgtggactc | tcgggcgccg | cgcagtagcc | ggcctcctgg | 1260 |
| cgtcacccag | cccagcccag | gcccagaccc | tcacccgggt | cccgcggccg | gcagagttgg | 1320 |
| ccccactctg | cggccgccgt | ggcctgcgca | ccgacatcga | tgcgacctgc | acgccccgcc | 1380 |
| gcgcagtaag | tatccgcgcc | gggaacagcc | gcgggccgca | cgccgcgggc | cgcacgccgc | 1440 |
| acgcctgcgc | agggaggcgc | cgcgcacgcc | gggtcgctc | cgggtacgcg | cgctggacta | 1500 |
| gctcaccccg | ctccttctca | gggcggcccg | gcggaagcgg | ccttgcaact | cccttctctg | 1560 |
| gttctcccgg | ttgcatttac | actggcttct | gctttccgaa | ggaaaagggg | acattttgtc | 1620 |
| ctgcggtgcg | actgcgggtc | aaggcacggg | cgaaggcagg | gcaggctggt | ggaggggacc | 1680 |
| ggttccgagg | ggtgtgcggc | tgtctccatg | cttgtcactt | ctctgcgata | acttgtttca | 1740 |
| gtaatattaa | tagatggtat | ctgctagtat | atacatacac | ataatgtgtg | tgtctgtgtg | 1800 |
| tatctgtata | tagcgtgtgt | gttgtgtgtg | tgtgtttgcg | cgcacgggcg | cgcgcacacc | 1860 |
| taatattttc | aaggctggat | tttttgaac | gaaatgcttt | cctggaacga | ggtgaaactt | 1920 |
| tcagagctgc | agaatagcta | gagcagcagg | ggccctggct | tttggaaact | gacccgacct | 1980 |
| ttattccaga | ttctgcccca | ctccgcagag | ctgtgtgacc | ttgggggatt | ccctaacct | 2040 |
| ctctgagacg | tggctttgtt | ttctgtaggg | agaagataaa | ggtgacgccc | attttgcgga | 2100 |

```
cctggtgtga ggattaaatg ggaataacat agataaagtc ttcagaactt caaattagtt    2160
cccctttctt cctttggggg gtacaaagaa atatctgacc cagttacgcc acggcttgaa    2220
aggaggaaac ccaaagaatg gctgtgggga tgaggaagat tcctcaaggg gaggacatgg    2280
tatttaatga gggtcttgaa gatgccaagg aagtggtaga gggtgtttca cgaggaggga    2340
accgtctggg caaaggccag gaaggcggaa ggggatccct tcagagtggc tggtacgccg    2400
catgtattag gggagatgaa agaggcaggc cacgtccaag ccatatttgt gttgctctcc    2460
ggagtttgta ctttaggctt gaacttccca cacgtgttat ttggcccaca ttgtgtttga    2520
agaaactttg ggattggttg ccagtgctta aaagttagga cttagaaaat ggatttcctg    2580
gcaggacgcg gtggctcatg cccataatct cagcactttg ggaggcctag aaggtggat     2640 cacctgaggt ccggagttca agactaacct ggccaacatg gtgaaaccca gtatctacta    2700
aaaaatacaa aaaaaaaaa aaaagaagaa gaagaagaag aaaataaaga aaagttagcc     2760
gggcgtggtg tcgcgcgcct gtaatcccag ctactccaga ggctgcggca ggagaatcgc    2820
ttgagcccgg gaggcagagg ttgcattaag ccaagatcgc ccaatgcact ccggcctggg    2880
cgacagagca agactccgtc tcaaaaaata ataataataa ataaaaataa aaataaaat     2940 ggatttccca gcatctctgg aaaaataggc aagtgtggcc atgatggtcc ttagatctcc    3000
tctaggaaag cagacattta ttacttggct tctgtgcact atctgagctg ccacgtattg    3060
ggcttccacc cctgcctgtg tggacagcat gggttgtcag cagagttgtg ttttgttttg    3120 ttttttttgag acagagtttc cctcttgttg cccaggctgg agtgcagtgg ctcagtctca    3180
gctcactgca acctctgcct cctgggttca agtgattctc ctgcctcagc ctcccgagta    3240
gctgggatta tcggctaatt ttgtatttt agtagagaca gatttctcca tgttggtcag    3300
gctggtctcg aactcccaac ctcaggtgat ccgcccacct cgcctccca aagtgctgga    3360 attacaggcg tgagccaccg cgtctggcca tcagcagagt ttttaattta ggagaatgac    3420
aagaggtggt acagtttttt agatggtacc tggtggctgt taagggctat tgactgacaa    3480
acacacccaa cttggcgctg ccgcccagga ggtggacact gggtttctgg atagatggtt    3540
agcaacctct gtcaccagct gggcctcttt ttttctatac tgaattaatc acatttgttt    3600
aacctgtctg ttccatagtt cccttgcaca tcttgggtat ttgaggagtt gggtgggtgg    3660
cagtggcaac tggggccacc atcctgttta attatttta agccctgact gtcctggatt     3720 gacccctaagc tccccctggt ctccaaaatt catcagaaac tgagttcact tgaaggcctc    3780
ttccccaccc ttttctccac cccttgcatc tacttctaaa gcagctgttc aacagaaaca    3840
gaatgggagc cacacacata attctacatt ttctagttaa aaagaaaaaa aaatcatttt    3900
caacaatata tttattcaac ctagtacata caaaatatta tcattccaac atgtaatcag    3960
tattttaaaa atcagtaatg agaccaggca cggtggctca cgactgtaat cccaggactt    4020
tgggaggccg aggcgagtgg atcatctgag atcaggagtt caagaccagc ctggccaaca    4080
tggtgaaacc ccatctctac taaaaactag ctcagcatgg tggtgggtgc ctgtagtccc    4140
agctactcgg gaggctgagg catgagaatc acttgagccc aggaggcaga ggttgcagtg    4200
agccaagatt tgggggatt ctgtgacata caaaaaaaat cagtaataag atatcttgca     4260
tactcttttc gtactcatat acttccagca tatctcaatt cacaatttct aagtaaatgc    4320
tctatctgta tttacttta taaaattcac aattaaaaat gaaggttcac atagtcaagt     4380
tgttccaaac acacttaaat gtctcctagg ctgggtgtgg ttgctcacac ctgtaatccc    4440
```

```
agcactttgg gaggctgaga tgggcggatc acctgaggtc aggagtttga gaccagcctg   4500
gccaacatgg tgaaacccg tctctactaa aaatacaaaa attagctgga tgtggtggca    4560
ctcacctgta atcccagcta ctcaggaggc tgaggcagga taattgcttg aacccgggag   4620
gtggtggagg ttgcagtgag ccgagatcgc accactgcct tccaacctgg gcgacagagc   4680
gagactccgt ctcaaaaaaa aaaaaaggc tcctaataac tttattactt tattatcacc    4740
tcaaataatt aaaattaaat gaagttgaaa atccaggtcc tcagtcccat tagccacatt   4800
tctagtgctc agtagccacg ggggctggtg accaccacat gggacagcat atttagtacc   4860
tgatcattgg ttctcagatc tggctactca gcagaaccaa gaatccacag aaacggcttt   4920
taaaagcaca gccccacagc ccccagcccc agccttacct acctggaggc tgggaaggac   4980
tctgattcca cgaggcagcc tatgtttttt gatggaggga tgtgacaggg gctgcatctt   5040
taacgtttcc tcttaaatac tggagacagc ttcgaggagg agataactgg atgtgtctta   5100
gtccatttga tggagggatg tgacggggct gcgtctttaa cgtttcctct taaataccgg   5160
agacagcttc gagaaggaga taactggatg tttcttagtc cattttctgt tgcttgtgac   5220
agaatacctg aaactgggca atttatatgg taaaaaattt tcttcttact gctctggagg   5280
ctgagaagtc aaagtcaag tcccttcttg ctggtgggga ctttgcagag tattgaggcg    5340
gcaccgggcg tcatatggta aggggctgag tgtgctacct caggtgtctt tttcttttct   5400
tataaagcct aactagtttc actcccatga taacccatta atctatgaat ggattaatcc   5460
attattgagg gaagaacctt catgacccag tcaccgctta aaggcccac ctctcaatac    5520 tgccacatcg ggaattaagt ttcaacatga gtttcggagg tgacaaacat tcaaaccata   5580
gcatgctgtc tcttaaatga ctcaataagc tcctgtggca tccacttctg catgccttgg   5640
gcagctttta gacatctgtc catttcccta gagggacaag accaccacct gtgatcctat   5700
gaccttttgg ctttaggcct aacaagcagg ttataccctc actcactttc aaatcatttt   5760
tattgtcttg cagacaattt acacaagttt acacatagaa aaggatatgt aaatatttat   5820
acgctgccgg gcgcggtggc tcacgcctgt aatcccagca ctttgggagg ccgaggcagg   5880
tggatcacga gttcaggaga tggagaccat cctggctaat acgatgaaac ccatctcta    5940 ctaaaaatac aaaaaattag ccgggcgtgg tgacgggtgc ctgtagtccc cactactcgg   6000
gacgctgagg caggagaatg gcgtgaaccc gggaggcaga gcttgcagtg atccgagatc   6060
gtgccactgc actccagcct gggtgacaga gcgagactgc atctcaaaga aaaaaataaa   6120
taaataaata aatatttata ctgcttataa actaataata aatgctatgg tctgcatgtt   6180
tgtgtcaccc caccattcat atgttaaaac ctaatcacca aagtgatatt aggaggtggg   6240
gcccttggga ggtgatgagg tatgagggtg gagcccatat gattgggatt agtgccttc    6300 taaaatagcc caacggagcc cagtgacaag gcatcatcta tgaaccagga aactggccct   6360
caccagacac caaagctgtt ggtgcattga tcttggattt cccaccctcc aggactctaa   6420
gaaacacatt tctattgttt ataagccacc cagtggctgg tattttgtta aacatccca    6480 gactaagaca ataacaaat acttgtatcc ctgacaccag gttaagagat agaatttgtt    6540
tgttcctctg gaggcccttg tcttcacccc atcactgccc tgtcctccct ggaggaatct   6600
gccagcccga attctgttca tcgtaccctc ctttttcttag agtttgacct cctctgtatc   6660
tcccccaatc catgtattgc ttatatacaa ggtattctgc tgtatctgtt ctgctatggc   6720 ttgcccctttt tgttcaacac tgtttttgtg cgtcatctgc attgatgcat gcagttgtcc   6780
tttatttgtt ctcactgctg gatagtatct ggttgggtaa atatatcaca ctgtaaatca   6840
```

```
cactatccag gttcctttag gtgacatttg gttgattgca gtgttctgtt gttacgatgg    6900
tgctgctgtg actgttcttg tgcatggaca gaagttcctt tcaggtgaat ttctcagaat    6960
ggaattgctg ggcaaagggg cagccaataa tcaactcatt tgatgccaaa agtggtggtg    7020
ccagttcatc ctcccctgcg aggtatgggt cctgattcac tcttcaagtg ctgtggtttg    7080
acagggccgg gggtgacaag gggacacctg ggaaggaaag ctgggctccc tgctggccat    7140
ccaggccagt ccttaccagg gggtaggcaa tgattgggtc aagtggttcc tgaccactgg    7200
gcctgagact tcaggcccag aaactatcta atatttcctc aaatgcatcc catgagcagg    7260
cactgtgtga gtgagcacac acatctgaag cctcaagcta gcaagcctta ccatgacttg    7320
tggtccaagg gctcacgggt gacctggagt tagagggaga catggctgcc aggtggcttt    7380
agaaagaaca ctcatcatgg ccaggtgcgg tggcttacgc ctgtaatccc agcactttgg    7440
gaggccaagg tgggtggatc atgaggtcag gagtgagacc agcctgacca acatgctgaa    7500
acctgtctct cctaaaaaca caaaaattag ctgggcatgg aggtgcacgc ctgtaatccc    7560
agctactcag gaggctgagg caggagaatc acttgaaccc gggaggcgga ggttgcaata    7620
agcctagatt gtgccactgc attccagcct gggcaacaga gcaagactcc gtctcagaaa    7680 aaaaaaaaa aaggaagaac actcatccta tgaccttgac ctccaagctt tgcctccctc    7740
aagcagaaca gaatggagcc tcccttaggc agaggcggaa gtttgcctct cacctagttc    7800
tccattcttt tgttcagagc ctgaatacccc tcaggctctg tacttggggt atttctgttc    7860
tcttgtttta tgctcacggt tgtgaggttt gttgtgagta ccacgatccc ttccttcaga    7920
ggagtaaact gaggttccaa aaggtttagc agttgcccga ggaatattaa attggcaaaa    7980
gcaggtagaa tataaagcaa ggagtatttg gcaacggttc tttttttatga ttaaaaacag    8040 ccgaagaaag acttctactt gtgcctttga aggagtaact gcatttgacc ttcccaccag    8100
taacaaccat caaatctcta ttaaattaaa cacacacaca cacaaacaaa acagctatt    8160 gtgaaggtat cagcgactaa gacaactaag gtttgagggg ccaggatcct ggagagatgg    8220
aaacttccct gaggtgagcc ccacattctc agacactttt ccttggatgt tttgagcact    8280
gctttaattc ctgggaaaac aattccttcc actgtgcaca gactctgggg ccagacagct    8340
tgggttcaat cccagctctg ccacttaatg tctgtgtatc tgtgtaggca agttacccttt    8400 tggtgcgtca gtttcctcat ctgtaaaaca caactatagt tgatcctcat tcgttaagag    8460
tctgtacttg ttaatttgct cacttgctaa aatttgttac cccaaaatca gtaccctag    8520 cctttgggg tcgtttcaaa gatgtgtgca gagcggcaaa aaaatgtgag ctcctccagg    8580
ctcatgttcc cagccaaggt ccaacaaagt gctgccctgc cttcttattt cagctgtcat    8640
agtgtaaact gtgtcctttt cacagtctga ttagtgccat gtttttcaga ttttttatgct    8700 tttttcttgg ttatttctct gttaaaattg tctccaagtg tagtgcaaag tttagcacga    8760
ggaggctgtg atgttcctta cagagaaaat gcatgtgtta gagaagcttt gtcaggcatg    8820
agttaaggtg ctgttgtcct gagatcaatt aatttgttgt tgttgttgtt tgagacaggg    8880
tctccctctg ttgcccaggc tgctggagtg caatggtgta atcatagctc actgcagcct    8940
ctacctctct ggctcaagca atcctcccac ctcggcctcc tgagtagctg ggactacagg    9000
tacaccccac cacacccaga taatgttttt gatattttt taggtggaat tttgctcatc    9060
acccaggctg gagtgcaatg gtgcgatcct ggctcactgc aacctccacc tcccggattc    9120
aagcaattct tctgcctcag cctcctgagt agcacagatt acaggcacat gtcatcacgc    9180
```

-continued

```
cttgctaatt tttgtgtttt tagtagaggc ggggtttcac catgttggcc aggctagtct    9240
tgaactcctg acctcaggtg atccacccgc ctccgcctcc caaactgcag agattatagg    9300
cacgaaccac aatgcccggc ctcatgtttt ttatttttca agttgaaatg aggtctctct    9360
atgttgccca ggttggtctc aaactcttga gctcaagtaa tcctcccacc ttggcctccc    9420
aaagtgcggg gattacaggt gtgagctacc atgcccagcc aagatcagtg ttaatgaatc    9480
aactatatat attacataag gtgtctttaa acagaaataa ggttatatat tgatcgattg    9540
gtaacaatgt tgtgaccagc agcttacagg gtacctagcc ttgtatttct cctataaata    9600
atttgctcgt tgagtgtttg tggcaacttt gtagcacata actaccaaga ataaggactg    9660
taataagagt acgtccctca caggattgta atgaagactg agtccattta cataaaggct    9720
gagagcagtg tcaagcagat ggagaacact gtagaatgtg cgatagctct aacagtggtt    9780
atcatggctg ccctctcact tcttcagaga catgtgtttc taaggtctgc actctgcccc    9840
accctcccca tccactgtcc cccagcccgt ttcctcctcc acttacttcc cagccctgtg    9900
ccttctgcct tctcttttct gagtttgcta agggcactgc tggctcaaga gcagtaacta    9960
acagtctctc gcctcttctc tccatggcaa ccagtgacct ttggagaatg taaaccttat   10020
caccaatctc ttaaagccct tcggtgcctt cccaggatga cgtccagctg aggtccttgg   10080
caagacccag ggcgccccct cctcgctcca tcacctcccc tgtcacctcc cctgcatctc   10140
cctactccag ctgcaccact cttgtgcccc agtggctctt gtctgattat ttccttcatc   10200
tccccagctg gtcagcagag ctggtggtaa tcaactcaga ccctgtcacc tggatgtcca   10260
gcagttaggg actaaaaaaa atcaacaggt cacattctgt cctgcagatc atgataataa   10320
gatctgtcag acagcagtca gcagtcagag ccaaatcttc tggacttcag caggattctg   10380
cctcttgcta tttcctgttg cctctcttag tgaccttta agagcattgt ggatgcctcc   10440
cagcctcctg ctaaccaccc tgtaacctga acagcctgca gcagccctgc ccagtagaac   10500
ttcctgatgt gatggaaatg ctgtgtctgc accactagcc acatgtggcc acaggattct   10560
cgaaactggt ggtgcagttg aggagctgac tttatatttt atctcattaa atttaaatgt   10620
aaatagctac gtgtggcttg ttggctagcc tattggaaaa cacgggctta gagagacaca   10680
gggagaatca ctgtaatgca ctaaaagaag gtaaaaaaaa aaaatcctca agaaatattc   10740
ctaaaatact ttaatatagg gctgggtgcg gtggctcaca tccagcattt tgggaagctg   10800
aggagggcag atcacttgag gccaggagtt caagaccagc ctggccaaca tggtgaaacc   10860
ccgtctctac taaaaataca aaaaatcggg tgcggtggcg ggtgcctgta atcccagcta   10920
cgcgggaggc tgaggcacga gaatcactcg aacccgggag gcggggttg cagtgagccg   10980
agatcgtgcc actgcactcc agcctgggcg acagagcgag acttcatctc aaaaacaaaa   11040
aacaaaaacc aaaaaaaaaa acttcagcat gattatttaa ccaaaatgca ggttagttgt   11100
tcaccggatg cagagtccaa ttaacaagag caaggcctgg taccaaaaaa agtgaattta   11160
ctccgaaact agcttgggtg aggggtacaa agcatcctgc ctttctttaa aagtgctgct   11220
tccccttgga agtagaaagt ggacactttt ataaggtaag gggggaagtg tgcaagggca   11280
agtgggggg tccctctgct agttccgtgc atactctaca ggacagttga cttggcacct   11340
tcctggttag taataagctg tagcagtggc caagtgggca tgctttcagt atgccctccc   11400
agtgaatgaa agtcctgagg caaccccaa gggtggaagt gccaggccac cacccactgg   11460
aggtgaaagt tccgtgatgg gtttgctttg gtctgcgaat ctactgtcat gtggagagat   11520
ctgtgctctg gaagagcata cagttagaaa agcttgccct gaagggaatg tatggtgaag   11580
```

```
gggaggtgaa aggttatatt tgcatttctg aagggctaag taggaaaccg ggaaccaggg     11640
gagaggagaa gagaagagag gataattttt tttaagaaaa gcaacatatt ccctttttct     11700
tagaaaaaat ggagcactcg gttacaggca ctcgaatgta aagtagcaa tatataaatt      11760 atgcattaat gggttataat tcactgaaaa atagtaacgt acttcttaac tttggctttc     11820
agagttcgaa ccaacgtggc ctcaaccaga tttggaatgt caaaaagcag agtgtctatt    11880
tgatgaattt gaggaaatct ggaactttgg gccacccagg                           11920

<210> SEQ ID NO 2
<211> LENGTH: 2724
<212> TYPE: DNA
<213> ORGANISM: Homo sapiens

<400> SEQUENCE: 2
aagaaaactt tcacaatttg catccctttg taatatgtaa cagaaataaa attctctttt       60
aaaatctatc aacaataggc aaggcacggt ggctcacgcc tgtcgtctca gcactttgtg     120
aggcccaggc gggcagatcg tttgagccta aagttcaag accaccctgg gcaacatagc      180
gaaaccccct ttctacaaaa aatacaaaaa ctagctgggt gtggtggtgc acacctgtag    240
tcccagctac ttggaaggct gaaatgggaa gactgcttga gcccgggagg gagaagttgc    300
agtaagccag gaccacacca ctgcactcca gcctgggcaa cagagtgaga ctctgtctca    360
aacaaacaaa taaatgaggc gggtggatca cgaggtcagt agatcgagac catcctggct    420
aacacggtga aacccgtctc tactaaaaaa aaaaaaaatt acaaaaaatt agccaggcat    480
ggtggcgggc gcctgtagtc ccagttactc gggaggctga ggcaggagaa tggcgtgaaa    540
ccgggaggca gagcttgcag tgagccgaga tcgcaccact gccctccagc ctgggcgaca    600
gagcgagact ccgtctcaat caatcaatca atcaataaaa tctattaaca atatttattg    660
tgcacttaac aggaacatgc cctgtccaaa aaaaacttta cagggcttaa ctcattttat    720
ccttaccaca atcctatgaa gtaggaactt ttataaaacg catttttataa acaaggcaca    780 gagaggttaa ttaacttgcc ctctggtcac acagctagga agtgggcaga gtacagattt    840
acacaaggca tccgtctcct ggccccacat acccaactgc tgtaaaccca taccggcggc    900
caagcagcct caatttgtgc atgcacccac ttcccagcaa gacagcagct cccaagttcc    960
tcctgtttag aattttagaa gcggcgggcc accaggctgc agtctccctt gggtcagggg    1020
tcctggttgc actccgtgct ttgcacaaag caggctctcc attttttgtta aatgcacgaa   1080 tagtgctaag ctgggaagtt cttcctgagg tctaacctct agctgctccc ccacagaaga    1140
gtgcctgcgg ccagtggcca ccaggggtcg ccgcagcacc cagcgctgga gggcggagcg    1200
ggcggcagac ccggagcagc atgtggactc tcggcgccg cgcagtagcc ggcctcctgg     1260
cgtcacccag cccagcccag gcccagaccc tcacccgggt cccgcggccg gcagagttgg    1320
ccccactctg cggccgccgt ggcctgcgca ccgacatcga tgcgacctgc acgcccgcc     1380 gcgcagtaag tatccgcgcc gggaacagcc gcggccgca cgccgcgggc cgcacgccgc     1440
acgcctgcgc agggaggcgc cgcgcacgcc ggggtcgctc cgggtacgcg cgctggacta    1500
gctcaccccg ctccttctca gggcggcccg gcggaagcgg ccttgcaact cccttctctg   1560
gttctcccgg ttgcatttac actggcttct gctttccgaa ggaaaagggg acattttgtc    1620
ctgcggtgcg actgcgggtc aaggcacggg cgaaggcagg gcaggctggt ggaggggacc    1680
ggttccgagg ggtgtgcggc tgtctccatg cttgtcactt ctctgcgata acttgtttca    1740
```

-continued

| | |
|---|---|
| gtaatattaa tagatggtat ctgctagtat atacatacac ataatgtgtg tgtctgtgtg | 1800 |
| tatctgtata tagcgtgtgt gttgtgtgtg tgtgtttgcg cgcacgggcg cgcgcacacc | 1860 |
| taatattttc aaggctggat tttttttgaac gaaatgcttt cctggaacga ggtgaaactt | 1920 |
| tcagagctgc agaatagcta gagcagcagg ggccctggct tttggaaact gacccgacct | 1980 |
| ttattccaga ttctgcccca ctccgcagag ctgtgtgacc ttgggggatt cccctaacct | 2040 |
| ctctgagacg tggctttgtt ttctgtaggg agaagataaa ggtgacgccc attttgcgga | 2100 |
| cctggtgtga ggattaaatg ggaataacat agataaagtc ttcagaactt caaattagtt | 2160 |
| ccccttctctt cctttgggg gtacaaagaa atatctgacc cagttacgcc acggcttgaa | 2220 |
| aggaggaaac ccaaagaatg gctgtgggga tgaggaagat tcctcaaggg gaggacatgg | 2280 |
| tatttaatga gggtcttgaa gatgccaagg aagtggtaga gggtgtttca cgaggaggga | 2340 |
| accgtctggg caaaggccag gaaggcggaa ggggatccct tcagagtggc tggtacgccg | 2400 |
| catgtattag gggagatgaa agaggcaggc cacgtccaag ccatatttgt gttgctctcc | 2460 |
| ggagtttgta ctttaggctt gaacttccca cacgtgttat ttggcccaca ttgtgtttga | 2520 |
| agaaactttg ggattggttg ccagtgctta aaagttagga cttagaaaat ggatttcctg | 2580 |
| gcaggacgcg gtggctcatg cccataatct cagcactttg ggaggcctag gaaggtggat | 2640 |
| cacctgaggt ccggagttca agactaacct ggccaacatg gtgaaaccca gtatctacta | 2700 |
| aaaaatacaa aaaaaaaaa aaaa | 2724 |

<210> SEQ ID NO 3
<211> LENGTH: 9178
<212> TYPE: DNA
<213> ORGANISM: Homo sapiens

<400> SEQUENCE: 3

| | |
|---|---|
| aataaagaaa agttagccgg gcgtggtgtc gcgcgcctgt aatcccagct actccagagg | 60 |
| ctgcggcagg agaatcgctt gagcccggga ggcagaggtt gcattaagcc aagatcgccc | 120 |
| aatgcactcc ggcctgggcg acagagcaag actccgtctc aaaaaataat aataataaat | 180 |
| aaaaataaaa aataaaatgg atttcccagc atctctggaa aaataggcaa gtgtggccat | 240 |
| gatggtcctt agatctcctc taggaaagca gacatttatt acttggcttc tgtgcactat | 300 |
| ctgagctgcc acgtattggg cttccacccc tgcctgtgtg dacagcatgg gttgtcagca | 360 |
| gagttgtgtt ttgttttgtt ttttgagac agagtttccc tcttgttgcc caggctggag | 420 |
| tgcagtggct cagtctcagc tcactgcaac ctctgcctcc tgggttcaag tgattctcct | 480 |
| gcctcagcct cccgagtagc tgggattatc ggctaatttt gtattttag tagagacaga | 540 |
| tttctccatg ttggtcaggc tggtctcgaa ctcccaacct caggtgatcc gcccacctcg | 600 |
| ccctcccaaa gtgctggaat tacaggcgtg agccaccgcg tctggccatc agcagagttt | 660 |
| ttaatttagg agaatgacaa gaggtggtac agtttttttag atggtacctg gtggctgtta | 720 |
| agggctattg actgacaaac acacccaact tggcgctgcc gcccaggagg tggacactgg | 780 |
| gtttctggat agatggttag caacctctgt caccagctgg gcctcttttt ttctatactg | 840 |
| aattaatcac atttgtttaa cctgtctgtt ccatagttcc cttgcacatc ttgggtattt | 900 |
| gaggagttgg gtgggtggca gtggcaactg gggccaccat cctgtttaat tatttttaaag | 960 |
| ccctgactgt cctggattga ccctaagctc ccctggtct ccaaaattca tcagaaactg | 1020 |
| agttcacttg aaggcctctt ccccacccctt ttctccaccc cttgcatcta cttctaaagc | 1080 |
| agctgttcaa cagaaacaga atgggagcca cacacataat tctacatttt ctagttaaaa | 1140 |

-continued

```
agaaaaaaaa atcattttca acaatatatt tattcaacct agtacataca aaatattatc    1200
attccaacat gtaatcagta ttttaaaaat cagtaatgag accaggcacg gtggctcacg    1260
actgtaatcc caggactttg ggaggccgag gcgagtggat catctgagat caggagttca    1320
agaccagcct ggccaacatg gtgaaacccc atctctacta aaaactagct cagcatggtg    1380
gtgggtgcct gtagtcccag ctactcggga ggctgaggca tgagaatcac ttgagcccag    1440
gaggcagagg ttgcagtgag ccaagatttt gggggattct gtgacataca aaaaaaatca    1500
gtaataagat atcttgcata ctcttttcgt actcatatac ttccagcata tctcaattca    1560
caatttctaa gtaaatgctc tatctgtatt tacttttata aaattcacaa ttaaaaatga    1620
aggttcacat agtcaagttg ttccaaacac acttaaatgt ctcctaggct gggtgtggtt    1680
gctcacacct gtaatcccag cactttggga ggctgagatg gcggatcac ctgaggtcag    1740 gagtttgaga ccagcctggc caacatggtg aaaccccgtc tctactaaaa atacaaaaat    1800
tagctggatg tggtggcact cacctgtaat cccagctact caggaggctg aggcaggata    1860
attgcttgaa cccgggaggt ggtggaggtt gcagtgagcc gagatcgcac cactgccttc    1920
caacctgggc gacagagcga gactccgtct caaaaaaaaa aaaaaggctc taataacatt    1980
tattacttta ttatcacctc aaataattaa aattaaatga agttgaaaat ccaggtcctc    2040
agtcccatta gccacatttc tagtgctcag tagccacggg ggctggtgac caccacatgg    2100
gacagcatat ttagtacctg atcattggtt ctcagatctg gctactcagc agaaccaaga    2160
atccacagaa acggctttta aaagcacagc cccacagccc ccagcccag ccttacctac    2220 ctggaggctg ggaaggactc tgattccacg aggcagccta tgttttttga tggagggatg    2280
tgacaggggc tgcatcttta acgtttcctc ttaaatactg gagacagctt cgaggaggag    2340
ataactggat gtgtcttagt ccatttgatg gagggatgtg acggggctgc gtctttaacg    2400
tttcctctta aataccggag acagcttcga gaaggagata actggatgtt cttagtcca    2460 ttttctgttg cttgtgacag aatacctgaa actgggcaat ttatatggta aaaaatttc    2520 ttcttactgc tctggaggct gagaagtcca agtcaagtc ccttcttgct ggtggggact    2580
ttgcagagta ttgaggcggc accgggcgtc atatggtaag gggctgagtg tgctacctca    2640
ggtgtctttt tcttttctta taaagcctaa ctagtttcac tcccatgata acccattaat    2700
ctatgaatgg attaatccat tattgaggga agaaccttca tgacccagtc accgcttaaa    2760
ggccccacct ctcaatactg ccacatcggg aattaagttt caacatgagt ttcggaggtg    2820
acaaacattc aaaccatagc atgctgtctc ttaaatgact caataagctc ctgtggcatc    2880
cacttctgca tgccttgggc agcttttaga catctgtcca ttttcctaga gggacaagac    2940
caccacctgt gatcctatga ccttttggct ttaggcctaa caagcaggtt ataccctcac    3000
tcactttcaa atcattttta ttgtcttgca gacaatttac acaagtttac acatagaaaa    3060
ggatatgtaa atatttatac gctgccgggc gcggtggctc acgcctgtaa tcccagcact    3120
ttgggaggcc gaggcaggtg gatcacgagt tcaggagatg gagaccatcc tggctaatac    3180
gatgaaaccc catctctact aaaaatacaa aaaattagcc gggcgtggtg acgggtgcct    3240
gtagtcccca ctactcggga cgctgaggca ggagaatggc gtgaacccgg gaggcagagc    3300
ttgcagtgat ccgagatcgt gccactgcac tccagcctgg gtgacagagc gagactgcat    3360
ctcaaagaaa aaaataaata aataaataaa tatttatact gcttataaac taataataaa    3420
tgctatggtc tgcatgtttg tgtcacccca ccattcatat gttaaaacct aatcaccaaa    3480
```

```
gtgatattag gaggtggggc ccttgggagg tgatgaggta tgagggtgga gcccatatga    3540
ttgggattag tgcccttcta aaatagccca acggagccca gtgacaaggc atcatctatg    3600
aaccaggaaa ctggccctca ccagacacca aagctgttgg tgcattgatc ttggatttcc    3660
caccctccag gactctaaga aacacatttc tattgtttat aagccaccca gtggctggta    3720
ttttgttata acatcccaga ctaagacaaa taacaaatac ttgtatccct gacaccaggt    3780
taagagatag aatttgtttg ttcctctgga ggcccttgtc ttcacccat cactgccctg     3840
tcctccctgg aggaatctgc cagcccgaat tctgttcatc gtaccctcct tttcttagag    3900
tttgacctcc tctgtatctc ccccaatcca tgtattgctt atatacaagg tattctgctg    3960
tatctgttct gctatggctt gccccttttg ttcaacactg ttttttgtgcg tcatctgcat   4020
tgatgcatgc agttgtcctt tatttgttct cactgctgga tagtatctgg ttgggtaaat    4080
atatcacact gtaaatcaca ctatccaggt tcctttaggt gacatttggt tgattgcagt    4140
gttctgttgt tacgatggtg ctgctgtgac tgttcttgtg catggacaga agttcctttc    4200
aggtgaattt ctcagaatgg aattgctggg caaaggggca gccaataatc aactcatttg    4260
atgccaaaag tggtggtgcc agttcatcct cccctgcgag gtatgggtcc tgattcactc    4320
ttcaagtgct gtggtttgac agggccgggg gtgacaaggg gacacctggg aaggaaagct    4380
gggctccctg ctggccatcc aggccagtcc ttaccagggg gtaggcaatg attgggtcaa    4440
gtggttcctg accactgggc ctgagacttc aggcccagaa actatctaat atttcctcaa    4500
atgcatccca tgagcaggca ctgtgtgagt gagcacacac atctgaagcc tcaagctagg    4560
caagcctacc atgacttgtg gtccaagggc tcacgggtga cctggagtta gagggagaca    4620
tggctgccag gtggctttag aaagaacact catcatggcc aggtgcggtg gcttacgcct    4680
gtaatcccag cactttggga ggccaaggtg ggtggatcat gaggtcagga gtgagaccag    4740
cctgaccaac atgctgaaac ctgtctctcc taaaaacaca aaaattagct gggcatggag    4800
gtgcacgcct gtaatcccag ctactcagga ggctgaggca ggagaatcac ttgaacccgg    4860
gaggcggagg ttgcaataag cctagattgt gccactgcat tccagcctgg gcaacagagc    4920
aagactccgt ctcagaaaaa aaaaaaaaa ggaagaacac tcatcctatg accttgacct     4980
ccaagctttg cctccctcaa gcagaacaga atggagcctc ccttaggcag aggcggaagt    5040
ttgcctctca cctagttctc cattcttttg ttcagagcct gaatacccte aggctctgta    5100
cttggggtat ttctgttctc ttgttttatg ctcacggttg tgaggtttgt tgtgagtacc    5160
acgatccctt ccttcagagg agtaaactga ggttccaaaa ggtttagcag ttgcccgagg    5220
aatattaaat tggcaaaagc aggtagaata taaagcaagg agtatttggc aacggttctt    5280
ttttatgatt aaaaacagcc gaagaaagac ttctacttgt gcctttgaag gagtaactgc    5340
atttgacctt cccaccagta acaaccatca aatctctatt aaattaaaca cacacacaca    5400
caaacaaaaa cagctattgt gaaggtatca gcgactaaga caactaaggt ttgaggggcc    5460
aggatcctgg agagatggaa acttccctga ggtgagcccc acattctcag acactttcc    5520
ttggatgttt tgagcactgc tttaattcct gggaaaacaa ttccttccac tgtgcacaga    5580
ctctggggcc agacagcttg ggttcaatcc cagctctgcc acttaatgtc tgtgtatctg    5640
tgtaggcaag ttaccctttg gtgcgtcagt ttcctcatct gtaaaacaca actatagttg    5700
atcctcattc gttaagagtc tgtacttgtt aatttgctca cttgctaaaa tttgttaccc    5760
caaaatcagt accectagcc ttttggggtc gtttcaaaga tgtgtgcaga gcggcaaaaa    5820
aatgtgagct cctccaggct catgttccca gccaaggtcc aacaaagtgc tgccctgcct    5880
```

```
tcttatttca gctgtcatag tgtaaactgt gtccttttca cagtctgatt agtgccatgt    5940
ttttcagatt tttatgcttt tttcttggtt atttctctgt taaaattgtc tccaagtgta    6000
gtgcaaagtt tagcacgagg aggctgtgat gttccttaca gagaaaatgc atgtgttaga    6060
gaagctttgt caggcatgag ttaaggtgct gttgtcctga gatcaattaa tttgttgttg    6120
ttgttgtttg agacagggtc tccctctgtt gcccaggctg ctggagtgca atggtgtaat    6180
catagctcac tgcagcctct acctctctgg ctcaagcaat cctcccacct cggcctcctg    6240
agtagctggg actacaggta caccccacca cacccagata atgttttga tattttttta    6300 ggtggaattt tgctcatcac ccaggctgga gtgcaatggt gcgatcctgg ctcactgcaa    6360
cctccacctc ccggattcaa gcaattcttc tgcctcagcc tcctgagtag cacagattac    6420
aggcacatgt catcacgcct tgctaatttt tgtgttttta gtagaggcgg ggtttcacca    6480
tgttggccag gctagtcttg aactcctgac ctcaggtgat ccacccgcct ccgcctccca    6540
aactgcagag attataggca cgaaccacaa tgcccggcct catgttttt attttcaag    6600 ttgaaatgag gtctctctat gttgcccagg ttggtctcaa actcttgagc tcaagtaatc    6660
ctcccacctt ggcctcccaa agtgcgggga ttacaggtgt gagctaccat gcccagccaa    6720
gatcagtgtt aatgaatcaa ctatatatat tacataaggt gtctttaaac agaaataagg    6780
ttatatattg atcgattggt aacaatgttg tgaccagcag cttacagggt acctagcctt    6840
gtatttctcc tataaataat ttgctcgttg agtgtttgtg gcaactttgt agcacataac    6900
taccaagaat aaggactgta ataagagtac gtccctcaca ggattgtaat gaagactgag    6960
tccatttaca taaaggctga gagcagtgtc aagcagatgg agaacactgt agaatgtgcg    7020
atagctctaa cagtggttat catggctgcc ctctcacttc ttcagagaca tgtgtttcta    7080
aggtctgcac tctgccccac cctccccatc cactgtcccc cagcccgttt cctcctccac    7140
ttacttccca gccctgtgcc ttctgccttc tcttttctga gtttgctaag ggcactgctg    7200
gctcaagagc agtaactaac agtctctcgc ctcttctctc catggcaacc agtgacctt    7260 ggagaatgta aaccttatca ccaatctctt aaagcccttc ggtgccttcc caggatgacg    7320
tccagctgag gtccttggca agacccaggg cgccccctcc tcgctccatc acctcccctg    7380
tcacctcccc tgcatctccc tactccagct gcaccactct tgtgcccag tggctcttgt    7440 ctgattattt ccttcatctc cccagctggt cagcagagct ggtggtaatc aactcagacc    7500
ctgtcacctg gatgtccagc agttagggac taaaaaaaat caacaggtca cattctgtcc    7560
tgcagatcat gataataaga tctgtcagac agcagtcagc agtcagagcc aaatcttctg    7620
gacttcagca ggattctgcc tcttgctatt tcctgttgcc tctcttagtg accttttaag    7680
agcattgtgg atgcctccca gcctcctgct aaccaccctg taacctgaac agcctgcagc    7740
agccctgccc agtagaactt cctgatgtga tggaaatgct gtgtctgcac cactagccac    7800
atgtggccac aggattctcg aaactggtgg tgcagttgag gagctgactt tatatttat    7860 ctcattaaat ttaaatgtaa atagctacgt gtggcttgtt ggctagccta ttggaaaaca    7920
cgggcttaga gagacacagg gagaatcact gtaatgcact aaaagaaggt aaaaaaaaa    7980 aaatcctaag aaatattcct aaaatacttt aatatagggc tgggtgcggt ggctcacatc    8040
cagcattttg ggaagctgag gagggcagat cacttgaggc caggagttca agaccagcct    8100
ggccaacatg gtgaaacccc gtctctacta aaaatacaaa aaatcgggtg cggtggcggg    8160
tgcctgtaat cccagctacg cgggaggctg aggcacgaga atcactcgaa cccgggaggc    8220
```

| | |
|---|---:|
| ggggggttgca gtgagccgag atcgtgccac tgcactccag cctgggcgac agagcgagac | 8280 |
| ttcatctcaa aaacaaaaaa caaaaaccaa aaaaaaaaac ttcagcatga ttatttaacc | 8340 |
| aaaatgcagg ttagttgttc accggatgca gagtccaatt aacaagagca aggcctggta | 8400 |
| ccaaaaaaag tgaatttact ccgaaactag cttgggtgag gggtacaaag catcctgcct | 8460 |
| ttctttaaaa gtgctgcttc cccttggaag tagaaagtgg acactttat aaggtaaggg | 8520 |
| gggaagtgtg caagggcaag tgggggggtc cctctgctag ttccgtgcat actctacagg | 8580 |
| acagttgact tggcaccttc ctggttagta ataagctgta gcagtggcca agtgggcatg | 8640 |
| cttTcagtat gccctcccag tgaatgaaag tcctgaggca accccaagg gtggaagtgc | 8700 |
| caggccacca cccactggag gtgaaagttc cgtgatgggt ttgctttggt ctgcgaatct | 8760 |
| actgtcatgt ggagagatct gtgctctgga agagcataca gttagaaaag cttgccctga | 8820 |
| agggaatgta tggtgaaggg gaggtgaaag gttatatttg catttctgaa gggctaagta | 8880 |
| ggaaaccggg aaccagggga gaggagaaga gaagagagga taattttttt taagaaaagc | 8940 |
| aacatattcc cttttcttta gaaaaatgg agcactcggt tacaggcact cgaatgtaga | 9000 |
| agtagcaata tataaattat gcattaatgg gttataattc actgaaaaat agtaacgtac | 9060 |
| ttcttaactt tggctttcag agttcgaacc aacgtggcct caaccagatt tggaatgtca | 9120 |
| aaaagcagag tgtctatttg atgaatttga ggaaatctgg aactttgggc cacccagg | 9178 |

<210> SEQ ID NO 4
<211> LENGTH: 564
<212> TYPE: DNA
<213> ORGANISM: Homo sapiens

<400> SEQUENCE: 4

| | |
|---|---:|
| cccctttctt cctttggggg gtacaaagaa atatctgacc cagttacgcc acggcttgaa | 60 |
| aggaggaaac ccaaagaatg gctgtgggga tgaggaagat tcctcaaggg gaggacatgg | 120 |
| tatttaatga gggtcttgaa gatgccaagg aagtggtaga gggtgtttca cgaggaggga | 180 |
| accgtctggg caaaggccag gaaggcggaa gggaatccct tcagagtggc tggtacgccg | 240 |
| catgtattag gggagatgaa agaggcaggc cacgtccaag ccatatttgt gttgctctcc | 300 |
| ggagtttgta ctttaggctt gaacttccca cacgtgttat ttggcccaca ttgtgtttga | 360 |
| agaaactttg ggattggttg ccagtgctta aaagttagga cttagaaaat ggatttcctg | 420 |
| gcaggacgcg gtggctcatg cccataatct cagcactttg ggaggcctag gaaggtggat | 480 |
| cacctgaggt ccggagttca agactaacct ggccaacatg gtgaaaccca gtatctacta | 540 |
| aaaaatacaa aaaaaaaaaa aaaa | 564 |

<210> SEQ ID NO 5
<211> LENGTH: 218
<212> TYPE: DNA
<213> ORGANISM: Homo sapiens

<400> SEQUENCE: 5

| | |
|---|---:|
| aggccaggaa ggcggaaggg gatcccttca gagtggctgg tacgccgcat gtattagggg | 60 |
| agatgaaaga ggcaggccac gtccaagcca tatttgtgtt gctctccgga gtttgtactt | 120 |
| taggcttgaa cttcccacac gtgttatttg gcccacattg tgtttgaaga aactttggga | 180 |
| ttggttgcca gtgcttaaaa gttaggactt agaaaatg | 218 |

<210> SEQ ID NO 6
<211> LENGTH: 118

```
<212> TYPE: DNA
<213> ORGANISM: Homo sapiens

<400> SEQUENCE: 6
gtattagggg agatgaaaga ggcaggccac gtccaagcca tatttgtgtt gctctccgga    60
gtttgtactt taggcttgaa cttcccacac gtgttatttg ccccacattg tgtttgaa    118

<210> SEQ ID NO 7
<211> LENGTH: 38
<212> TYPE: DNA
<213> ORGANISM: Homo sapiens

<400> SEQUENCE: 7
tgttgctctc cggagtttgt actttaggct tgaacttc                            38

<210> SEQ ID NO 8
<211> LENGTH: 18
<212> TYPE: DNA
<213> ORGANISM: Homo sapiens

<400> SEQUENCE: 8
gctctccgga gtttgtac                                                  18

<210> SEQ ID NO 9
<211> LENGTH: 218
<212> TYPE: DNA
<213> ORGANISM: Homo sapiens

<400> SEQUENCE: 9
ttcaccccat cactgccctg tcctccctgg aggaatctgc cagcccgaat tctgttcatc    60
gtaccctcct tttcttagag tttgacctcc tctgtatctc ccccaatcca tgtattgctt   120
atatacaagg tattctgctg tatctgttct gctatggctt gccccttttg ttcaacactg   180
tttttgtgcg tcatctgcat tgatgcatgc agttgtcc                           218

<210> SEQ ID NO 10
<211> LENGTH: 118
<212> TYPE: DNA
<213> ORGANISM: Homo sapiens

<400> SEQUENCE: 10
tctgttcatc gtaccctcct tttcttagag tttgacctcc tctgtatctc ccccaatcca    60
tgtattgctt atatacaagg tattctgctg tatctgttct gctatggctt gccccttt    118

<210> SEQ ID NO 11
<211> LENGTH: 24
<212> TYPE: DNA
<213> ORGANISM: Homo sapiens

<400> SEQUENCE: 11
tatctccccc aatccatgta ttgc                                           24

<210> SEQ ID NO 12
<211> LENGTH: 18
<212> TYPE: DNA
<213> ORGANISM: Homo sapiens

<400> SEQUENCE: 12
ccccaatcca tgtattgc                                                  18

<210> SEQ ID NO 13
```

```
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
guacaaacuc cggagagc                                                 18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
gcaauacatg gattgggg                                                 18

<210> SEQ ID NO 15
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gcaauacaug gauugggg                                                 18

<210> SEQ ID NO 16
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
aaguacaaac uccggagagc                                               20

<210> SEQ ID NO 17
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
guacaaacuc cggagagcaa                                               20

<210> SEQ ID NO 18
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
aguacaaacu ccggagagca                                               20
```

```
<210> SEQ ID NO 19
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
acaaacuccg gagagcaa                                                 18

<210> SEQ ID NO 20
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
aaacuccgga gagcaaca                                                 18

<210> SEQ ID NO 21
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
acuccggaga gcaacaca                                                 18

<210> SEQ ID NO 22
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uccggagagc aacacaaa                                                 18

<210> SEQ ID NO 23
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cggagagcaa cacaaaua                                                 18

<210> SEQ ID NO 24
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gagagcaaca caaauaug                                                 18
```

-continued

```
<210> SEQ ID NO 25
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gagcaacaca aauauggc                                                        18

<210> SEQ ID NO 26
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gcaacacaaa uauggcuu                                                        18

<210> SEQ ID NO 27
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
aaguacaaac uccggaga                                                        18

<210> SEQ ID NO 28
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
uaaaguacaa acuccgga                                                        18

<210> SEQ ID NO 29
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ccuaaaguac aaacuccg                                                        18

<210> SEQ ID NO 30
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
agccuaaagu acaaacuc                                                        18

<210> SEQ ID NO 31
```

```
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
caagccuaaa guacaaac                                                 18

<210> SEQ ID NO 32
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uucaagccua aaguacaa                                                 18

<210> SEQ ID NO 33
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
aguucaagcc uaaaguac                                                 18

<210> SEQ ID NO 34
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gaaguucaag ccuaaagu                                                 18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
aauacatgga ttggggga                                                 18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
```
uacatggatt gggggaga                                               18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
catggattgg gggagaua                                               18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
tggattgggg gagauaca                                               18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
gattggggga gauacaga                                               18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
ttgggggaga uacagagg                                               18

<210> SEQ ID NO 41
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gggggagaua cagaggag                                               18

```
<210> SEQ ID NO 42
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gggagauaca gaggaggu                                                     18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
gcaauacatg gattgggg                                                     18

<210> SEQ ID NO 44
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gcaauacaug gauugggg                                                     18

<210> SEQ ID NO 45
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
guacaaacuc cggagagc                                                     18

<210> SEQ ID NO 46
<211> LENGTH: 600
<212> TYPE: DNA
<213> ORGANISM: Homo sapiens

<400> SEQUENCE: 46
gaagaagaag aagaagaaga agaagaagaa gaagaagaag aagaagaaga agaagaagaa       60
gaagaagaag aagaagaaga agaagaagaa gaagaagaag aagaagaaga agaagaagaa      120
gaagaagaag aagaagaaga agaagaagaa gaagaagaag aagaagaaga agaagaagaa      180
gaagaagaag aagaagaaga agaagaagaa gaagaagaag aagaagaaga agaagaagaa      240
gaagaagaag aagaagaaga agaagaagaa gaagaagaag aagaagaaga agaagaagaa      300
gaagaagaag aagaagaaga agaagaagaa gaagaagaag aagaagaaga agaagaagaa      360
gaagaagaag aagaagaaga agaagaagaa gaagaagaag aagaagaaga agaagaagaa      420
gaagaagaag aagaagaaga agaagaagaa gaagaagaag aagaagaaga agaagaagaa      480
```

```
gaagaagaag aagaagaaga agaagaagaa gaagaagaag aagaagaaga agaagaagaa        540
gaagaagaag aagaagaaga agaagaagaa gaagaagaag aagaagaaga agaagaagaa        600

<210> SEQ ID NO 47
<211> LENGTH: 18
<212> TYPE: DNA
<213> ORGANISM: Homo sapiens

<400> SEQUENCE: 47
gaagaagaag aagaagaa                                                      18

<210> SEQ ID NO 48
<211> LENGTH: 570
<212> TYPE: DNA
<213> ORGANISM: Homo sapiens
<220> FEATURE:
<221> NAME/KEY: misc_feature
<222> LOCATION: (1)..(570)
<223> OTHER INFORMATION: This sequence may encompass 90-190 "gaa"
      repeating units

<400> SEQUENCE: 48
gaagaagaag aagaagaaga agaagaagaa gaagaagaag aagaagaaga agaagaagaa         60
gaagaagaag aagaagaaga agaagaagaa gaagaagaag aagaagaaga agaagaagaa        120
gaagaagaag aagaagaaga agaagaagaa gaagaagaag aagaagaaga agaagaagaa        180
gaagaagaag aagaagaaga agaagaagaa gaagaagaag aagaagaaga agaagaagaa        240
gaagaagaag aagaagaaga agaagaagaa gaagaagaag aagaagaaga agaagaagaa        300
gaagaagaag aagaagaaga agaagaagaa gaagaagaag aagaagaaga agaagaagaa        360
gaagaagaag aagaagaaga agaagaagaa gaagaagaag aagaagaaga agaagaagaa        420
gaagaagaag aagaagaaga agaagaagaa gaagaagaag aagaagaaga agaagaagaa        480
gaagaagaag aagaagaaga agaagaagaa gaagaagaag aagaagaaga agaagaagaa        540
gaagaagaag aagaagaaga agaagaagaa                                         570
```

OLIGONUCLEOTIDES TARGETING FRATAXIN AND RELATED METHODS

CROSS-REFERENCE TO RELATED APPLICATIONS

This application claims the benefit of U.S. Provisional Application Ser. No. 62/976,647, filed Feb. 14, 2020, the entire disclosure of which is incorporated herein by reference.

BACKGROUND

Friedreich's ataxia (FRDA) is caused by a deficiency of frataxin (FXN) expression and there are about 6,500 FRDA patients living with poor life quality and shortened life span (average 40-50 years) without any available cure in the United States now (Doğan-Aslan, M. et al. Turkish J. Phys. Med. Rehabil. 64, 230-238. 2018). About 96% of FRDA cases are caused by a GAA repeat expansion in intron 1 of both alleles of FXN (Clark, E. et al. Neuronal Signal. 2 (4): NS20180060. 2018). Studies have shown that antisense oligonucleotides (ASOs) targeting the transcript within the GAA repeat region can restore FXN expression (Li, L. et al. Nat. Commun. 7, 1-8. 2016; Shen, X. et al. RNA. doi: 10.1261/rna.071290.119. 2019). However, the risks of off-target events of the GAA-repeat-targeting ASOs have hindered their potential as a drug to treat FRDA. Accordingly, there exists a need to effectively increase protein expression of frataxin while minimizing off-target interactions.

SUMMARY

In one aspect, the disclosure provides an antisense oligonucleotide comprising a region of complementarity (e.g., an antisense oligonucleotide comprising complementarity) to an intron of a FXN transcript, wherein the antisense oligonucleotide does not comprise a region of complementarity (e.g., the antisense oligonucleotide comprising complementarity) to another site in a human genome.

In another aspect, the disclosure provides an antisense oligonucleotide comprising a region of complementarity to intron 1 of a FXN transcript, wherein the antisense oligonucleotide does not comprise a region of complementarity to another site in a human genome. In certain embodiments, the antisense oligonucleotide does not comprise complementarity to another site in the human genome over at least 14 contiguous nucleotides of the antisense oligonucleotide. In certain embodiments, the antisense oligonucleotide does not comprise complementarity to another site in the human genome over 14 contiguous nucleotides, 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the antisense oligonucleotide. In certain embodiments, the antisense oligonucleotide does not comprise complementarity to another site in the human genome over the full length of the antisense oligonucleotide. In certain embodiments, the antisense oligonucleotide comprises a region of complementarity to SEQ ID NO: 1.

In one aspect, the disclosure provides an antisense oligonucleotide comprising a region of complementarity upstream of a trinucleotide repeat of a FXN transcript, wherein:
the region of complementarity is within intron 1 of the FXN transcript; and
the antisense oligonucleotide does not comprise a region of complementarity to another site in a human genome.
In certain embodiments, the antisense oligonucleotide does not comprise full complementarity to another site in the human genome.

In certain embodiments, the antisense oligonucleotide comprises a region of complementarity to SEQ ID NO: 2. In certain embodiments, the antisense oligonucleotide comprises a region of complementarity to SEQ ID NO: 4. In certain embodiments, the antisense oligonucleotide comprises a region of complementarity to SEQ ID NO: 5. In certain embodiments, the antisense oligonucleotide comprises a region of complementarity to SEQ ID NO: 6. In certain embodiments, the antisense oligonucleotide comprises a region of complementarity to SEQ ID NO: 7. In certain embodiments, the antisense oligonucleotide comprises a region of complementarity to SEQ ID NO: 8.

In one aspect, the disclosure provides an antisense oligonucleotide comprising a region of complementarity downstream of a trinucleotide repeat of a FXN transcript, wherein the region of complementarity is within intron 1 of the FXN transcript.

In certain embodiments, the antisense oligonucleotide comprises a region of complementarity to SEQ ID NO: 3. In certain embodiments, the antisense oligonucleotide comprises a region of complementarity to SEQ ID NO: 9. In certain embodiments, the antisense oligonucleotide comprises a region of complementarity to SEQ ID NO: 10. In certain embodiments, the antisense oligonucleotide comprises a region of complementarity to SEQ ID NO: 11. In certain embodiments, the antisense oligonucleotide comprises a region of complementarity to SEQ ID NO: 12.

In one aspect, the disclosure provides an antisense oligonucleotide comprising a region of complementarity to a purine-rich sequence within intron 1 of a FXN transcript. In certain embodiments, the purine-rich sequence comprises greater than 50% purine nucleotides. In certain embodiments, the purine-rich sequence comprises between about 51% to about 60% purine nucleotides.

In one aspect, the disclosure provides an antisense oligonucleotide comprising a region of complementarity to a FXN sequence of SEQ ID NO:8 or SEQ ID NO: 12.

In certain embodiments, the antisense oligonucleotide is fully complementary to the FXN transcript.

In certain embodiments, the antisense oligonucleotide is between 8 nucleotides to 80 nucleotides in length. In certain embodiments, the antisense oligonucleotide is between 10 nucleotides to 30 nucleotides in length. In certain embodiments, the antisense oligonucleotide is between 12 nucleotides to 30 nucleotides in length. In certain embodiments, the antisense oligonucleotide is 12, 13, 14, 15, 16, 17, 18, 19, 20, 21, 22, 23, 24, 25, 26, 27, 28, 29, or 30 nucleotides in length.

In certain embodiments, the antisense oligonucleotide comprises one or more modified nucleotides. In certain embodiments, the one or more modified nucleotides each independently comprise a modification of a ribose group, a phosphate group, a nucleobase, or a combination thereof.

In certain embodiments, each modification of the ribose group comprises 2'-O-methyl, 2'-fluoro, 2'-deoxy, 2'-O-(2-methoxyethyl) (MOE), 2'-O-alkyl, 2'-O-alkoxy, 2'-O-alkylamino, 2'-NH$_2$, a constrained nucleotide, or a combination thereof.

In certain embodiments, the constrained nucleotide comprises a locked nucleic acid (LNA), an ethyl-constrained nucleotide, a 2'-(S)-constrained ethyl (S-cEt) nucleotide, a constrained MOE, a 2'-0,4'-C-aminomethylene bridged nucleic acid (2',4'-BNA$^{NC}$), an alpha-L-locked nucleic acid, and a tricyclo-DNA, or a combination thereof.

In certain embodiments, the modification of the ribose group comprises a 2'-O-(2-methoxyethyl) (MOE) modification. In certain embodiments, every nucleotide of the antisense oligonucleotide comprises a 2'-O-(2-methoxyethyl) (MOE) modification.

In certain embodiments, the modification of the ribose group comprises a tricyclo-DNA modification. In certain embodiments, every nucleotide of the antisense oligonucleotide comprises a tricyclo-DNA modification.

In certain embodiments, the modification of the ribose group comprises a 2'-deoxy modification.

In certain embodiments, each modification of the phosphate group comprises a phosphorothioate, a phosphonoacetate (PACE), a thiophosphonoacetate (thioPACE), an amide, a triazole, a phosphonate, a phosphotriester, or a combination thereof.

In certain embodiments, the modification of the phosphate group comprises a phosphorothioate modification. In certain embodiments, every nucleotide of the antisense oligonucleotide comprises a phosphorothioate modification. In certain embodiments, at least one nucleotide of the antisense oligonucleotide comprises a phosphorodiamidate morpholino (PMO) nucleotide. In certain embodiments, every nucleotide of the antisense oligonucleotide comprises a phosphorodiamidate morpholino (PMO) nucleotide.

In certain embodiments, each modification of the nucleobase comprises 2-thiouridine, 4-thiouridine, N$^6$-methyladenosine, pseudouridine, 2,6-diaminopurine, inosine, thymidine, 5-methylcytosine, 5-substituted pyrimidine, isoguanine, isocytosine, halogenated aromatic groups, or a combination thereof.

In certain embodiments, the modification of the nucleobase group comprises a 5-methylcytosine modification.

In certain embodiments, the antisense oligonucleotide comprises a mixture of modified nucleotides.

In certain embodiments, the mixture of modified nucleotides comprises two or more modifications selected from the group consisting of: 2'-O-methyl, 2'-deoxy, 2'-O-(2-methoxyethyl) (MOE), LNA, and tricyclo-DNA.

In certain embodiments, the antisense oligonucleotide comprises 4 or fewer consecutive 2'-deoxy modified nucleotides.

In certain embodiments, the mixture of modified nucleotides comprises one or more 2'-O-methyl modified nucleotides and one or more LNA modified nucleotides.

In certain embodiments, the mixture of modified nucleotides comprises one or more 2'-O-(2-methoxyethyl) (MOE) modified nucleotides and one or more LNA modified nucleotides.

In certain embodiments, the mixture of modified nucleotides comprises one or more 2'-O-(2-methoxyethyl) (MOE) modified nucleotides and one or more tricyclo-DNA modified nucleotides.

In certain embodiments, the mixture of modified nucleotides comprises one or more 2'-deoxy modified nucleotides and one or more LNA modified nucleotides.

In certain embodiments, the antisense oligonucleotide comprises the formula:

A-B-C, wherein:

A comprises from about 0 to about 8 modified nucleotides;

B comprises from about 6 to about 18 deoxyribonucleic acid (DNA) nucleotides and/or DNA-like nucleotides; and C comprises from about 0 to about 8 modified nucleotides;

and wherein the overall length of the antisense oligonucleotide is about 12 to about 30 nucleotides.

In certain embodiments, A comprises from about 2 to about 6 modified nucleotides, B comprises from about 6 to about 12 DNA nucleotides and/or DNA-like nucleotides, and C comprises from about 2 to about 6 modified nucleotides.

In certain embodiments, A comprises about 5 modified nucleotides, B comprises about 9 DNA nucleotides and/or DNA-like nucleotides, and C comprises about 4 modified nucleotides.

In certain embodiments, A comprises from about 2 to about 6 2'-O-(2-methoxyethyl) (MOE) modified nucleotides, B comprises from about 6 to about 12 DNA-like nucleotides, and C comprises from about 2 to about 6 2'-O-(2-methoxyethyl) (MOE) modified nucleotides.

In certain embodiments, A comprises about 5 2'-O-(2-methoxyethyl) (MOE) modified nucleotides, B comprises about 9 DNA-like nucleotides, and C comprises about 4 2'-O-(2-methoxyethyl) (MOE) modified nucleotides.

In certain embodiments, the antisense oligonucleotide comprises the formula:

A-B-C, wherein:

A comprises from about 0 to about 18 modified nucleotides;

B comprises from about 0 to about 4 deoxyribonucleic acid (DNA) nucleotides and/or DNA-like nucleotides; and C comprises from about 0 to about 18 modified nucleotides;

and the overall length of the antisense oligonucleotide is about 10 to about 30 nucleotides.

In certain embodiments, the antisense oligonucleotide comprises a nucleic acid sequence with at least 90% sequence identity to the nucleic acid sequence set forth in any one of SEQ ID NOs: 13, 14, or 15 (SEQ ID NO: 13—GUACAAACUCCGGAGAGC), (SEQ ID NO: 14—GCAAUACATGGATTGGGG), (SEQ ID NO: 15—GCAAUACAUGGAUUGGGG).

In certain embodiments, the antisense oligonucleotide comprises a nucleic acid sequence with at least 90% sequence identity (i.e., 90%, 91%, 92%, 93%, 94%, 95%, 96%, 97%, 98%, 99%, or 100% sequence identity) to the nucleic acid sequence set forth in SEQ ID NO: 13. In certain embodiments, the antisense oligonucleotide comprises a nucleic acid sequence set forth in SEQ ID NO: 13.

In certain embodiments, the antisense oligonucleotide comprises a nucleic acid sequence with at least 90% sequence identity (i.e., 90%, 91%, 92%, 93%, 94%, 95%, 96%, 97%, 98%, 99%, or 100% sequence identity) to the nucleic acid sequence set forth in SEQ ID NO: 14. In certain embodiments, the antisense oligonucleotide comprises a nucleic acid sequence set forth in SEQ ID NO: 14.

In certain embodiments, the antisense oligonucleotide comprises a nucleic acid sequence with at least 90% sequence identity (i.e., 90%, 91%, 92%, 93%, 94%, 95%, 96%, 97%, 98%, 99%, or 100% sequence identity) to the nucleic acid sequence set forth in SEQ ID NO: 15. In certain embodiments, the antisense oligonucleotide comprises a nucleic acid sequence set forth in SEQ ID NO: 15.

In certain embodiments, the antisense oligonucleotide comprises a nucleic acid sequence with at least 90% sequence identity (i.e., 90%, 91%, 92%, 93%, 94%, 95%, 96%, 97%, 98%, 99%, or 100% sequence identity) to the nucleic acid sequence set forth in any one of SEQ ID NOs: 16-42 (i.e., SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

In certain embodiments, the antisense oligonucleotide comprises a nucleic acid sequence set forth in any one of SEQ ID NOs: 16-42 (i.e., SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

In certain embodiments, the antisense oligonucleotide comprises a sequence modification pattern of $[\underline{X}s]_a[Xs]_b[s\underline{X}]_c$, wherein:

a represents an integer between 0-8;
b represents an integer between 6-18;
c represents an integer between 0-8;
s represents a phosphorothioate internucleoside linkage;
$\underline{X}$ is an adenosine, a guanosine, a cytidine, a thymine, or a uracil, wherein $\underline{X}$ comprises a 2'-O-(2-methoxyethyl) modification or a tricyclo-DNA modification;
X is an adenosine, a guanosine, a cytidine, a thymine, or a uracil, wherein X comprises a 2'-deoxy modification; and
wherein the sum of a, b, and c is greater than or equal to 12.

In certain embodiments, the antisense oligonucleotide comprises a sequence modification pattern of $Xs\underline{X}sXs\underline{X}sXsXsXsXsXsXsXsXsXs\underline{X}s\underline{X}sXs\underline{X}$, wherein:

s represents a phosphorothioate internucleoside linkage;
$\underline{X}$ is an adenosine, a guanosine, a cytidine, a thymine, or a uracil, wherein $\underline{X}$ comprises a 2'-O-(2-methoxyethyl) modification or a tricyclo-DNA modification; and
X is an adenosine, a guanosine, a cytidine, a thymine, or a uracil, wherein X comprises a 2'-deoxy modification.

In certain embodiments, the antisense oligonucleotide comprises a sequence modification pattern of $Xs\underline{X}s\underline{X}sXs\underline{X}sXsXsXsXsXsXsXsXs\underline{X}s\underline{X}s\underline{X}sX$, wherein:

s represents a phosphorothioate internucleoside linkage;
$\underline{X}$ is an adenosine, a guanosine, a cytidine, a thymine, or a uracil, wherein $\underline{X}$ comprises a 2'-O-(2-methoxyethyl) modification; and
X is an adenosine, a guanosine, a cytidine, a thymine, or a uracil, wherein X comprises a 2'-deoxy modification.

In certain embodiments, the antisense oligonucleotide comprises a sequence modification pattern of $[\underline{X}s]_d[s\underline{X}]_e$, wherein:

d represents an integer between 0-40;
e represents an integer between 0-40;
s represents a phosphorothioate internucleoside linkage;
$\underline{X}$ is an adenosine, a guanosine, a cytidine, a thymine, or a uracil, wherein $\underline{X}$ comprises a 2'-O-(2-methoxyethyl) modification or a tricyclo-DNA modification; and
wherein the sum of d and e is greater than or equal to 10.

In certain embodiments, the antisense oligonucleotide comprises a sequence modification pattern of $\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}$, wherein:

s represents a phosphorothioate internucleoside linkage; and
$\underline{X}$ is an adenosine, a guanosine, a cytidine, a thymine, or a uracil, wherein $\underline{X}$ comprises a 2'-O-(2-methoxyethyl) modification or a tricyclo-DNA modification.

In certain embodiments, the antisense oligonucleotide comprises a sequence modification pattern of $\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}$, wherein:

s represents a phosphorothioate internucleoside linkage; and
$\underline{X}$ is an adenosine, a guanosine, a cytidine, a thymine, or a uracil, wherein $\underline{X}$ comprises a 2'-O-(2-methoxyethyl) modification.

In certain embodiments, each cytosine is a 5-methylcytosine.

In one aspect, the disclosure provides an antisense oligonucleotide comprising the sequence $\underline{G}s\underline{C}s\underline{A}s\underline{A}s\underline{U}s\underline{A}s\underline{C}s\underline{A}sTsGsGsAsTsTsGsGsGsG$, wherein:

s represents a phosphorothioate internucleoside linkage;
$\underline{A}$ is an adenosine comprising a 2'-O-(2-methoxyethyl) modification;
$\underline{G}$ is a guanosine comprising a 2'-O-(2-methoxyethyl) modification;
$\underline{C}$ is a cytidine comprising a 2'-O-(2-methoxyethyl) modification;
$\underline{U}$ is a thymine comprising a 2'-O-(2-methoxyethyl) modification;
A is an adenosine comprising a 2'-deoxy modification;
G is a guanosine comprising a 2'-deoxy modification;
C is a cytidine comprising a 2'-deoxy modification; and
T is a thymine comprising a 2'-deoxy modification.

In another aspect, the disclosure provides an antisense oligonucleotide comprising the sequence $\underline{G}s\underline{C}s\underline{A}s\underline{A}s\underline{U}s\underline{A}s\underline{C}s\underline{A}s\underline{U}s\underline{G}s\underline{G}s\underline{A}s\underline{U}s\underline{U}s\underline{G}s\underline{G}s\underline{G}s\underline{G}$, wherein:

s represents a phosphorothioate internucleoside linkage;
$\underline{A}$ is an adenosine comprising a 2'-O-(2-methoxyethyl) modification;
$\underline{G}$ is a guanosine comprising a 2'-O-(2-methoxyethyl) modification;
$\underline{C}$ is a cytidine comprising a 2'-O-(2-methoxyethyl) modification; and
$\underline{U}$ is a thymine comprising a 2'-O-(2-methoxyethyl) modification.

In yet another aspect, the disclosure provides an antisense oligonucleotide comprising the sequence $\underline{G}s\underline{U}s\underline{A}s\underline{C}s\underline{A}s\underline{A}s\underline{A}s\underline{C}s\underline{U}s\underline{C}s\underline{C}s\underline{G}s\underline{G}s\underline{A}s\underline{G}s\underline{A}s\underline{G}s\underline{C}$, wherein:

s represents a phosphorothioate internucleoside linkage;
$\underline{A}$ is an adenosine comprising a 2'-O-(2-methoxyethyl) modification;
$\underline{G}$ is a guanosine comprising a 2'-O-(2-methoxyethyl) modification;

C is a cytidine comprising a 2'-O-(2-methoxyethyl) modification; and

U is a thymine comprising a 2'-O-(2-methoxyethyl) modification.

In certain embodiments, the antisense oligonucleotide is conjugated to a ligand. In certain embodiments, the ligand directs uptake in skeletal muscle, cardiac muscle, and/or pancreatic beta cells. In certain embodiments, the ligand comprises a carbohydrate, a phospholipid, an antibody, a peptide, and/or a hydrophobic moiety.

In one aspect, the disclosure provides a combination comprising one or more antisense oligonucleotides comprising a region of complementarity to a FXN transcript sequence of SEQ ID NO: 2 or 4-8, and one or more antisense oligonucleotides comprising a region of complementarity to a FXN transcript sequence of SEQ ID NO: 3 or 9-12.

In certain embodiments, the antisense oligonucleotides are between 8 nucleotides to 80 nucleotides in length. In certain embodiments, the antisense oligonucleotides are between 10 nucleotides to 30 nucleotides in length.

In certain embodiments, the antisense oligonucleotide comprises one or more modified nucleotides. In certain embodiments, the one or more modified nucleotides each independently comprise a modification of a ribose group, a phosphate group, a nucleobase, or a combination thereof.

In certain embodiments, each modification of the ribose group comprises 2'-O-methyl, 2'-fluoro, 2'-deoxy, 2'-O-(2-methoxyethyl) (MOE), 2'-O-alkyl, 2'-O-alkoxy, 2'-O-alkylamino, 2'-NH$_2$, a constrained nucleotide, or a combination thereof.

In certain embodiments, the constrained nucleotide comprises a locked nucleic acid (LNA), an ethyl-constrained nucleotide, a 2'-(S)-constrained ethyl (S-cEt) nucleotide, a constrained MOE, a 2'-0,4'-C-aminomethylene bridged nucleic acid (2',4'-BNA$^{NC}$), an alpha-L-locked nucleic acid, a tricyclo-DNA, or a combination thereof.

In certain embodiments, the modification of the ribose group comprises a 2'-O-(2-methoxyethyl) (MOE) modification. In certain embodiments, every nucleotide of the antisense oligonucleotide comprises a 2'-O-(2-methoxyethyl) (MOE) modification.

In certain embodiments, the modification of the ribose group comprises a tricyclo-DNA modification. In certain embodiments, every nucleotide of the antisense oligonucleotide comprises a tricyclo-DNA modification.

In certain embodiments, the modification of the ribose group comprises a 2'-deoxy modification.

In certain embodiments, each modification of the phosphate group comprises a phosphorothioate, a phosphonoacetate (PACE), a thiophosphonoacetate (thioPACE), an amide, a triazole, a phosphonate, a phosphotriester modification, or a combination thereof.

In certain embodiments, the modification of the phosphate group comprises a phosphorothioate modification. In certain embodiments, every nucleotide of the antisense oligonucleotide comprises a phosphorothioate modification. In certain embodiments, at least one nucleotide of the antisense oligonucleotide comprises a phosphorodiamidate morpholino (PMO) nucleotide. In certain embodiments, every nucleotide of the antisense oligonucleotide comprises a phosphorodiamidate morpholino (PMO) nucleotide.

In certain embodiments, each modification of the nucleobase group comprises 2-thiouridine, 4-thiouridine, N$^6$-methyladenosine, pseudouridine, 2,6-diaminopurine, inosine, thymidine, 5-methylcytosine, 5-substituted pyrimidine, isoguanine, isocytosine, halogenated aromatic groups, or a combination thereof.

In certain embodiments, the modification of the nucleobase group comprises a 5-methylcytosine modification.

In certain embodiments, one or more antisense oligonucleotides comprise the formula:

A-B-C, wherein:

A comprises from about 0 to about 8 modified nucleotides;

B comprises from about 6 to about 18 deoxyribonucleic acid (DNA) nucleotides and/or DNA-like nucleotides; and C comprises from about 0 to about 8 modified nucleotides;

and wherein the overall length of the antisense oligonucleotide is about 12 to about 30 nucleotides.

In certain embodiments, A comprises from about 2 to about 6 modified nucleotides, B comprises from about 6 to about 12 DNA nucleotides and/or DNA-like nucleotides, and C comprises from about 2 to about 6 modified nucleotides.

In certain embodiments, A comprises about 5 modified nucleotides, B comprises about 9 DNA nucleotides and/or DNA-like nucleotides, and C comprises about 4 modified nucleotides.

In certain embodiments, A comprises from about 2 to about 6 2'-O-(2-methoxyethyl) (MOE) modified nucleotides, B comprises from about 6 to about 12 DNA-like nucleotides, and C comprises from about 2 to about 6 2'-O-(2-methoxyethyl) (MOE) modified nucleotides.

In certain embodiments, A comprises about 5 2'-O-(2-methoxyethyl) (MOE) modified nucleotides, B comprises about 9 DNA-like nucleotides, and C comprises about 4 2'-O-(2-methoxyethyl) (MOE) modified nucleotides.

In certain embodiments, one or more antisense oligonucleotides comprises a nucleic acid sequence with at least 90% sequence identity to the nucleic acid sequence set forth in any one of SEQ ID NOs: 13, 14, or 15 (SEQ ID NO: 13—GUACAAACUCCGGAGAGC), (SEQ ID NO: 14—GCAAUACATGGATTGGGG), (SEQ ID NO: 15—GCAAUACAUGGAUUGGGG).

In certain embodiments, the antisense oligonucleotide comprises a nucleic acid sequence with at least 90% sequence identity (i.e., 90%, 91%, 92%, 93%, 94%, 95%, 96%, 97%, 98%, 99%, or 100% sequence identity) to the nucleic acid sequence set forth in SEQ ID NO: 13. In certain embodiments, the antisense oligonucleotide comprises a nucleic acid sequence set forth in SEQ ID NO: 13.

In certain embodiments, the antisense oligonucleotide comprises a nucleic acid sequence with at least 90% sequence identity (i.e., 90%, 91%, 92%, 93%, 94%, 95%, 96%, 97%, 98%, 99%, or 100% sequence identity) to the nucleic acid sequence set forth in SEQ ID NO: 14. In certain embodiments, the antisense oligonucleotide comprises a nucleic acid sequence set forth in SEQ ID NO: 14.

In certain embodiments, the antisense oligonucleotide comprises a nucleic acid sequence with at least 90% sequence identity (i.e., 90%, 91%, 92%, 93%, 94%, 95%, 96%, 97%, 98%, 99%, or 100% sequence identity) to the nucleic acid sequence set forth in SEQ ID NO: 15. In certain embodiments, the antisense oligonucleotide comprises a nucleic acid sequence set forth in SEQ ID NO: 15.

In certain embodiments, the antisense oligonucleotide comprises a nucleic acid sequence with at least 90% sequence identity (i.e., 90%, 91%, 92%, 93%, 94%, 95%, 96%, 97%, 98%, 99%, or 100% sequence identity) to the nucleic acid sequence set forth in any one of SEQ ID NOs: 16-42 (i.e., SEQ ID NO: 16, SEQ ID NO: 17, SEQ ID NO:

18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

In certain embodiments, the antisense oligonucleotide comprises a nucleic acid sequence set forth in any one of SEQ ID NOs: 16-42 (i.e., SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

In certain embodiments, one or more antisense oligonucleotides comprises a sequence modification pattern of $\underline{X}s\underline{X}s\underline{X}s\underline{X}sXsXsXsXsXsXsXsXsXs\underline{X}s\underline{X}s\underline{X}s\underline{X}$, wherein:

s represents a phosphorothioate internucleoside linkage;

$\underline{X}$ is an adenosine, a guanosine, a cytidine, a thymine, or a uracil, wherein $\underline{X}$ comprises a 2'-O-(2-methoxyethyl) modification; and X is an adenosine, a guanosine, a cytidine, a thymine, or a uracil, wherein X comprises a 2'-deoxy modification.

In certain embodiments, one or more antisense oligonucleotides comprises a sequence modification pattern of $\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}s\underline{X}$, wherein:

s represents a phosphorothioate internucleoside linkage; and $\underline{X}$ is an adenosine, a guanosine, a cytidine, a thymine, or a uracil, wherein $\underline{X}$ comprises a 2'-O-(2-methoxyethyl) modification.

In certain embodiments, each cytosine is a 5-methylcytosine.

In certain embodiments, one or more antisense oligonucleotides are conjugated to a ligand. In certain embodiments, the ligand directs uptake in skeletal muscle, cardiac muscle, and/or pancreatic beta cells. In certain embodiments, the ligand comprises a carbohydrate, a phospholipid, an antibody, a peptide, and/or a hydrophobic moiety.

In certain embodiments, two or more antisense oligonucleotides are linked together through a linker.

In certain embodiments, the linker is a cleavable linker. In certain embodiments, the cleavable linker degrades when cleaved. In certain embodiments, the cleavable linker is a nuclease-cleavable linker comprising a phosphodiester linkage. In certain embodiments, the nuclease-cleavable linker comprises from about 2 to about 8 nucleotides in length. In certain embodiments, the nuclease-cleavable linker comprises about 6 nucleotides. In certain embodiments, the cleavable linker is cleaved under reducing conditions or changing pH conditions. In certain embodiments, the cleavable linker is cleaved by an intracellular or endosomal nuclease. In certain embodiments, the cleavable linker is cleaved by an intracellular or endosomal protease.

In one aspect, the disclosure provides a method for increasing expression of FXN gene in a cell, the method comprising:
(a) introducing into the cell an antisense oligonucleotide recited above; and
(b) maintaining the cell produced in step (a) for a time sufficient to increase expression of the transcript of the FXN gene, or increase expression of the frataxin protein, thereby increasing expression of FXN gene in the cell.

In one aspect, the disclosure provides a method of treating or managing Friedreich's ataxia (FRDA) comprising administering a therapeutically effective amount of the antisense oligonucleotide recited above to a patient in need of such treatment or management.

In certain embodiments, the antisense oligonucleotide is administered to the brain of the patient.

In certain embodiments, the antisense oligonucleotide is administered by intrathecal, intraventricular or intrastriatal injection or infusion. In certain embodiments, the injection or infusion comprises administration using an Ommaya reservoir or intrathecal catheter.

In certain embodiments, the antisense oligonucleotide is administered systemically. In certain embodiments, the antisense oligonucleotide is administered by intravenous, subcutaneous, or intramuscular injection or infusion.

In one aspect, the disclosure provides a method for increasing expression of FXN gene in a cell, the method comprising:
(a) introducing into the cell a combination of antisense oligonucleotides recited above; and
(b) maintaining the cell produced in step (a) for a time sufficient to increase expression of the transcript of the FXN gene, or increase expression of the frataxin protein, thereby increasing expression of FXN gene in the cell.

In one aspect, the disclosure provides a method of treating or managing Friedreich's ataxia (FRDA) comprising administering a therapeutically effective amount of the combination of antisense oligonucleotides recited above to a patient in need of such treatment or management.

In certain embodiments, the combination of antisense oligonucleotides is administered to the brain of the patient.

In certain embodiments, the antisense oligonucleotide is administered by intrathecal, intraventricular or intrastriatal infusion. In certain embodiments, the injection or infusion comprises administration using an Ommaya reservoir or intrathecal catheter.

In certain embodiments, the antisense oligonucleotide is administered systemically. In certain embodiments, the antisense oligonucleotide is administered by intravenous, subcutaneous, or intramuscular injection or infusion.

In certain embodiments, the antisense oligonucleotides are administered sequentially. In certain embodiments, the antisense oligonucleotides are administered simultaneously.

In another aspect, the disclosure provides a method for reducing the growth of a cancer cell, the method comprising: (a) introducing into the cancer cell an antisense oligonucleotide described above; and (b) maintaining the cell produced in step (a) for a time sufficient to increase expression of the transcript of the FXN gene, or increase expression of the frataxin protein, thereby reducing the growth of the cancer cell.

In another aspect, the disclosure provides a method of treating cancer comprising administering a therapeutically effective amount of the antisense oligonucleotide described above to a patient in need of such treatment.

In one aspect, the disclosure provides a method for reducing the growth of a cancer cell, the method comprising: (a) introducing into the cancer cell an antisense oligonucleotide comprising a region of complementarity to an intron of a FXN transcript; and (b) maintaining the cell produced in step (a) for a time sufficient to increase expression of the transcript of the FXN gene, or increase expression of the frataxin protein, thereby reducing the growth of the cancer cell.

In one aspect, the disclosure provides a method of treating cancer comprising administering a therapeutically effective amount of the antisense oligonucleotide comprising a region of complementarity to an intron of a FXN transcript, to a patient in need of such treatment.

In certain embodiments, the antisense oligonucleotide comprises a nucleic acid sequence with at least 90% sequence identity to the nucleic acid sequence set forth in any one of SEQ ID NOs: 13-42.

BRIEF DESCRIPTION OF THE DRAWINGS

FIG. 6A-FIG. 6B depict relative hFXN mRNA expression as measured by a bDNA assay. The antisense oligonucleotide FA48 was used in a steric blocking format and a gapmer format. A 2-nucleotide oligonucleotide walk to the left and right of the FA48 sequence was also performed. For each set of data bars (i.e., FA48-16, FA48-14, etc.), the left bar represents the steric blocking format and the right bar represents the gapmer format (FIG. 6A). Oligonucleotides in the group of FA48 micro-walk and FA48 long oligo groups represent steric blockers derived from FA48. 11631 and 11632 represent steric blockers of FA48 with LNA modifications incorporated. siNTC, NL-15 and mNTC-1 are steric blockers serving as non-target controls. UTC is an untreated control of GM03816 cells (patient derived fibroblasts) (FIG. 6B).

FIG. 7A-FIG. 7C depict relative human FXN (hFXN) mRNA expression as measured by qPCR (FIG. 7A) and a branched DNA (bDNA) assay (FIG. 7B, FIG. 7C). The FA9+FA48 data point corresponds to the combination of the FA9 steric blocker and FA48 gapmer. FIG. 7C depicts the relative human FXN (hFXN) mRNA expression under a series of indicated dosages of treatments as measured by bDNA.

FIG. 8A-FIG. 8D depict relative FXN mRNA expression in GM04078 (patient derived fibroblasts) (FIG. 8A), wild type fibroblasts (FIG. 8B), 293T (FIG. 8C) and U87 cells (FIG. 8D) as measured by a bDNA assay. "FA48SB" corresponds to the antisense oligonucleotide sequence of FA48 in the steric blocking format. mNTC-1, siNTC, and NL-15 serve as non-target controls. BNA2_LNA is a LNA-containing ASO targeting the GAA repeat region in FXN intron 1. UTC indicates untreated controls of indicated cell types. MG2 is an ASO gapmer targeting human MALAT1 as a positive control. Purple bars indicate MALAT1 RNA expression, other columns FXN mRNA expression.

FIG. 9A depicts U87 cells after a 72-hour treatment of indicated oligonucleotides. The left two photos depict cells seeded at 2000 cells per well at the beginning of treatment. The right two photos depict cells seeded at 3000 cells per well at the beginning of treatment. FIG. 9B-FIG. 9C depict relative HPRT-BKD values of indicated treatments normalized by the NL-15 group with the initial cell density of 2000 cells per well (FIG. 9B) and 3000 cells per well (FIG. 9C). SiNTC and NL-15 serve as non-target control. UTC indicates untreated control. MG2 is an ASO gapmer targeting human MALAT1 as a positive control for transfection efficiency.

DETAILED DESCRIPTION

Figure 1:
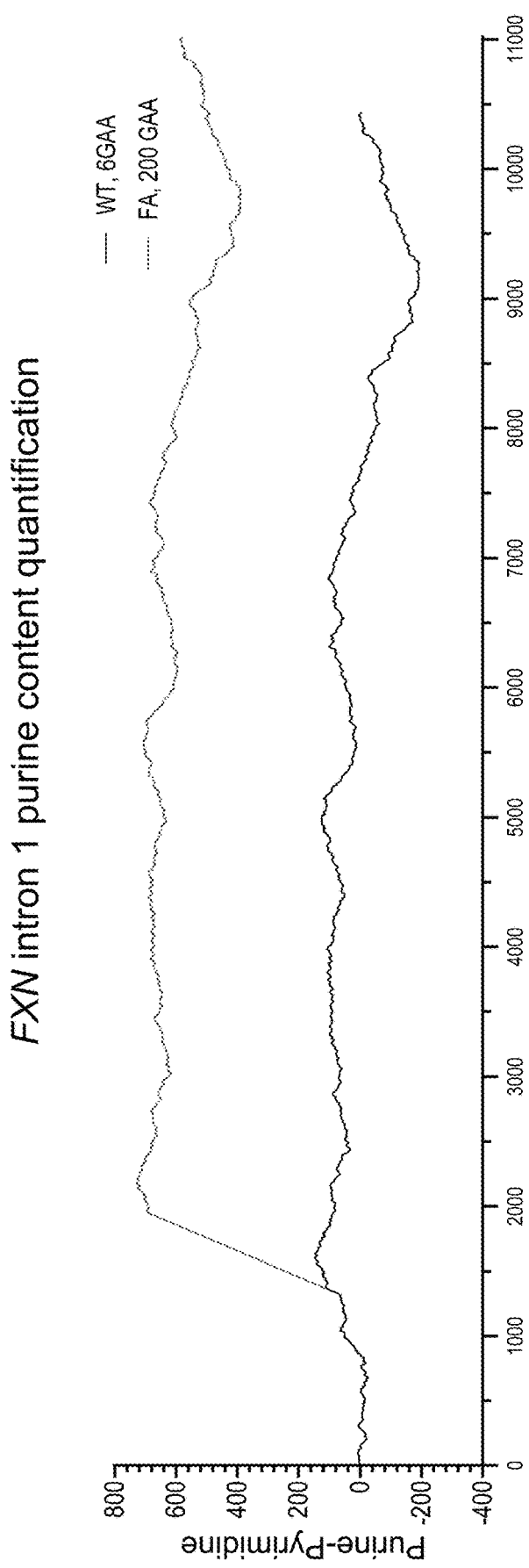
FIG. 1 depicts a schematic of the purine content of FXN intron 1. Boxed regions represent areas of purine rich sequences. Regions with a positive slope represent areas of purine rich sequences. A typical expanded GAA repeat containing 200 copies of the repeat is compared with a typical healthy sequence containing 6 copies of the repeat.

The present disclosure provides antisense compounds, methods, and compositions for increasing frataxin expression. The disclosure described herein is largely based on the finding that certain antisense compounds provide unexpected improvement in increasing frataxin expression, which is useful for the treatment, prevention, or amelioration of diseases, disorders, and conditions associated with the FXN gene in a subject in need thereof. Also contemplated are antisense compounds and methods for the preparation of a medicament for the treatment, prevention, or amelioration of a disease, disorder, or condition associated the FXN gene. FXN-related diseases, disorders, and conditions include, without limitation, neurological diseases and disorders, such as FRDA.

It is to be understood that the methods described in this disclosure are not limited to particular methods and experimental conditions disclosed herein as such methods and conditions can vary. It is also to be understood that the terminology used herein is for the purpose of describing particular embodiments only, and is not intended to be limiting.

Furthermore, the experiments described herein, unless otherwise indicated, can use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, $2^{nd}$ edition).

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein are those well-known and commonly used in the art. The nomenclature used in connection with, and the laboratory procedures and techniques of, analytical chemistry, synthetic organic chemistry, and medicinal and pharmaceutical chemistry described herein are those well-known and commonly used in the art.

So that the disclosure can be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and N(2),N(2)-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). An RNA nucleotide refers to a single ribonucleotide. The term "DNA" or "DNA molecule" or "deoxyribonucleic acid molecule" refers to a polymer of deoxyribonucleotides. A DNA nucleotide refers to a single deoxyribonucleotide. As used herein, the term "DNA-like" refers to a conformation of, e.g. a modified nucleoside or nucleotide which is similar to the conformation of a corresponding unmodified DNA unit. For example, a DNA-like nucleotide can refer to a conformation of a modified deoxyribonucleotide similar to a corresponding unmodified deoxyribonucleotide. Examples of DNA-like nucleotides include, without limitation, e.g., 2'-deoxyribonucleotides, 2'-deoxy-2'-substituted arabinonucleotides (e.g., 2'-deoxy-2'-fluoroarabinonucleotides, also known in the art as 2'F-ANA or FANA), and corresponding phosphorothioate analogs. As used herein, the term "RNA-like" refers to a conformation of, e.g. a modified nucleoside or nucleotide which is similar to the conformation of a corresponding unmodified RNA unit. RNA-like conformations can adopt an A-form helix while DNA-like conformations adopt a B-form helix. Examples of RNA-like nucleotides include, without limitation, e.g., 2'-substituted-RNA nucleotides (e.g., 2'-fluoro-RNA nucleotides also known in the art as 2'F-RNA), locked nucleic acid (LNA) nucleotides (also known in the art as bridged nucleic acids or bicyclic nucleotides), 2'-fluoro-4'-thioarabinonucleotide (also known in the art as 4'S-FANA nucleotides), 2'-O-alkyl-RNA, and corresponding phosphorothioate analogs.

DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. In one embodiment, a siRNA comprises between about 15-30 nucleotides or nucleotide analogs, or between about 16-25 nucleotides (or nucleotide analogs), or between about 18-23 nucleotides (or nucleotide analogs), or between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs can, in some instances, include fewer than 19 nucleotides, e.g., 16, 17 or 18 nucleotides, provided that the shorter siRNA retains the ability to mediate RNAi. Likewise, long siRNAs can, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary modified nucleotides are modified at any position so as to alter certain chemical properties of the nucleotide yet retain the ability of the modified nucleotide to perform its intended function. Examples of positions of the nucleotide which can be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Modified nucleotides also include deaza nucleotides, e.g., 7-deaza-adenosine; O- and N-modified (e.g., alkylated, e.g., N6-methyl adenosine, or as otherwise known in the art)

nucleotides; and other heterocyclically modified nucleotides such as those described in Herdewijn, Antisense Nucleic Acid Drug Dev., 2000 Aug. 10(4):297-310.

Modified nucleotides can also comprise modifications to the sugar portion of the nucleotides. For example, the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. For another example, the ribose sugar can be replaced with a bicyclic or tricylic moiety, such as in Locked Nucleic Acid, constrained ethyl, tricyclo-DNA (tcDNA), or other bridged or bicyclic modifications. Other possible modifications include those described in U.S. Pat. Nos. 5,858,988, and 6,291,438.

The phosphate group of the nucleotide can also be modified, e.g., by substituting one or more of the oxygens of the phosphate group with sulfur (e.g., phosphorothioates), or by making other substitutions which allow the nucleotide to perform its intended function such as described in Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2):77-85, and U.S. Pat. No. 5,684,143. Certain of the above-referenced modifications (e.g., phosphate group modifications) decrease the rate of hydrolysis of polynucleotides comprising said analogs in vivo or in vitro.

As used herein, the terms "unmodified nucleotide" or "non-modified nucleotide" refers to a nucleotide composed of naturally occurring nucleobases, sugar moieties, and internucleoside linkages. In some embodiments, a non-modified nucleotide is an RNA nucleotide (i.e. β-D-ribonucleoside) or a DNA nucleotide (i.e. β-D-deoxyribonucleoside).

The term "oligonucleotide" refers to a short polymer of nucleotides and/or modified nucleotides. As discussed above, the oligonucleotides can be linked with non-phosphodiester linkages, which result in a lower rate of hydrolysis as compared to an oligonucleotide linked with phosphodiester linkages. For example, the nucleotides of the oligonucleotide can comprise triazole, amide, carbamate, methylenediol, ethylene diol, oxymethylthio, oxyethylthio, oxycarbonyloxy, phosphorodiamidate, phosphoroamidate, phosphonate, and/or phosphorothioate linkages. Alterations or modifications of the oligonucleotide can further include addition of non-nucleotide material to the end(s) of the oligonucleotide or internally (at one or more nucleotides of the oligonucleotide).

As used herein, the term "antisense oligonucleotide" refers to an oligonucleotide molecule, which is capable of binding to RNA inside cells by Watson-Crick base pairing. Depending on the sequence and chemistry of the antisense oligonucleotide, this interaction can lead to silencing of a target gene (i.e. reducing the level of expression of mature mRNA and/or protein from that gene) or activation of a target gene (i.e. increasing the level of expression of mature mRNA and/or protein from that gene). The antisense oligonucleotides of the present disclosure are focused on activating gene expression, which can be done utilizing different mechanisms. Some antisense oligonucleotides are designed to recruit RNase H to cleave their target RNAs. RNase H is a family of non-sequence-specific endonuclease enzymes that catalyze the cleavage of RNA in an RNA/DNA substrate via a hydrolytic mechanism. In certain embodiments, the antisense oligonucleotides of the disclosure trigger RNase H-mediated cleavage of a pre-mRNA target (e.g., FXN pre-mRNA), which can be compatible with activation of overall target gene expression (e.g., FXN gene expression). Other antisense oligonucleotides, called steric blockers, are designed not to elicit cleavage of their targets but to block interactions with cellular factors. For example, these cellular factors could modulate splicing, block interactions of non-coding RNAs or of RNA-binding proteins, stabilize mRNA to prolong its half-life, or increase the efficiency of translation of an mRNA.

Antisense oligonucleotides designed to recruit RNase H are often designed as "gapmers." The term "gapmer" means a chimeric antisense oligonucleotide in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments." "Chimeric antisense oligonucleotide" means an antisense oligonucleotide that has at least two chemically distinct regions.

As used herein, the term "target gene" is a gene whose expression is to be substantially increased or restored. In certain embodiments, the target gene expression is increased or restored to wild type levels by a steric blocking antisense oligonucleotide that increases or restores expression through direct base pairing interactions with the target sequence (e.g., an FXN mRNA target sequence). In certain embodiments, the target gene expression is increased or restored to wild type levels through RNA silencing, e.g., by cleaving a transcript corresponding to a target gene or translational repression of the target gene. Without wishing to be bound by theory, cleavage of a target transcript can increase the levels of productive transcription of the target gene. For example, but in no way limiting, an allele of the target gene can be expressed to form pre-mRNA which can be defective (e.g., contain a nucleotide repeat region that contributes to disease). The target gene expression can be restored by cleaving and degrading the defective pre-mRNA derived from the defective allele, thereby freeing transcriptional machinery to trigger transcription of the non-defective target gene allele. The term "non-target gene" is a gene whose expression is not to be substantially increased or restored. For example, a target gene of the present disclosure is FXN, and a non-target gene of the present disclosure is a gene that is not FXN. In one embodiment, the polynucleotide sequences of the target and non-target gene (e.g., mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the target and non-target genes can share less than 99%, 98%, 97%, 96%, 95%, 94%, 93%, 92%, 91%, 90%, 89%, 88%, 86%, 85%, 80%, 75%, or 70% sequence identity. In another embodiment, the non-target gene can be a homologue (e.g., an orthologue or paralogue) of the target gene.

The term "antisense activity" means any detectable or measurable activity attributable to the hybridization of an antisense compound to its target nucleic acid. In some embodiments, antisense activity is an increase in the amount or expression of a target nucleic acid or protein encoded by such target nucleic acid. "Antisense compound" means an oligomeric compound that is capable of undergoing hybridization to a target nucleic acid through hydrogen bonding.

As used herein, "antisense oligonucleotide" means a single-stranded oligonucleotide having a nucleobase sequence that permits hybridization to a corresponding region or segment of a target nucleic acid.

The term "antisense inhibition" means reduction of target nucleic acid levels in the presence of an antisense oligonucleotide having a sequence that is sufficiently complementary to a target nucleic acid compared to target nucleic acid levels in the absence of the antisense compound. A target nucleic acid can be any nucleic acid. For example, a target nucleic acid of the present disclosure can be a FXN transcript. In certain embodiments, the target nucleic acid is FXN pre-mRNA.

The term "target-recognition sequence" refers to the portion of an antisense compound that recognizes a target nucleic acid. The target-recognition sequence has a nucleobase sequence that permits hybridization to a corresponding region or segment of a target nucleic acid.

The term "conserved region" refers to a portion, or portions, of a nucleic acid sequence that is conserved, i.e. a portion, or portions of the nucleic acid sequence having a similar or identical sequence across species. A conserved region can be computationally identified, e.g., using any sequence alignment software available in the art.

As used herein, the term "sufficiently complementary" means that the antisense compound has a sequence (e.g., an antisense oligonucleotide having a target-recognition sequence), which is sufficient to bind the desired target transcript (e.g., a FXN transcript), and to increase or restore expression of the FXN gene. For example, a target-recognition sequence with at least 90% complementarity to a target nucleic acid sequence (e.g., a portion of a FXN transcript) can be sufficiently complementary to increase or restore expression of the FXN gene. The term "perfectly complementary" refers to, e.g., a target-recognition sequence with 100% complementarity to a target nucleic acid sequence. Complementary nucleic acid molecules hybridize to each other. The term "hybridization" means the annealing of complementary nucleic acid molecules. In certain embodiments, complementary nucleic acid molecules include an antisense compound and a target nucleic acid.

As used herein, a "region of complementarity" refers to a portion of the antisense oligonucleotide that is complementary to the target transcript (e.g. the FXN transcript). For example, but in no way limiting, an 18-nucleotide long antisense oligonucleotide can comprise a contiguous 12-nucleotide portion that is complementary to the target transcript. In certain embodiments, the antisense oligonucleotide is complementary to the target transcript over the full length of the antisense oligonucleotide.

As used herein, "administer" or "administration" refers to the act of injecting or otherwise physically delivering a substance as it exists outside the body (e.g., an antisense compound provided herein) into a patient. The antisense oligonucleotides described herein can be administered to the central nervous system of a patient. The central nervous system includes the brain and spinal cord. Administration methods to the central nervous system include, but not limited to, intrathecal, intraventricular or intrastriatal infusion or delivery and/or any other method of physical delivery described herein or known in the art. Intraventricular infusion can comprise administration using an Ommaya reservoir. In some embodiments, the antisense oligonucleotides described herein can be administered to the patient systemically (such as intravenously, subcutaneously, or intramuscularly). These compounds can be designed to cross into the central nervous system, or to be active in other tissues, such as muscle (including skeletal or heart muscle) or pancreas.

When a disease, or a symptom thereof, is being managed or treated, the administration of the substance typically occurs after the onset of the disease or symptoms thereof. When a disease, or symptom thereof, is being prevented, administration of the substance typically occurs before the onset of the disease or symptoms thereof and can be continued chronically to defer or reduce the appearance or magnitude of disease-associated symptoms, e.g., damage to the involved tissues and airways.

As used herein, the term "composition" is intended to encompass a product containing the specified ingredients (e.g., an antisense compound provided herein) in, optionally, the specified amounts, as well as any product which results, directly or indirectly, from combination of the specified ingredients in, optionally, the specified amounts.

"Effective amount" means the amount of active pharmaceutical agent (e.g., an antisense compound of the present disclosure) sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

As used herein, the terms "subject" and "patient" are used interchangeably. As used herein, a subject can be a mammal, such as a non-primate (e.g., cows, pigs, horses, cats, dogs, rats, etc.) or a primate (e.g., monkey and human). In certain embodiments, the term "subject" refers to a vertebrate, such as a mammal. Mammals include, without limitation, humans, non-human primates, wild animals, feral animals, farm animals, sports animals, and pets. In one embodiment, the subject is a mammal, such as a human, having a FXN-related disorder (e.g., FRDA). In another embodiment, the subject is a mammal, such as a human, that is at risk for developing a FXN-related disorder.

As used herein, the term "therapy" refers to any protocol, method and/or agent that can be used in the prevention, management, treatment and/or amelioration of a disease or a symptom related thereto, such as a FXN-related disorder (e.g., FRDA). In some embodiments, the term "therapy" refers to any protocol, method and/or agent that can be used in the modulation of an immune response to an infection in a subject or a symptom related thereto. In some embodiments, the terms "therapies" and "therapy" refer to a biological therapy, supportive therapy, and/or other therapies useful in the prevention, management, treatment and/or amelioration of a disease or a symptom related thereto, such as a FXN-related disorder known to one of skill in the art such as medical personnel. In other embodiments, the terms "therapies" and "therapy" refer to a biological therapy, supportive therapy, and/or other therapies useful in the modulation of an immune response to an infection in a subject or a symptom related thereto known to one of skill in the art.

As used herein, the terms "treat," "treatment" and "treating" refer to the reduction or amelioration of the progression, severity, and/or duration of a disease or a symptom related thereto, such as a FXN-related disorder, resulting from the administration of one or more therapies (including, but not limited to, the administration of one or more prophylactic or therapeutic agents, such as an antisense oligonucleotide provided herein). The term "treating," as used herein, can also refer to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

Antisense Compounds

The present disclosure provides an antisense compound that is capable of increasing or restoring FXN gene expression by at least 5%, 10%, 15%, 20%, 25%, 30%, 35%, 40%, 45%, 50%, at least 55%, at least 60%, at least 65%, at least 70%, at least 75%, at least 80%, at least 85%, at least 90%, at least 95%, at least 100%, or more. In one embodiment, the antisense compound is capable of restoring FXN gene expression to wild-type levels. In one embodiment, the antisense compound is capable of increasing FXN gene above wild-type levels.

In certain embodiments, the antisense compounds that are capable of increasing or restoring FXN gene expression, have chemically modified subunits arranged in patterns, or motifs, to confer to the antisense compounds properties such as enhanced the activity, increased binding affinity for a target nucleic acid, or resistance to degradation by in vivo nucleases.

In some embodiments, an antisense compound of the present disclosure is an antisense oligonucleotide. Chimeric antisense oligonucleotides typically contain at least one region modified so as to confer increased resistance to nuclease degradation, increased cellular uptake, increased binding affinity for the target nucleic acid, and/or increased activity. A second region of a chimeric antisense compound can optionally serve as a substrate for the cellular endonuclease RNase H, which cleaves the RNA strand of an RNA:DNA duplex. In some embodiments, an antisense compound of the present disclosure is a chimeric antisense oligonucleotide having a gapmer motif. In a gapmer, an internal region having a plurality of nucleotides that supports RNase H cleavage is positioned between external regions having a plurality of nucleotides that are chemically distinct from the nucleosides of the internal region.

In some embodiments, the present disclosure provides an antisense oligonucleotide having a target-recognition sequence that is sufficiently complementary to an FXN transcript or portion thereof, to direct cleavage of the FXN transcript by RNase H. The target-recognition sequence of the antisense oligonucleotide can be the full length of the antisense oligonucleotide, or a portion thereof. In some embodiments, the antisense oligonucleotide comprises a gapmer motif In the case of an antisense compound having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer can in some embodiments include β-D-ribonucleosides, β-D-deoxyribonucleosides, 2'-modified nucleosides (such 2'-modified nucleosides can include 2'-MOE, and 2'-O—CH$_3$ (i.e., OMe), among others), and bicyclic sugar modified nucleosides (such bicyclic sugar modified nucleosides can include those having a 4'-(CH$_2$)$_n$—O-2' bridge, where n=1 or n=2). In some embodiments, the wing segments of the gapmer contain one or more tricyclo-DNA (tcDNA) modifications. In some embodiments, each distinct region comprises uniform sugar moieties. In some embodiments, each wing segment comprises a mixture of different nucleotide modifications. For example, in one embodiment, a LNA modification and a 2'-MOE modification could be used in combination for one antisense compound. In one embodiment, a LNA modification and a 2'-O-Methyl modification could be used in combination for one antisense compound. In one embodiment, a LNA modification and a 2'-deoxy modification could be used in combination for one antisense compound. In one embodiment, a LNA modification and a tricyclo-DNA modification could be used in combination for one antisense compound. In one embodiment, a 2'-MOE modification and a tricyclo-DNA modification could be used in combination for one antisense compound.

The gapmer motif can be described using the formula "A-B-C", where "A" represents the length of the 5' wing region, "B" represents the length of the gap region, and "C" represents the length of the 3' wing region. As such, in some embodiments, an antisense oligonucleotide of the present disclosure has the formula:

A-B-C.

As used herein, a gapmer described as "A-B-C" has a configuration such that the gap segment is positioned immediately adjacent each of the 5' wing segment and the 3' wing segment. Thus, no intervening nucleotides exist between the 5' wing segment and gap segment, or the gap segment and the 3' wing segment.

In some embodiments, the 5' wing region represented by "A" comprises from about 0 to about 8 modified nucleotides, e.g., from about 1 to about 6 modified nucleotides. For example, the 5' wing region represented by "A" can be 0, 1, 2, 3, 4, 5, 6, 7, or 8 nucleotides in length. In some embodiments, the 3' wing region represented by "C" comprises about 0 to about 8 modified nucleotides, e.g., from about 1 to about 6 modified nucleotides. For example, the 3' wing region represented by "C" can be 0, 1, 2, 3, 4, 5, 6, 7, or 8 nucleotides in length. In some embodiments, "A" and "C" are the same, in some embodiments, they are different.

In some embodiments, the gap region represented by "B" comprises from about 6 to about 18 DNA nucleotides and/or DNA-like nucleotides, e.g., from about 6 to about 12 DNA nucleotides and/or DNA-like nucleotides. For example, the gap region represented by "B" can be 6, 7, 8, 9, 10, 11, 12, 13, 14, 15, 16, 17, or 18 DNA nucleotides and/or DNA-like nucleotides in length. Thus, an antisense oligonucleotide of the present disclosure having a target-recognition sequence with the formula "A-B-C" include, but are not limited to the following gapmer formats, for example 1-10-1 (i.e., one nucleotide-ten nucleotides-one nucleotide), 1-10-1, 1-11-1, 1-12-1, 2-8-2, 2-9-2, 2-10-2, 2-11-2, 2-12-2, 3-6-3, 3-7-3, 3-8-3, 3-9-3, 3-10-3, 3-11-3, 3-12-3, 4-6-4, 4-7-4, 4-8-4, 4-9-4, 4-10-4, 4-11-4, 4-12-4, 5-6-5, 5-7-5, 5-8-5, 5-9-5, 5-10-5, 5-11-5, 5-12-5, 6-6- 6, 6-7-6, 6-8-6, 6-9-6, 6-10-6, 6-11-6, or 6-12-6. The wings can also be of different lengths, such as 1-10-6, 3-9-5, 7-9-2, 4-10-5, or other asymmetric combinations of wing lengths flanking a central DNA gap. In certain embodiments, the gapmer of "A-B-C" is at least 12 nucleotides in length. In certain embodiments, "B" is at least 6 nucleotides in length. A person of skill in the art will be able to identify additional asymmetric combinations of wing lengths.

In certain embodiments, antisense compounds targeted to a FXN nucleic acid possess a 5-9-4 gapmer format. In some embodiments, the antisense compound is an antisense oligonucleotide having a target-recognition sequence with the 5-9-4 format that is sufficiently complementary to a FXN transcript, or a portion thereof, to direct cleavage of the FXN transcript by RNase H. In some embodiments, the target-recognition sequence has the formula "A-B-C", wherein "A" comprises about 2 to 6 modified nucleotides, "B" comprises about 6 to 12 DNA nucleotides and/or DNA-like nucleotides, and "C" comprises about 2 to 6 modified nucleotides. In some embodiments, the target-recognition sequence has the formula "A-B-C", wherein "A" comprises 5 modified nucleotides, "B" comprises 9 DNA nucleotides and/or DNA-like nucleotides, and "C" comprises 4 modified nucleotides. In some embodiments, the target-recognition sequence has the formula "A-B-C", wherein "A" comprises 2 to 6 2'-O-(2-methoxyethyl) (MOE) modified nucleotides, "B" comprises 6 to 12 DNA nucleotides and/or DNA-like nucleotides, and "C" comprises 2 to 6 2'-O-(2-methoxyethyl) (MOE) modified nucleotides. In some embodiments, the target-recognition sequence has the formula "A-B-C", wherein "A" comprises 5 2'-O-(2-methoxyethyl) (MOE) modified nucleotides, "B" comprises 9 DNA nucleotides and/or DNA-like nucleotides, and "C" comprises 4 2'-O-(2-methoxyethyl) (MOE) modified nucleotides.

In some embodiments, antisense compounds that target a FXN nucleic acid possess a "wingmer" motif. The wingmer motif can be described using the formula "X—Y" or "Y—X", where "X" represents the length of the wing region, and "Y" represents the length of the gap region. As such, in some embodiments, an antisense oligonucleotide of the present disclosure has the formula:

X—Y, or

Y—X.

As used herein, a wingmer described as "X—Y" or "Y—X" has a configuration such that the gap segment is positioned immediately adjacent to the wing segment. Thus, no intervening nucleotides exist between the wing segment and the gap segment. Non-limiting examples of wingmer configurations of an antisense compound of the present disclosure include, e.g., 1-15, 1-17, 1-19, 2-15, 2-17, 2-19, 2-22, 3-13, 3-17, 3-20, 3-21, 3-22, 4-12, 4-14, 4-16, 4-18, 4-19, 4-21, 5-11, 5-13, 5-14, 5-15, 5-16, 5-18, or 5-20.

In some embodiments, antisense compounds targeted to a FXN nucleic acid possess a gap-widened motif. As used herein, "gap-widened" refers to an antisense compound having a gap segment of 12 or more contiguous DNA nucleotides and/or DNA-like nucleotides adjacent to a wing region. In the case of a gap-widened gapmer, the gapmer comprises a gap region having 12 or more contiguous DNA nucleotides and/or DNA-like nucleotides positioned between and immediately adjacent to the 5' and 3' wing segments. In the case of a gap-widened wingmer, the wingmer comprises a gap region having 12 or more contiguous DNA nucleotides and/or DNA-like nucleotides positioned immediately adjacent to the wing segment.

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidates, and phosphorothioates. Methods of preparation of phosphorous-containing and non-phosphorous-containing linkages are well known.

In certain embodiments, antisense compounds targeted to a FXN nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Antisense compounds of the disclosure can optionally contain one or more nucleosides wherein the sugar group has been modified. Such sugar-modified nucleosides can impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substituent groups (including 5' and 2' substituent groups, bridging of ring atoms to form bicyclic nucleic acids (BNA), replacement of the ribosyl ring oxygen atom with S, N(R), or $C(R^1)(R^2)$ (R=H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F (i.e., 2'-fluoro), 2'-$OCH_3$ (i.e., 2'-O-methyl) and 2'-$O(CH_2)_2OCH_3$ (i.e., 2'-O-methoxyethyl) substituent groups. The substituent at the 2' position can also be selected from allyl, amino, azido, thio, O-allyl, O—C1-C10 alkyl, $OCF_3$, $O(CH_2)_2SCH_3$, $O(CH_2)_2$—O—N $(R_m)(R_n)$, and O—$CH_2$—C(=O)—N$(R_m)(R_n)$, where each $R_m$ and $R_n$ is, independently, H or substituted or unsubstituted C1-C10 alkyl. 2'-modified nucleotides are useful in the present disclosure, for example, 2'-O-methyl RNA, 2'-O-methoxyethyl RNA, 2'-fluoro RNA, and others envisioned by one of ordinary skill in the art.

Examples of bicyclic nucleic acids (BNAs) include without limitation nucleosides comprising a bridge between the 4' and the 2' ribosyl ring atoms. A BNA comprising a bridge between the 4' and 2' ribosyl ring atoms can be referred to as a locked nucleic acid (LNA), and is often referred to as inaccessible RNA. As used herein, the term "locked nucleotide" or "locked nucleic acid (LNA)" comprises nucleotides in which the 2' deoxy ribose sugar moiety is modified by introduction of a structure containing a heteroatom bridging from the 2' to the 4' carbon atoms. The term "non-locked nucleotide" comprises nucleotides that do not contain a bridging structure in the ribose sugar moiety. Thus, the term comprises DNA and RNA nucleotide monomers (phosphorylated adenosine, guanosine, uridine, cytidine, deoxyadenosine, deoxyguanosine, deoxythymidine, deoxycytidine) and derivatives thereof as well as other nucleotides having a 2'-deoxy-erythro-pentofuranosyl sugar moiety or a ribopentofuranosyl moiety. In certain embodiments, antisense compounds provided herein include one or more BNA nucleosides wherein the bridge comprises one of the formulas: 4'-($CH_2$)—O-2' (LNA); 4'-($CH_2$)—S-2; 4'-($CH_2$)—O-2' (LNA); 4'-($CH_2$)2-O-2' (ENA); 4'-C($CH_3$)2—O-2' (see PCT/US2008/068922); 4'-CH($CH_3$)—O-2' and 4'-CH($CH_2OCH_3$)—O-2' (see U.S. Pat. No. 7,399,845, issued on Jul. 15, 2008); 4'-$CH_2$—N($OCH_3$)-2' (see PCT/US2008/064591); 4'-$CH_2$—O—N($CH_3$)-2' (see published U.S. Patent Application US2004-0171570, published Sep. 2, 2004); 4'-$CH_2$—N(R)—O-2' (see U.S. Pat. No. 7,427,672, issued on Sep. 23, 2008); 4'-$CH_2$—C($CH_3$)-2' and 4'-$CH_2$—C(=$CH_2$)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In some embodiments, antisense compounds provided herein include one or more 2', 4'-constrained nucleotides. For example, antisense compounds provided by the present disclosure include those having one or more constrained ethyl (cEt) or constrained methoxyethyl (cMOE) nucleotides. In some embodiments, antisense compounds provided herein are antisense oligonucleotides comprising one or more constrained ethyl (cEt) nucleotides. The terms "constrained ethyl" and "ethyl-constrained" are used interchangeably.

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

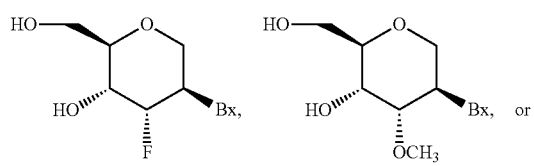

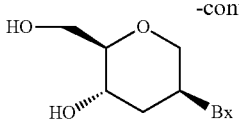

In certain embodiments, antisense oligonucleotides may comprise morpholino rings joined by phosphorodiamidate linkages. These may be referred to as PMO oligomers or phosphorodiamidate morpholino oligomers. In certain such embodiments, the backbone of these oligonucleotides may be uncharged. In other embodiments, one or more of the phosphorodiamidate linkages may comprise a charged moiety.

Many other bicyclo and tricyclo sugar surrogate ring systems are also known in the art that can be used to modify nucleosides for incorporation into antisense compounds (see for example review article: Leumann, J. C, *Bioorganic & Medicinal Chemistry*, 2002, 10, 841-854; Ito, K. R.; Obika, S., Recent Advances in Medicinal Chemistry of Antisense Oligonucleotides. In *Comprehensive Medicinal Chemistry*, 3rd edition, Elsevier: 2017). Such ring systems can undergo various additional substitutions to enhance activity.

Methods for the preparations of modified sugars are well known to those skilled in the art. In nucleotides having modified sugar moieties, the nucleobase moieties (natural, modified or a combination thereof) are maintained for hybridization with an appropriate nucleic acid target.

In certain embodiments, antisense compounds targeted to a FXN nucleic acid comprise one or more kinds of modified nucleotides. In one embodiment, antisense compounds targeted to a FXN nucleic acid comprise 2'-modified nucleotides. In one embodiment, antisense compounds targeted to a FXN nucleic acid comprise a 2'-O-methyl RNA, a 2'-O-methoxyethyl RNA, or a 2'-fluoro RNA. In one embodiment, antisense compounds targeted to a FXN nucleic acid comprise tricyclo-DNA (tcDNA). Tricyclo-DNA belongs to a class of constrained DNA analogs that display improved hybridizing capacities to complementary RNA, see, e.g., Ittig et al., *Nucleic Acids Res.* 32:346-353 (2004); Ittig et al., Prague, Academy of Sciences of the Czech Republic. 7:21-26 (Coll. Symp. Series, Hocec, M., 2005); Ivanova et al., *Oligonucleotides* 17:54-65 (2007); Renneberg et al., *Nucleic Acids Res.* 30:2751-2757 (2002); Renneberg et al., *Chembiochem.* 5:1114-1118 (2004); and Renneberg et al., JACS. 124:5993-6002 (2002). In one embodiment, antisense compounds targeted to a FXN nucleic acid comprise a locked nucleotide, an ethyl-constrained nucleotide, or an alpha-L-locked nucleic acid. Various alpha-L-locked nucleic acids are known by those of ordinary skill in the art, and are described in, e.g., Sorensen et al., *J. Am. Chem. Soc.* (2002) 124(10):2164-2176.

In certain embodiments, the antisense compounds targeting a FXN nucleic acid are fully chemically modified, i.e., every nucleotide is chemically modified. In certain embodiments, every nucleotide comprises a 2'-O-(2-methoxyethyl) (MOE) modification. In certain embodiments, every nucleotide comprises a tricyclo-DNA modification. In certain embodiments, the antisense compounds targeting a FXN nucleic acid comprise a mixture of tricyclo-DNA modifications and 2'-O-(2-methoxyethyl) (MOE) modifications, wherein every nucleotide of the antisense compounds is either tcDNA or MOE.

In certain embodiments, antisense compounds targeted to a FXN nucleic acid comprise one or more modified nucleotides having modified sugar moieties. In some embodiments, the modified nucleotide is a locked nucleotide. In certain embodiments, the locked nucleotides are arranged in a gapmer motif, e.g. a 3-9-3 gapmer format wherein 9 non-locked nucleotides are flanked by 3 locked nucleotides on each side.

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo such as 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In certain embodiments, antisense compounds targeted to a FXN nucleic acid comprise one or more modified nucleotides having modified sugar moieties. In some embodiments, the modified nucleotide is a locked nucleotide. In certain embodiments, the locked nucleotides are arranged in a gapmer motif, e.g. a 3-9-3 gapmer format wherein 9 non-locked nucleotides are flanked by 3 locked nucleotides on each side. In certain embodiments, antisense compounds targeted to a FXN nucleic acid comprise one or more modified nucleotides. In some embodiments, the modified nucleotide is 5-methylcytosine. In certain embodiments, each cytosine is a 5-methylcytosine. In some embodiments, the modified nucleotide is a 2'-O-(2-methoxyethyl) (MOE) modified nucleotide. In certain embodiments, the 2'-O-(MOE) modified nucleotides are arranged in a gapmer motif, e.g. a 5-9-4 gapmer format wherein 9 non-2'-O— (MOE) modified nucleotides are flanked by 4 or 5 2'-O— (MOE) modified nucleotides on one or both sides. In certain embodiments, antisense compounds targeted to a FXN nucleic acid comprise a steric blocking chemical modification format. In some embodiments of the steric blocking chemical modification format, every nucleotide of the antisense compound is a 2'-O-(2-methoxyethyl) (MOE) modified nucleotide. In some embodiments of the steric blocking chemical modification format, every nucleotide of the antisense compound is a tricyclo-DNA modified nucleotide. In some embodiments of the steric blocking chemical modification format, the antisense compound comprises at least one MOE modified nucleotide and at least one tricyclo-DNA modified nucleotide. Many different chemical modification patterns steric blocking antisense oligonucleotides are envisioned. For example, but in no way limiting, the steric blocking antisense oligonucleotide can comprise a mixture of different types of modifications, such as a mixture of 2'-O-(2-methoxyethyl) modifications, LNA modifications, tricyclo-DNA modifications, and DNA modifications where the DNA stretches are four nucleotides or less.

In some embodiments, an antisense compound of the present disclosure directs cleavage of a FXN transcript by RNase H. In such embodiments, the antisense compound can be referred to as an RNase H-dependent antisense compound. In some embodiments the antisense compound is an RNase H-dependent antisense oligonucleotide. In some embodiments, an antisense oligonucleotide of the present disclosure is an RNase H-dependent antisense oligonucleotide, and can be a single-stranded, chemically modified oligonucleotide that binds to a complementary sequence in the target transcript (e.g., a FXN transcript). An RNase H-dependent antisense oligonucleotide of the present disclosure reduces expression of a target gene by RNase H-mediated cleavage of the target transcript, and by inhibition of translation by steric blockade of ribosomes. In some embodiments, an antisense compound of the present disclosure is capable of mediating cleavage of at least 50%, at least 55%, at least 60%, at least 65%, at least 70%, at least 75%, at least 80%, at least 85%, at least 90%, at least 95% or more of FXN transcripts by RNase-H. In one embodiment, the antisense compound is capable of mediating cleavage of at least 80% of FXN transcripts by RNase-H. In one embodiment, the antisense compound is capable of mediating cleavage of at least 90% of FXN transcripts by RNase-H.

In certain embodiments, an antisense compound that targets a FXN transcript is from about 6 to about 24 subunits in length. In other embodiments, the antisense compound that targets a FXN transcript is from about 8 to about 80 subunits in length. For example, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments, the antisense compounds are less than 40 linked subunits in length. In some embodiments, the antisense compounds are from about 10 to about 30 linked subunits in length. In some embodiments, the antisense compounds are from about 12 to about 25 linked subunits in length. In some embodiments, the antisense compounds are from about 15 to about 20 linked subunits in length. In some embodiments, the antisense compound is an antisense oligonucleotide that targets a FXN transcript, and the linked subunits are linked nucleotides.

In certain embodiments antisense compounds targeted to a FXN transcript can be shortened or truncated. For example, a single subunit can be deleted from the 5' end (5' truncation), or alternatively from the 3' end (3' truncation). A shortened or truncated antisense compound targeted to a FXN transcript can have two subunits deleted from the 5' end, or alternatively can have two subunits deleted from the 3' end, of the antisense compound. Alternatively, the deleted nucleosides can be dispersed throughout the antisense compound, for example, in an antisense compound having one nucleoside deleted from the 5' end and one nucleoside deleted from the 3' end.

When a single additional subunit is present in a lengthened antisense compound, the additional subunit can be located at the 5' or 3' end of the antisense compound. When two or more additional subunits are present, the added subunits can be adjacent to each other, for example, in an antisense compound having two subunits added to the 5' end (5' addition), or alternatively to the 3' end (3' addition), of the antisense compound. Alternatively, the added subunits can be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

In certain embodiments, the antisense oligonucleotide comprises the formula:

A-B-C, wherein:

A comprises from about 0 to about 18 modified nucleotides;

B comprises from about 0 to about 4 deoxyribonucleic acid (DNA) nucleotides and/or DNA-like nucleotides; and C comprises from about 0 to about 18 modified nucleotides;

and the overall length of the antisense oligonucleotide is about 10 to about 30 nucleotides. Antisense oligonucleotides that contain 4 or fewer DNA and/or DNA-like nucleotides in "B" should not recruit RNase H and direct cleavage of a target. In these instances, the antisense oligonucleotide is not a gapmer format, but can rather act as a steric blocker.

Branched Antisense Compounds

The present disclosure also provides branched antisense compounds comprising two or more target-recognition sequences that targets a portion of a FXN nucleic acid. A branched antisense compound of the present disclosure can be, e.g., a branched antisense oligonucleotide compound.

As used herein, the term "branched antisense compound" or "branched antisense oligonucleotide" refers to two or more antisense compounds or antisense oligonucleotides that are connected together.

In one embodiment, a branched oligonucleotide compound comprises two or more target-recognition sequences, wherein the target-recognition sequences are connected to one another by one or more moieties selected from a linker, a spacer, and a branching point. Target-recognition sequences are described herein. In some embodiments, the branched oligonucleotide compound comprises 2, 3, 4, 5, 6, 7, 8, or more target-recognition sequences, wherein each target-recognition sequences comprises a 5' end and a 3' end, and each target-recognition sequence is independently connected to a linker, a spacer, or a branching point at the 5' end or the 3' end. In some embodiments, each target-recognition sequence is connected to a linker, a spacer, or a branching point at the 5' end. In some embodiments, each target-recognition sequence is connected to a linker, a spacer, or a branching point at the 3' end. In another embodiment, each target-recognition sequence is connected to a linker, a spacer, or a branching point. In some embodiments, each of the target-recognition sequences are antisense compounds and/or oligonucleotides that target a portion of a FXN nucleic acid.

In some embodiments, a branched oligonucleotide compound of the present disclosure has the formula L-(N)$_n$ wherein N represents a target-recognition sequence of the present disclosure; n represents an integer, e.g., 2, 3, 4, 5, 6, 7, or 8; and L represents a linker selected from an ethylene glycol chain, an alkyl chain, a peptide, RNA, DNA, a phosphate, a phosphonate, a phosphoramidate, an ester, an amide, a triazole, and any combination thereof.

In some embodiments, a branched oligonucleotide compound of the present disclosure has the formula L-(N)$_n$ wherein the compound optionally further comprises one or more branching points B, and wherein the compound optionally further comprises one or more spacers S. In such embodiments, each of the one or more branching points B independently represents a polyvalent organic species or derivative thereof, and each of the one or more spacers S is independently selected from an ethylene glycol chain, an alkyl chain, a peptide, RNA, DNA, a phosphate, a phosphonate, a phosphoramidate, an ester, an amide, a triazole, and any combination thereof. In some embodiments, the spacer S is biocleavable. For example, the spacer S could include moieties susceptible to cleavage by nucleases, by proteases, by changes in pH, or by reduction or oxidation. In such embodiments, spacers could include peptides, phosphodiester-linked nucleotides, disulfide bonds, pH-sensitive linkages or other biocleavable moieties. For example, a branched oligonucleotide compound of the present disclosure having the formula L-(N)n has a structure, not to be limited in any fashion, e.g.,

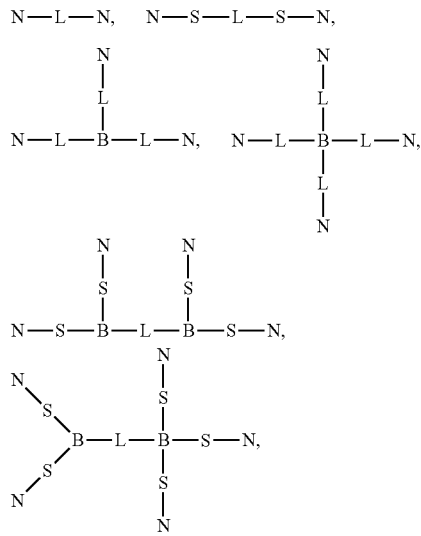

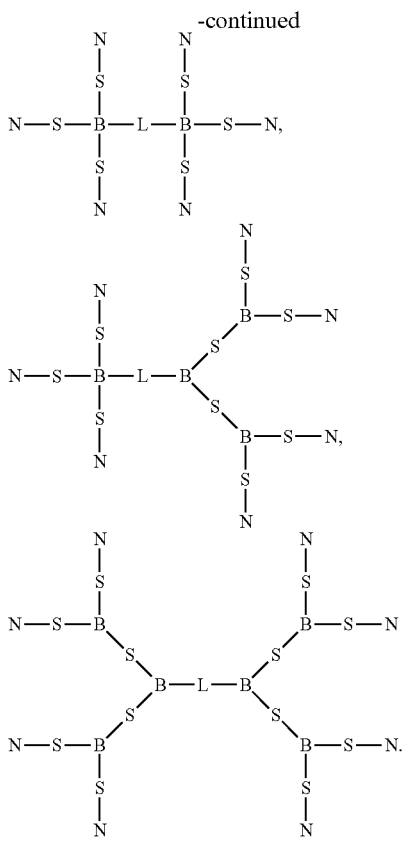

Target-Recognition Sequences

The present disclosure provides an antisense oligonucleotide comprising a target-recognition sequence that targets a portion of a Frataxin (FXN) nucleic acid (e.g., a FXN transcript). In certain embodiments, an antisense oligonucleotide has a nucleobase sequence that, when written in the 5' to 3' direction, comprises the reverse complement of a portion of a FXN nucleic acid. In certain such embodiments, an antisense oligonucleotide has a nucleobase sequence that, when written in the 5' to 3' direction, comprises the reverse complement of a portion of a FXN nucleic acid.

In certain embodiments, a target region is a structurally defined region of a FXN nucleic acid. For example, a target region can encompass a 3' untranslated region (UTR), a 5' untranslated region (UTR), an exon, an intron, an exon/intron junction, a coding region, a translation initiation region, translation termination region, or other defined nucleic acid region, for example, an open reading frame, or the junction between an open reading frame and an untranslated region and any combinations thereof. The structurally defined regions for FXN can be obtained by accession number from sequence databases such as NCBI and such information is incorporated herein by reference. In certain embodiments, a target region can encompass the sequence from a 5' target site of one target segment within the target region to a 3' target site of another target segment within the same target region.

Targeting includes determination of at least one target segment to which an antisense oligonucleotide hybridizes, such that a desired effect occurs. In certain embodiments, the desired effect is an increase in transcript target nucleic acid levels, i.e., an increase in FXN transcript levels. In certain embodiments, the desired effect is an increase of levels of protein encoded by the target nucleic acid or a phenotypic change associated with the target nucleic acid, e.g., an increase in the level of FXN protein.

A target region can contain one or more target segments. Multiple target segments within a target region can be overlapping. Alternatively, they can be non-overlapping. In certain embodiments, target segments within a target region are separated by no more than about 300 nucleotides. In certain embodiments, target segments within a target region are separated by a number of nucleotides that is about 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than about 5 nucleotides on the target nucleic acid. In certain embodiments, target segments are contiguous.

Suitable target segments can be found within a 5' UTR, a coding region, a 3' UTR, an intron, an exon, and/or an exon/intron junction. Target segments containing a start codon or a stop codon are also suitable target segments. A suitable target segment can specifically exclude a certain structurally defined region such as the start codon or stop codon. In certain embodiments, the target segments are found in intron 1 of the FXN gene. In certain embodiments, the target segments are found upstream (5') of a nucleotide repeat region in intron 1 of the FXN gene. In certain embodiments, the target segments are found downstream (3') of a nucleotide repeat region in intron 1 of the FXN gene. In certain embodiments, the target segments are found upstream or downstream of a nucleotide repeat region in intron 1 of the FXN gene and are unique in a human genome (i.e., the target segment nucleic acid sequence is found only once in the human genome).

The determination of suitable target segments can include a comparison of the sequence of a target nucleic acid (e.g., FXN) to other sequences throughout the genome. For example, the BLAST algorithm can be used to identify regions of similarity amongst different nucleic acids. This comparison can prevent the selection of antisense oligonucleotide sequences that can hybridize in a non-specific manner to sequences other than a selected target nucleic acid (i.e., non-target or off-target sequences). The determination of suitable target segments can include comparison of the sequences of a target nucleic acid (e.g., a FXN transcript) across several species. For example, various sequence alignment software can be used to identify regions of similar or identical sequence across species. In certain embodiments, the FXN transcript target segment nucleic acid sequences are unique in the human genome (i.e., the target segment nucleic acid sequence is found only once in the human genome).

There can be variation in activity (e.g., as defined by percent increase of target nucleic acid levels) of the antisense oligonucleotides within an active target region. In certain embodiments, increase in FXN transcript levels is indicative of increased or restored of FXN expression. Increases in levels of a FXN protein are also indicative of increased or restored target transcript expression. Further, phenotypic changes are indicative of increased or restored FXN expression. In some embodiments, modulation (i.e., increase or decrease) in the transcript levels of a gene that operates within a FXN genetic pathway can indicate increased or restored FXN expression. For example, modulation in the transcript levels of a downstream component of a FXN genetic pathway is indicative increased or restored FXN expression.

An antisense oligonucleotide and a target nucleic acid (e.g., a FXN transcript or portion thereof) are complementary to each other when a sufficient number of nucleobases of the antisense oligonucleotide can hydrogen bond with the corresponding nucleobases of the target nucleic acid, such that a desired effect will occur (e.g., increased expression of a target nucleic acid, such as a FXN transcript or portion thereof).

Non-complementary nucleobases between an antisense oligonucleotide and a FXN nucleic acid can be tolerated provided that the antisense oligonucleotide remains able to specifically hybridize to a target nucleic acid. Moreover, an antisense oligonucleotide can hybridize over one or more segments of a FXN nucleic acid such that intervening or adjacent segments are not involved in the hybridization event (e.g., a loop structure, mismatch or hairpin structure).

In certain embodiments, the antisense oligonucleotides provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a FXN nucleic acid, a target region, target segment, or specified portion thereof.

For example, an antisense oligonucleotide in which 18 of 20 nucleobases of the antisense oligonucleotide are complementary to a target region (e.g., an equal length portion of a FXN transcript), and would therefore specifically hybridize, would represent 90 percent complementarity. In this example, the remaining noncomplementary nucleobases can be clustered or interspersed with complementary nucleobases and need not be contiguous to each other or to complementary nucleobases. As such, an antisense oligonucleotide which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present disclosure. Percent complementarity of an antisense oligonucleotide with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense oligonucleotides provided herein, or specified portions thereof, are fully complementary (i.e. 100% complementary) to a target nucleic acid, or specified portion thereof. For example, antisense oligonucleotide can be fully complementary to a FXN nucleic acid, or a target region, or a target segment or target sequence thereof. As used herein, "fully complementary" or "perfectly complementary" means each nucleobase of an antisense oligonucleotide is capable of precise base pairing with the corresponding nucleobases of a target nucleic acid. For example, a 20 nucleobase antisense oligonucleotide is perfectly complementary to a target sequence that is 400 nucleobases long, so long as there is a corresponding 20 nucleobase portion of the target nucleic acid that is fully complementary to the antisense oligonucleotide. Perfectly complementary can also be used in reference to a specified portion of the first and/or the second nucleic acid. For example, a 20 nucleobase portion of a 30 nucleobase antisense oligonucleotide can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense oligonucleotide. At the same time, the entire 30 nucleobase antisense oligonucleotide may or may not be fully complementary to the target sequence, depending on whether the remaining 10 nucleobases of the antisense oligonucleotide are also complementary to the target sequence.

FXN target nucleic acid sequences are described below in Table 1.

TABLE 1

FXN intron 1 target nucleic acid sequences

| Target Region | Sequence (5'-3') |
|---|---|
| FXN intron 1 (full sequence) GAA repeat region is bold and underlined | AAGAAAACTTTCACAATTTGCATCCCTTTGTAATATGTAACAGAA ATAAAATTCTCTTTTAAAATCTATCAACAATAGGCAAGGCACGG TGGCTCACGCCTGTCGTCTCAGCACTTTGTGAGGCCCAGGCGGGC AGATCGTTTGAGCCTAGAAGTTCAAGACCACCCTGGGCAACATA GCGAAACCCCCTTTCTACAAAAAATACAAAAACTAGCTGGGTGT GGTGGTGCACACCTGTAGTCCCAGCTACTTGGAAGGCTGAAATG GGAAGACTGCTTGAGCCCGGGAGGGAGAAGTTGCAGTAAGCCA GGACCACACCACTGCACTCCAGCCTGGGCAACAGAGTGAGACTC TGTCTCAAACAAACAAATAAATGAGGCGGGTGGATCACGAGGTC AGTAGATCGAGACCATCCTGGCTAACACGGTGAAACCCGTCTCT ACTAAAAAAAAAAAAAAATACAAAAAATTAGCCAGGCATGGTG GCGGGCGCCTGTAGTCCCAGTTACTCGGGAGGCTGAGGCAGGAG AATGGCGTGAAACCGGGAGGCAGAGCTTGCAGTGAGCCGAGAT CGCACCACTGCCCTCCAGCCTGGGCGACAGAGCGAGACTCCGTC TCAATCAATCAATCAATCAATAAAATCTATTAACAATATTTATTG TGCACTTAACAGGAACATGCCCTGTCCAAAAAAAACTTTACAGG GCTTAACTCATTTTATCCTTACCACAATCCTATGAAGTAGGAACT TTTATAAAACGCATTTTATAAACAAGGCACAGAGAGGTTAATTA ACTTGCCCTCTGGTCACACAGCTAGGAAGTGGGCAGAGTACAGA TTTACACAAGGCATCCGTCTCCTGGCCCCACATACCCAACTGCTG TAAACCCATACCGGCGGCCAAGCAGCCTCAATTTGTGCATGCAC CCACTTCCCAGCAAGACAGCAGCTCCCAAGTTCCTCCTGTTTAGA ATTTTAGAAGCGGCGGGCCACCAGGCTGCAGTCTCCCTTGGGTC AGGGGTCCTGGTTGCACTCCGTGCTTTGCACAAAGCAGGCTCTCC ATTTTTGTTAAATGCACGAATAGTGCTAAGCTGGGAAGTTCTTCC |

TABLE 1-continued

FXN intron 1 target nucleic acid sequences

| Target Region | Sequence (5'-3') |
|---|---|
| | TGAGGTCTAACCTCTAGCTGCTCCCCCACAGAAGAGTGCCTGCG |
| | GCCAGTGGCCACCAGGGGTCGCCGCAGCACCCAGCGCTGGAGGG |
| | CGGAGCGGGCGGCAGACCCGGAGCAGCATGTGGACTCTCGGGC |
| | GCCGCGCAGTAGCCGGCCTCCTGGCGTCACCCAGCCCAGCCCAG |
| | GCCCAGACCCTCACCCGGGTCCCGCGGCCGGCAGAGTTGGCCCC |
| | ACTCTGCGGCCGCCGTGGCCTGCGCACCGACATCGATGCGACCT |
| | GCACGCCCCGCCGCGCAGTAAGTATCCGCGCCGGGAACAGCCGC |
| | GGGCCGCACGCCGCGGGCCGCACGCCGCACGCCTGCGCAGGGA |
| | GGCGCCGCGCACGCCGGGGTCGCTCCGGGTACGCGCGCTGGACT |
| | AGCTCACCCCGCTCCTTCTCAGGGCGGCCCGGCGGAAGCGGCCT |
| | TGCAACTCCCTTCTCTGGTTCTCCCGGTTGCATTTACACTGGCTTC |
| | TGCTTTCCGAAGGAAAAGGGGACATTTTGTCCTGCGGTGCGACT |
| | GCGGGTCAAGGCACGGGCGAAGGCAGGGCAGGCTGGTGGAGGG |
| | GACCGGTTCCGAGGGGTGTGCGGCTGTCTCCATGCTTGTCACTTC |
| | TCTGCGATAACTTGTTTCAGTAATATTAATAGATGGTATCTGCTA |
| | GTATATACATACACATAATGTGTGTGTCTGTGTGTATCTGTATAT |
| | AGCGTGTGTGTTGTGTGTGTGTTTGCGCGCACGGGCGCGCGCA |
| | CACCTAATATTTTCAAGGCTGGATTTTTTTGAACGAAATGCTTTC |
| | CTGGAACGAGGTGAAACTTTCAGAGCTGCAGAATAGCTAGAGCA |
| | GCAGGGGCCCTGGCTTTTGGAAACTGACCCGACCTTTATTCCAGA |
| | TTCTGCCCCACTCCGCAGAGCTGTGTGACCTTGGGGGATTCCCCT |
| | AACCTCTCTGAGACGTGGCTTTGTTTTCTGTAGGGAGAAGATAAA |
| | GGTGACGCCCATTTTGCGGACCTGGTGTGAGGATTAAATGGGAA |
| | TAACATAGATAAAGTCTTCAGAACTTCAAATTAGTTCCCCTTTCT |
| | TCCTTTGGGGGGTACAAAGAAATATCTGACCCAGTTACGCCACG |
| | GCTTGAAAGGAGGAAACCCAAAGAATGGCTGTGGGGATGAGGA |
| | AGATTCCTCAAGGGGAGGACATGGTATTTAATGAGGGTCTTGAA |
| | GATGCCAAGGAAGTGGTAGAGGGTGTTTCACGAGGAGGGAACC |
| | GTCTGGGCAAAGGCCAGGAAGGCGGAAGGGGATCCCTTCAGAG |
| | TGGCTGGTACGCCGCATGTATTAGGGGAGATGAAAGAGGCAGGC |
| | CACGTCCAAGCCATATTTGTGTTGCTCTCCGGAGTTTGTACTTTA |
| | GGCTTGAACTTCCCACACGTGTTATTTGGCCCACATTGTGTTTGA |
| | AGAAACTTTGGGATTGGTTGCCAGTGCTTAAAAGTTAGGACTTA |
| | GAAAATGCACTTTCCTGGCAGGACGCGGTGGCTCATGCCCATAAT |
| | CTCAGCACTTTGGGAGGCCTAGGAAGGTGGATCACCTGAGGTCC |
| | GGAGTTCAAGACTAACCTGGCCAACATGGTGAAACCCAGTATCT |
| | ACTAAAAAATACAAAAAAAAAAAAAAAAGAAGAAGAAGAAGA |
| | AGAAAATAAAGAAAAGTTAGCCGGGCGTGGTGTCGCGCGCCTGT |
| | AATCCCAGCTACTCCAGAGGCTGCGGCAGGAGAATCGCTTGAGC |
| | CCGGGAGGCAGAGGTTGCATTAAGCCAAGATCGCCCAATGCACT |
| | CCGGCCTGGGCGACAGAGCAAGACTCCGTCTCAAAAAATAATAA |
| | TAATAAATAAAAATAAAAAATAAAATGGATTTCCCAGCATCTCT |
| | GGAAAAATAGGCAAGTGTGGCCATGATGGTCCTTAGATCTCCTC |
| | TAGGAAAGCAGACATTTATTACTTGGCTTCTGTGCACTATCTGAG |
| | CTGCCACGTATTGGGCTTCCACCCCTGCCTGTGTGGACAGCATGG |
| | GTTGTCAGCAGAGTTGTGTTTTGTTTTGTTTTTTTGAGACAGAGTT |
| | TCCCTCTTGTTGCCCAGGCTGGAGTGCAGTGGCTCAGTCTCAGCT |
| | CACTGCAACCTCTGCCTCCTGGGTTCAAGTGATTCTCCTGCCTCA |
| | GCCTCCCGAGTAGCTGGGATTATCGGCTAATTTTGTATTTTTAGT |
| | AGAGACAGATTTCTCCATGTTGGTCAGGCTGGTCTCGAACTCCCA |
| | ACCTCAGGTGATCCGCCCACCTCGCCCTCCCAAAGTGCTGGAATT |
| | ACAGGCGTGAGCCACCGCGTCTGGCCATCAGCAGAGTTTTTAAT |
| | TTAGGAGAATGACAAGAGGTGGTACAGTTTTTTAGATGGTACCT |
| | GGTGGCTGTTAAGGGCTATTGACTGACAAACACACCCAACTTGG |
| | CGCTGCCGCCCAGGAGGTGGACACTGGGTTTCTGGATAGATGGT |
| | TAGCAACCTCTGTCACCAGCTGGGCCTCTTTTTTTTCTATACTGAA |
| | TTAATCACATTTGTTTAACCTGTCTGTTCCATAGTTCCCTTGCACA |
| | TCTTGGGTATTTGAGGAGTTGGGTGGGTGGCAGTGGCAACTGGG |
| | GCCACCATCCTGTTTAATTATTTTAAAGCCCTGACTGTCCTGGAT |
| | TGACCCTAAGCTCCCCCTGGTCTCCAAAATTCATCAGAAACTGAG |
| | TTCACTTGAAGGCCTCTTCCCCACCCTTTTCTCCACCCCTTGCATC |
| | TACTTCTAAAGCAGCTGTTCAACAGAAACAGAATGGGAGCCACA |
| | CACATAATTCTACATTTTCTAGTTAAAAAGAAAAAAAAATCATTT |
| | TCAACAATATATTTATTCAACCTAGTACATACAAAATATTATCAT |
| | TCCAACATGTAATCAGTATTTTAAAAATCAGTAATGAGACCAGG |
| | CACGGTGGCTCACGACTGTAATCCCAGGACTTTGGGAGGCCGAG |
| | GCGAGTGGATCATCTGAGATCAGGAGTTCAAGACCAGCCTGGCC |
| | AACATGGTGAAACCCCATCTCTACTAAAAACTAGCTCAGCATGG |
| | TGGTGGGTGCCTGTAGTCCCAGCTACTCGGGAGGCTGAGGCATG |
| | AGAATCACTTGAGCCCAGGAGGCAGAGGTTGCAGTGAGCCAAG |
| | ATTTTGGGGATTCTGTGACATACAAAAAAAATCAGTAATAAGA |
| | TATCTTGCATACTCTTTTCGTACTCATATACTTCCAGCATATCTCA |
| | ATTCACAATTTCTAAGTAAATGCTCTATCTGTATTTACTTTTATAA |
| | AATTCACAATTAAAAATGAAGGTTCACATAGTCAAGTTGTTCCA |
| | AACACACTTAAATGTCTCCTAGGCTGGGTGTGGTTGCTCACACCT |
| | GTAATCCCAGCACTTTGGGAGGCTGAGATGGGCGGATCACCTGA |

TABLE 1-continued

FXN intron 1 target nucleic acid sequences

| Target Region | Sequence (5'-3') |
|---|---|
| | GGTCAGGAGTTTGAGACCAGCCTGGCCAACATGGTGAAACCCCG |
| | TCTCTACTAAAAATACAAAAATTAGCTGGATGTGGTGGCACTCA |
| | CCTGTAATCCCAGCTACTCAGGAGGCTGAGGCAGGATAATTGCT |
| | TGAACCCGGGAGGTGGTGGAGGTTGCAGTGAGCCGAGATCGCAC |
| | CACTGCCTTCCAACCTGGGCGACAGAGCGAGACTCCGTCTCAAA |
| | AAAAAAAAAAAGGCTCCTAATAACTTTATTACTTTATTATCACCT |
| | CAAATAATTAAAATTAAATGAAGTTGAAAATCCAGGTCCTCAGT |
| | CCCATTAGCCACATTTCTAGTGCTCAGTAGCCACGGGGCTGGTG |
| | ACCACCACATGGGACAGCATATTTAGTACCTGATCATTGGTTCTC |
| | AGATCTGGCTACTCAGCAGAACCAAGAATCCACAGAAACGGCTT |
| | TTAAAAGCACAGCCCCACAGCCCCCAGCCCCAGCCTTACCTACC |
| | TGGAGGCTGGGAAGGACTCTGATTCCACGAGGCAGCCTATGTTT |
| | TTTGATGGAGGGATGTGACAGGGGCTGCATCTTTAACGTTTCCTC |
| | TTAAATACTGGAGACAGCTTCGAGGAGGAGATAACTGGATGTGT |
| | CTTAGTCCATTTGATGGAGGGATGTGACGGGGCTGCGTCTTTAAC |
| | GTTTCCTCTTAAATACCGGAGACAGCTTCGAGAAGGAGATAACT |
| | GGATGTTTCTTAGTCCATTTTCTGTTGCTTGTGACAGAATACCTG |
| | AAACTGGGCAATTTATATGGTAAAAAATTTTCTTCTTACTGCTCT |
| | GGAGGCTGAGAAGTCCAAAGTCAAGTCCCTTCTTGCTGGTGGGG |
| | ACTTTGCAGAGTATTGAGGCGGCACCGGGCGTCATATGGTAAGG |
| | GGCTGAGTGTGCTACCTCAGGTGTCTTTTTCTTTTCTTATAAAGCC |
| | TAACTAGTTTCACTCCCATGATAACCCATTAATCTATGAATGGAT |
| | TAATCCATTATTGAGGGAAGAACCTTCATGACCCAGTCACCGCTT |
| | AAAGGCCCCACCTCTCAATACTGCCACATCGGGAATTAAGTTTC |
| | AACATGAGTTTCGGAGGTGACAAACATTCAAACCATAGCATGCT |
| | GTCTCTTAAATGACTCAATAAGCTCCTGTGGCATCCACTTCTGCA |
| | TGCCTTGGGCAGCTTTTAGACATCTGTCCATTTTCCTAGAGGGAC |
| | AAGACCACCACCTGTGATCCTATGACCTTTTGGCTTTAGGCCTAA |
| | CAAGCAGGTTATACCCTCACTCACTTTCAAATCATTTTTATTGTCT |
| | TGCAGACAATTTACACAAGTTTACACATAGAAAAGGATATGTAA |
| | ATATTTATACGCTGCCGGGCGCGGTGGCTCACGCCTGTAATCCCA |
| | GCACTTTGGGAGGCCGAGGCAGGTGGATCACGAGTTCAGGAGAT |
| | GGAGACCATCCTGGCTAATACGATGAAACCCCATCTCTACTAAA |
| | AATACAAAAAATTAGCCGGGCGTGGTGACGGGTGCCTGTAGTCC |
| | CCACTACTCGGGACGCTGAGGCAGGAGAATGGCGTGAACCCGGG |
| | AGGCAGAGCTTGCAGTGATCCGAGATCGTGCCACTGCACTCCAG |
| | CCTGGGTGACAGAGCGAGACTGCATCTCAAAGAAAAAAATAAAT |
| | AAATAAATAAATATTTATACTGCTTATAAACTAATAATAAATGCT |
| | ATGGTCTGCATGTTTGTGTCACCCCACCATTCATATGTTAAAACC |
| | TAATCACCAAAGTGATATTAGGAGGTGGGGCCCTTGGGAGGTGA |
| | TGAGGTATGAGGGTGGAGCCCATATGATTGGGATTAGTGCCCTT |
| | CTAAAATAGCCCAACGGAGCCCAGTGACAAGGCATCATCTATGA |
| | ACCAGGAAACTGGCCCTCACCAGACACCAAAGCTGTTGGTGCAT |
| | TGATCTTGGATTTCCCACCCTCCAGGACTCTAAGAAACACATTTC |
| | TATTGTTTATAAGCCACCCAGTGGCTGGTATTTTGTTATAACATC |
| | CCAGACTAAGACAAATAACAAATACTTGTATCCCTGACACCAGG |
| | TTAAGAGATAGAATTTGTTTGTTCCTCTGGAGGCCCTTGTCTTCA |
| | CCCCATCACTGCCCTGTCCTCCCTGGAGGAATCTGCCAGCCCGAA |
| | TTCTGTTCATCGTACCCTCCTTTTCTTAGAGTTTGACCTCCTCTGT |
| | ATCTCCCCCAATCCATGTATTGCTTATATACAAGGTATTCTGCTG |
| | TATCTGTTCTGCTATGGCTTGCCCCTTTTGTTCAACACTGTTTTTG |
| | TGCGTCATCTGCATTGATGCATGCAGTTGTCCTTTATTTGTTCTCA |
| | CTGCTGGATAGTATCTGGTTGGGTAAATATATCACACTGTAAATC |
| | ACACTATCCAGGTTCCTTTAGGTGACATTTGGTTGATTGCAGTGT |
| | TCTGTTGTTACGATGGTGCTGCTGTGACTGTTCTTGTGCATGGAC |
| | AGAAGTTCCTTTCAGGTGAATTTCTCAGAATGGAATTGCTGGGCA |
| | AAGGGGCAGCCAATAATCAACTCATTTGATGCCAAAAGTGGTGG |
| | TGCCAGTTCATCCTCCCCTGCGAGGTATGGGTCCTGATTCACTCT |
| | TCAAGTGCTGTGGTTTGACAGGGCCGGGGGTGACAAGGGGACAC |
| | CTGGGAAGGAAAGCTGGGCTCCCTGCTGGCCATCCAGGCCAGTC |
| | CTTACCAGGGGGTAGGCAATGATTGGGTCAAGTGGTTCCTGACC |
| | ACTGGGCCTGAGACTTCAGGCCCAGAAACTATCTAATATTTCCTC |
| | AAATGCATCCCATGAGCAGGCACTGTGTGAGTGAGCACACACAT |
| | CTGAAGCCTCAAGCTAGGCAAGCCTACCATGACTTGTGGTCCAA |
| | GGGCTCACGGGTGACCTGGAGTTAGAGGGAGACATGGCTGCCAG |
| | GTGGCTTTAGAAAGAACACTCATCATGGCCAGGTGCGGTGGCTT |
| | ACGCCTGTAATCCCAGCACTTTGGGAGGCCAAGGTGGGTGGATC |
| | ATGAGGTCAGGAGTGAGACCAGCCTGACCAACATGCTGAAACCT |
| | GTCTCTCCTAAAAACACAAAAATTAGCTGGGCATGGAGGTGCAC |
| | GCCTGTAATCCCAGCTACTCAGGAGGCTGAGGCAGGAGAATCAC |
| | TTGAACCCGGGAGGCGGAGGTTGCAATAAGCCTAGATTGTGCCA |
| | CTGCATTCCAGCCTGGGCAACAGAGCAAGACTCCGTCTCAGAAA |
| | AAAAAAAAAAAGGAAGAACACTCATCCTATGACCTTGACCTCC |
| | AAGCTTTGCCTCCCTCAAGCAGAACAGAATGGAGCCTCCCTTAG |
| | GCAGAGGCGGAAGTTTGCCTCTCACCTAGTTCTCCATTCTTTTGT |
| | TCAGAGCCTGAATACCCTCAGGCTCTGTACTTGGGGTATTTCTGT |

TABLE 1-continued

FXN intron 1 target nucleic acid sequences

| Target Region | Sequence (5'-3') |
|---|---|
| | TCTCTTGTTTTATGCTCACGGTTGTGAGGTTTGTTGTGAGTACCAC |
| | GATCCCTTCCTTCAGAGGAGTAAACTGAGGTTCCAAAAGGTTTA |
| | GCAGTTGCCCGAGGAATATTAAATTGGCAAAAGCAGGTAGAATA |
| | TAAAGCAAGGAGTATTTGGCAACGGTTCTTTTTTATGATTAAAAA |
| | CAGCCGAAGAAAGACTTCTACTTGTGCCTTTGAAGGAGTAACTG |
| | CATTTGACCTTCCCACCAGTAACAACCATCAAATCTCTATTAAAT |
| | TAAACACACACACACACAAACAAAAACAGCTATTGTGAAGGTAT |
| | CAGCGACTAAGACAACTAAGGTTTGAGGGGCCAGGATCCTGGAG |
| | AGATGGAAACTTCCCTGAGGTGAGCCCCACATTCTCAGACACTTT |
| | TCCTTGGATGTTTTGAGCACTGCTTTAATTCCTGGGAAAACAATT |
| | CCTTCCACTGTGCACAGACTCTGGGGCCAGACAGCTTGGGTTCA |
| | ATCCCAGCTCTGCCACTTAATGTCTGTGTATCTGTGTAGGCAAGT |
| | TACCCTTTGGTGCGTCAGTTTCCTCATCTGTAAAACACAACTATA |
| | GTTGATCCTCATTCGTTAAGAGTCTGTACTTGTTAATTTGCTCACT |
| | TGCTAAAATTTGTTACCCCAAAATCAGTACCCCTAGCCTTTTGGG |
| | GTCGTTTCAAAGATGTGTGCAGAGCGGCAAAAAAATGTGAGCTC |
| | CTCCAGGCTCATGTTCCCAGCCAAGGTCCAACAAAGTGCTGCCCT |
| | GCCTTCTTATTTCAGCTGTCATAGTGTAAACTGTGTCCTTTTCACA |
| | GTCTGATTAGTGCCATGTTTTTCAGATTTTTATGCTTTTTTCTTGG |
| | TTATTTCTCTGTTAAAATTGTCTCCAAGTGTAGTGCAAAGTTTAG |
| | CACGAGGAGGCTGTGATGTTCCTTACAGAGAAAATGCATGTGTT |
| | AGAGAAGCTTTGTCAGGCATGAGTTAAGGTGCTGTTGTCCTGAG |
| | ATCAATTAATTTGTTGTTGTTGTTTGAGACAGGGTCTCCCTCT |
| | GTTGCCCAGGCTGCTGGAGTGCAATGGTGTAATCATAGCTCACT |
| | GCAGCCTCTACCTCTCTGGCTCAAGCAATCCTCCCACCTCGGCCT |
| | CCTGAGTAGCTGGGACTACAGGTACACCCCACCACACCCAGATA |
| | ATGTTTTTGATATTTTTTAGGTGGAATTTTGCTCATCACCCAGGC |
| | TGGAGTGCAATGGTGCGATCCTGGCTCACTGCAACCTCCACCTCC |
| | CGGATTCAAGCAATTCTTCTGCCTCAGCCTCCTGAGTAGCACAGA |
| | TTACAGGCACATGTCATCACGCCTTGCTAATTTTTGTGTTTTTAGT |
| | AGAGGCGGGGTTTCACCATGTTGGCCAGGCTAGTCTTGAACTCCT |
| | GACCTCAGGTGATCCACCCGCCTCCGCTCCCAAACTGCAGAGA |
| | TTATAGGCACGAACCACAATGCCCGGCCTCATGTTTTTTATTTTT |
| | CAAGTTGAAATGAGGTCTCTCTATGTTGCCCAGGTTGGTCTCAAA |
| | CTCTTGAGCTCAAGTAATCCTCCCACCTTGGCCTCCCAAAGTGCG |
| | GGGATTACAGGTGTGAGCTACCATGCCCAGCCAAGATCAGTGTT |
| | AATGAATCAACTATATATATTACATAAGGTGTCTTTAAACAGAA |
| | ATAAGGTTATATATTGATCGATTGTAACAATGTTGTGACCAGCA |
| | GCTTACAGGGTACCTAGCCTTGTATTTCTCCTATAAATAATTTGC |
| | TCGTTGAGTGTTTGTGGCAACTTTGTAGCACATAACTACCAAGAA |
| | TAAGGACTGTAATAAGAGTACGTCCCTCACAGGATTGTAATGAA |
| | GACTGAGTCCATTTACATAAAGGCTGAGAGCAGTGTCAAGCAGA |
| | TGGAGAACACTGTAGAATGTGCGATAGCTCTAACAGTGGTTATC |
| | ATGGCTGCCCTCTCACTTCTTCAGAGACATGTGTTTCTAAGGTCT |
| | GCACTCTGCCCCACCCTCCCCATCCACTGTCCCCAGCCCGTTTC |
| | CTCCTCCACTTACTTCCCAGCCCTGTGCCTTCTGCCTTCTCTTTTC |
| | TGAGTTTGCTAAGGGCACTGCTGGCTCAAGAGCAGTAACTAACA |
| | GTCTCTCGCCTCTTCTCTCCATGGCAACCAGTGACCTTTGGAGAA |
| | TGTAAACCTTATCACCAATCTCTTAAAGCCCTTCGGTGCCTTCCC |
| | AGGATGACGTCCAGCTGAGGTCCTTGGCAAGACCCAGGGCGCCC |
| | CCTCCTCGCTCCATCACCTCCCCTGTCACCTCCCCTGCATCTCCCT |
| | ACTCCAGCTGCACCACTCTTGTGCCCCAGTGGCTCTTGTCTGATT |
| | ATTTCCTTCATCTCCCCAGCTGGTCAGCAGAGCTGGTGGTAATCA |
| | ACTCAGACCCTGTCACCTGGATGTCCAGCAGTTAGGGACTAAAA |
| | AAAATCAACAGGTCACATTCTGTCCTGCAGATCATGATAATAAG |
| | ATCTGTCAGACAGCAGTCAGCAGTCAGAGCCAAATCTTCTGGAC |
| | TTCAGCAGGATTCTGCCTCTTGCTATTTCCTGTTGCCTCTCTTAGT |
| | GACCTTTTAAGAGCATTGTGGATGCCTCCCAGCCTCCTGCTAACC |
| | ACCCTGTAACCTGAACAGCCTGCAGCAGCCCTGCCCAGTAGAAC |
| | TTCCTGATGTGATGGAAATGCTGTGTCTGCACCACTAGCCACATG |
| | TGGCCACAGGATTCTCGAAACTGGTGGTGCAGTTGAGGAGCTGA |
| | CTTTATATTTTATCTCATTAAATTTAAATGTAAATAGCTACGTGT |
| | GGCTTGTTGGCTAGCCTATTGGAAAACACGGGCTTAGAGAGACA |
| | CAGGGAGAATCACTGTAATGCACTAAAAGAAGGTAAAAAAAAA |
| | AAAATCCTAAGAAATATTCCTAAAATACTTTAATATAGGGCTGG |
| | GTGCGGTGGCTCACATCCAGCATTTTGGGAAGCTGAGGAGGGCA |
| | GATCACTTGAGGCCAGGAGTTCAAGACCAGCCTGGCCAACATGG |
| | TGAAACCCCGTCTCTACTAAAAATACAAAAAATCGGGTGCGGTG |
| | GCGGGTGCCTGTAATCCCAGCTACGCGGGAGGCTGAGGCACGAG |
| | AATCACTCGAACCCGGGAGGCGGGGGTTGCAGTGAGCCGAGATC |
| | GTGCCACTGCACTCCAGCCTGGGCGACAGAGCGAGACTTCATCT |
| | CAAAAACAAAAAACAAAAACCAAAAAAAAAACTTCAGCATGA |
| | TTATTTAACCAAAATGCAGGTTAGTTGTTCACCGGATGCAGAGTC |
| | CAATTAACAAGAGCAAGGCCTGGTACCAAAAAAAGTGAATTTAC |
| | TCCGAAACTAGCTTGGGTGAGGGGTACAAAGCATCCTGCCTTTCT |
| | TTAAAAGTGCTGCTTCCCCTTGGAAGTAGAAAGTGGACACTTTTA |

TABLE 1-continued

FXN intron 1 target nucleic acid sequences

| Target Region | Sequence (5'-3') |
|---|---|
| | TAAGGTAAGGGGGGAAGTGTGCAAGGGCAAGTGGGGGGTCCC<br>TCTGCTAGTTCCGTGCATACTCTACAGGACAGTTGACTTGGCACC<br>TTCCTGGTTAGTAATAAGCTGTAGCAGTGGCCAAGTGGGCATGC<br>TTTCAGTATGCCCTCCCAGTGAATGAAAGTCCTGAGGCAACCCCC<br>AAGGGTGGAAGTGCCAGGCCACCACCCACTGGAGGTGAAAGTTC<br>CGTGATGGGTTTGCTTTGGTCTGCGAATCTACTGTCATGTGGAGA<br>GATCTGTGCTCTGGAAGAGCATACAGTTAGAAAAGCTTGCCCTG<br>AAGGGAATGTATGGTGAAGGGGAGGTGAAAGGTTATATTTGCAT<br>TTCTGAAGGGCTAAGTAGGAAACCGGGAACCAGGGGAGAGGAG<br>AAGAGAAGAGAGGATAATTTTTTTTAAGAAAAGCAACATATTCC<br>CTTTTTCTTAGAAAAAATGGAGCACTCGGTTACAGGCACTCGAAT<br>GTAGAAGTAGCAATATATAAATTATGCATTAATGGGTTATAATTC<br>ACTGAAAAATAGTAACGTACTTCTTAACTTTGGCTTTCAGAGTTC<br>GAACCAACGTGGCCTCAACCAGATTTGGAATGTCAAAAAGCAGA<br>GTGTCTATTTGATGAATTTGAGGAAATCTGGAACTTTGGGCCACC<br>CAGG (SEQ ID NO: 1) |
| FXN intron 1<br>(upstream of<br>GAA repeat) | AAGAAAACTTTCACAATTTGCATCCCTTTGTAATATGTAACAGAA<br>ATAAAATTCTCTTTTAAAATCTATCAACAATAGGCAAGGCACGG<br>TGGCTCACGCCTGTCGTCTCAGCACTTTGTGAGGCCCAGGCGGGC<br>AGATCGTTTGAGCCTAGAAGTTCAAGACCACCCTGGGCAACATA<br>GCGAAACCCCCTTTCTACAAAAAATACAAAAACTAGCTGGGTGT<br>GGTGGTGCACACCTGTAGTCCCAGCTACTTGGAAGGCTGAAATG<br>GGAAGACTGCTTGAGCCCGGGAGGGAGAAGTTGCAGTAAGCCA<br>GGACCACACCACTGCACTCCAGCCTGGGCAACAGAGTGAGACTC<br>TGTCTCAAACAAACAAATAAATGAGGCGGGTGGATCACGAGGTC<br>AGTAGATCGAGACCATCCTGGCTAACACGGTGAAACCCGTCTCT<br>ACTAAAAAAAAAAAAAAATACAAAAAATTAGCCAGGCATGGTG<br>GCGGGCGCCTGTAGTCCCAGTTACTCGGGAGGCTGAGGCAGGAG<br>AATGGCGTGAAACCGGGAGGCAGAGCTTGCAGTGAGCCGAGAT<br>CGCACCACTGCCCTCCAGCCTGGGCGACAGAGCGAGACTCCGTC<br>TCAATCAATCAATCAATCAATAAAATCTATTAACAATATTTATTG<br>TGCACTTAACAGGAACATGCCCTGTCCAAAAAAAACTTTACAGG<br>GCTTAACTCATTTTATCCTTACCACAATCCTATGAAGTAGGAACT<br>TTTATAAAACGCATTTTATAAACAAGGCACAGAGAGGTTAATTA<br>ACTTGCCCTCTGGTCACACAGCTAGGAAGTGGGCAGAGTACAGA<br>TTTACACAAGGCATCCGTCTCCTGGCCCCACATACCCAACTGCTG<br>TAAACCCATACCGGCGGCCAAGCAGCCTCAATTTGTGCATGCAC<br>CCACTTCCCAGCAAGACAGCAGCTCCCAAGTTCCTCCTGTTTAGA<br>ATTTTAGAAGCGGCGGGCCACCAGGCTGCAGTCTCCCTTGGGTC<br>AGGGGTCCTGGTTGCACTCCGTGCTTTGCACAAAGCAGGCTCTCC<br>ATTTTTGTTAAATGCACGAATAGTGCTAAGCTGGGAAGTTCTTCC<br>TGAGGTCTAACCTCTAGCTGCTCCCCCACAGAAGAGTGCCTGCG<br>GCCAGTGGCCACCAGGGGTCGCCGCAGCACCCAGCGCTGGAGGG<br>CGGAGCGGGCGGCAGACCCGGAGCAGCATGTGGACTCTCGGGC<br>GCCGCGCAGTAGCCGGCCTCCTGGCGTCACCCAGCCCAGCCCAG<br>GCCCAGACCCTCACCCGGGTCCCGCGGCCGGCAGAGTTGGCCCC<br>ACTCTGCGGCCGCCGTGGCCTGCGCACCGACATCGATGCGACCT<br>GCACGCCCCGCCGCGCAGTAAGTATCCGCGCCGGGAACAGCCGC<br>GGGCCGCACGCCGCGGGCCGCACGCCGCACGCCTGCGCAGGGA<br>GGCGCCGCGCACGCCGGGGTCGCTCCGGGTACGCGCGCTGGACT<br>AGCTCACCCCGCTCCTTCTCAGGGCGGCCCGGCGGAAGCGGCCT<br>TGCAACTCCCTTCTCTGGTTCTCCCGGTTGCATTTACACTGGCTTC<br>TGCTTTCCGAAGGAAAAGGGGACATTTTGTCCTGCGGTGCGACT<br>GCGGGTCAAGGCACGGGCGAAGGCAGGGCAGGCTGGTGGAGGG<br>GACCGGTTCCGAGGGGTGTGCGGCTGTCTCCATGCTTGTCACTTC<br>TCTGCGATAACTTGTTTCAGTAATATTAATAGATGGTATCTGCTA<br>GTATATACATACACATAATGTGTGTGTCTGTGTGTATCTGTATAT<br>AGCGTGTGTGTTGTGTGTGTGTTTGCGCGCACGGGCGCGCGCA<br>CACCTAATATTTTCAAGGCTGGATTTTTTTGAACGAAATGCTTTC<br>CTGGAACGAGGTGAAACTTTCAGAGCTGCAGAATAGCTAGAGCA<br>GCAGGGGCCCTGGCTTTTGGAAACTGACCCGACCTTTATTCCAGA<br>TTCTGCCCCACTCCGCAGAGCTGTGTGACCTTGGGGATTCCCCT<br>AACCTCTCTGAGACGTGGCTTTGTTTTCTGTAGGGAGAAGATAAA<br>GGTGACGCCCATTTTGCGGACCTGGTGTGAGGATTAAATGGGAA<br>TAACATAGATAAAGTCTTCAGAACTTCAAATTAGTTCCCCTTTCT<br>TCCCTTTGGGGGGTACAAAGAAATATCTGACCCAGTTACGCCACG<br>GCTTGAAAGGAGGAAACCCAAAGAATGGCTGTGGGGATGAGGA<br>AGATTCCTCAAGGGGAGGACATGGTATTTAATGAGGGTCTTGAA<br>GATGCCAAGGAAGTGGTAGAGGGTGTTTCACGAGGAGGGAACC<br>GTCTGGGCAAAGGCCAGGAAGGCGGAAGGGGATCCCTTCCAGAG<br>TGGCTGGTACGCCGCATGTATTAGGGGAGATGAAAGAGGCAGGC<br>CACGTCCAAGCCATATTTGTGTTGCTCTCCGGAGTTTGTACTTTA<br>GGCTTGAACTTCCCACACGTGTTATTTGGCCCACATTGTGTTTGA<br>AGAAACTTTGGGATTGGTTGCCAGTGCTTAAAAGTTAGGACTTA<br>GAAAATGGATTTCCTGGCAGGACGCGGTGGCTCATGCCCATAAT |

TABLE 1-continued

FXN intron 1 target nucleic acid sequences

| Target Region | Sequence (5'-3') |
| --- | --- |
| | CTCAGCACTTTGGGAGGCCTAGGAAGGTGGATCACCTGAGGTCC<br>GGAGTTCAAGACTAACCTGGCCAACATGGTGAAACCCAGTATCT<br>ACTAAAAAATACAAAAAAAAAAAAAAAA (SEQ ID NO: 2) |
| FXN intron 1<br>(downstream of<br>GAA repeat) | AATAAAGAAAAGTTAGCCGGGCGTGGTGTCGCGCGCCTGTAATC<br>CCAGCTACTCCAGAGGCTGCGGCAGGAGAATCGCTTGAGCCCGG<br>GAGGCAGAGGTTGCATTAAGCCAAGATCGCCCAATGCACTCCGG<br>CCTGGGCGACAGAGCAAGACTCCGTCTCAAAAAATAATAATAAT<br>AAATAAAAATAAAAAATAAAATGGATTTCCCAGCATCTCTGGAA<br>AAATAGGCAAGTGTGGCCATGATGGTCCTTAGATCTCCTCTAGG<br>AAAGCAGACATTTATTACTTGGCTTCTGTGCACTATCTGAGCTGC<br>CACGTATTGGGCTTCCACCCCTGCCTGTGTGGACAGCATGGGTTG<br>TCAGCAGAGTTGTGTTTTGTTTTGTTTTTTTGAGACAGAGTTTCCC<br>TCTTGTTGCCCAGGCTGGAGTGCAGTGGCTCAGTCTCAGCTCACT<br>GCAACCTCTGCCTCCTGGGTTCAAGTGATTCTCCTGCCTCAGCCT<br>CCCGAGTAGCTGGGATTATCGGCTAATTTTGTATTTTTAGTAGAG<br>ACAGATTTCTCCATGTTGGTCAGGCTGGTCTCGAACTCCCAACCT<br>CAGGTGATCCGCCCACCTCGCCCTCCCAAAGTGCTGGAATTACA<br>GGCGTGAGCCACCGCGTCTGGCCATCAGCAGAGTTTTTAATTTAG<br>GAGAATGACAAGAGGTGGTACAGTTTTTTAGATGGTACCTGGTG<br>GCTGTTAAGGGCTATTGACTGACAAACACACCCAACTTGGCGCT<br>GCCGCCCAGGAGGTGGACACTGGGTTTCTGGATAGATGGTTAGC<br>AACCTCTGTCACCAGCTGGGCCTCTTTTTTTCTATACTGAATTAAT<br>CACATTTGTTTAACCTGTCTGTTCCATAGTTCCCTTGCACATCTTG<br>GGTATTTGAGGAGTTGGGTGGGTGGCAGTGGCAACTGGGGCCAC<br>CATCCTGTTTAATTATTTTAAAGCCCTGACTGTCCTGGATTGACC<br>CTAAGCTCCCCCTGGTCTCCAAAATTCATCAGAAACTGAGTTCAC<br>TTGAAGGCCTCTTCCCCACCCTTTTCTCCACCCCTTGCATCTACTT<br>CTAAAGCAGCTGTTCAACAGAAACAGAATGGGAGCCACACACAT<br>AATTCTACATTTTCTAGTTAAAAAGAAAAAAAAATCATTTTCAAC<br>AATATATTTATTCAACCTAGTACATACAAAATATTATCATTCCAA<br>CATGTAATCAGTATTTTAAAAATCAGTAATGAGACCAGGCACGG<br>TGGCTCACGACTGTAATCCCAGGACTTTGGGAGGCCGAGGCGAG<br>TGGATCATCTGAGATCAGGAGTTCAAGACCAGCCTGGCCAACAT<br>GGTGAAACCCCATCTCTACTAAAAACTAGCTCAGCATGGTGGTG<br>GGTGCCTGTAGTCCCAGCTACTCGGGAGGCTGAGGCATGAGAAT<br>CACTTGAGCCCAGGAGGCAGAGGTTGCAGTGAGCCAAGATTTTG<br>GGGGATTCTGTGACATACAAAAAAAATCAGTAATAAGATATCTT<br>GCATACTCTTTTCGTACTCATATACTTCCAGCATATCTCAATTCAC<br>AATTTCTAAGTAAATGCTCTATCTGTATTTACTTTTATAAAATTCA<br>CAATTAAAAATGAAGGTTCACATAGTCAAGTTGTTCCAAACACA<br>CTTAAATGTCTCCTAGGCTGGGTGTGGTTGCTCACACCTGTAATC<br>CCAGCACTTTGGGAGGCTGAGATGGGCGGATCACCTGAGGTCAG<br>GAGTTTGAGACCAGCCTGGCCAACATGGTGAAACCCCGTCTCTA<br>CTAAAAATACAAAAATTAGCTGGATGTGGTGGCACTCACCTGTA<br>ATCCCAGCTACTCAGGAGGCTGAGGCAGGATAATTGCTTGAACC<br>CGGGAGGTGGTGGAGGTTGCAGTGAGCCGAGATCGCACCACTGC<br>CTTCCAACCTGGGCGACAGAGCGAGACTCCGTCTCAAAAAAAAA<br>AAAAAGGCTCCTAATAACTTTATTACTTTATTATCACCTCAAATA<br>ATTAAAATTAAATGAAGTTGAAAATCCAGGTCCTCAGTCCCATT<br>AGCCACATTTCTAGTGCTCAGTAGCCACGGGGCTGGTGACCAC<br>CACATGGGACAGCATATTTAGTACCTGATCATTGGTTCTCAGATC<br>TGGCTACTCAGCAGAACCAAGAATCCACAGAAACGGCTTTTAAA<br>AGCACAGCCCCACAGCCCCCAGCCCCAGCCTTACCTACCTGGAG<br>GCTGGGAAGGACTCTGATTCCACGAGGCAGCCTATGTTTTTTGAT<br>GGAGGGATGTGACAGGGGCTGCATCTTTAACGTTTCCTCTTAAAT<br>ACTGGAGACAGCTTCGAGGAGGAGATAACTGGATGTGTCTTAGT<br>CCATTTGATGGAGGGATGTGACGGGGCTGCGTCTTTAACGTTTCC<br>TCTTAAATACCGGAGACAGCTTCGAGAAGGAGATAACTGGATGT<br>TTCTTAGTCCATTTTCTGTTGCTTGTGACAGAATACCTGAAACTG<br>GGCAATTTATATGGTAAAAAATTTTCTTCTTACTGCTCTGGAGGC<br>TGAGAAGTCCAAAGTCAAGTCCCTTCTTGCTGGTGGGACTTTGC<br>AGAGTATTGAGGCGGCACCGGGCGTCATATGGTAAGGGGCTGAG<br>TGTGCTACCTCAGGTGTCTTTTTCTTTTCTTATAAAGCCTAACTAG<br>TTTCACTCCCATGATAACCCATTAATCTATGAATGGATTAATCCA<br>TTATTGAGGGAAGAACCTTCATGACCCAGTCACCGCTTAAAGGC<br>CCCACCTCTCAATACTGCCACATCGGGAATTAAGTTTCAACATGA<br>GTTTCGGAGGTGACAAACATTCAAACCATAGCATGCTGTCTCTTA<br>AATGACTCAATAAGCTCCTGTGGCATCCACTTCTGCATGCCTTGG<br>GCAGCTTTTAGACATCTGTCCATTTTCCTAGAGGGACAAGACCAC<br>CACCTGTGATCCTATGACCTTTTGGCTTTAGGCCTAACAAGCAGG<br>TTATACCCTCACTCACTTTCAAATCATTTTTATTGTCTTGCAGACA<br>ATTTACACAAGTTTACACATAGAAAAGGATATGTAAATATTTAT<br>ACGCTGCCGGGCGCGGTGGCTCACGCCTGTAATCCCAGCACTTT<br>GGGAGGCCGAGGCAGGTGGATCACGAGTTCAGGAGATGGAGAC<br>CATCCTGGCTAATACGATGAAACCCCATCTCTACTAAAAATACA |

TABLE 1-continued

FXN intron 1 target nucleic acid sequences

| Target Region | Sequence (5'-3') |
|---|---|
| | AAAAATTAGCCGGGCGTGGTGACGGGTGCCTGTAGTCCCCACTA |
| | CTCGGGACGCTGAGGCAGGAGAATGGCGTGAACCCGGGAGGCA |
| | GAGCTTGCAGTGATCCGAGATCGTGCCACTGCACTCCAGCCTGG |
| | GTGACAGAGCGAGACTGCATCTCAAAGAAAAAAATAAATAAAT |
| | AAATAAATATTTATACTGCTTATAAACTAATAATAAATGCTATGG |
| | TCTGCATGTTTGTGTCACCCCACCATTCATATGTTAAAACCTAAT |
| | CACCAAAGTGATATTAGGAGGTGGGGCCCTTGGGAGGTGATGAG |
| | GTATGAGGGTGGAGCCCATATGATTGGGATTAGTGCCCTTCTAA |
| | AATAGCCCAACGGAGCCCAGTGACAAGGCATCATCTATGAACCA |
| | GGAAACTGGCCCTCACCAGACACCAAAGCTGTTGGTGCATTGAT |
| | CTTGGATTTCCCACCCTCCAGGACTCTAAGAAACACATTTCTATT |
| | GTTTATAAGCCACCCAGTGGCTGGTATTTTGTTATAACATCCCAG |
| | ACTAAGACAAATAACAAATACTTGTATCCCTGACACCAGGTTAA |
| | GAGATAGAATTTGTTTGTTCCTCTGGAGGCCCTTGTCTTCACCCC |
| | ATCACTGCCCTGTCCTCCCTGGAGGAATCTGCCAGCCCGAATTCT |
| | GTTCATCGTACCCTCCTTTTCTTAGAGTTTGACCTCCTCTGTATCT |
| | CCCCCAATCCATGTATTGCTTATATACAAGGTATTCTGCTGTATC |
| | TGTTCTGCTATGGCTTGCCCCTTTTGTTCAACACTGTTTTTGTGCG |
| | TCATCTGCATTGATGCATGCAGTTGTCCTTTATTTGTTCTCACTGC |
| | TGGATAGTATCTGGTTGGGTAAATATATCACACTGTAAATCACAC |
| | TATCCAGGTTCCTTTAGGTGACATTTGGTTGATTGCAGTGTTCTG |
| | TTGTTACGATGGTGCTGCTGTGACTGTTCTTGTGCATGGACAGAA |
| | GTTCCTTTCAGGTGAATTTCTCAGAATGGAATTGCTGGGCAAAGG |
| | GGCAGCCAATAATCAACTCATTTGATGCCAAAAGTGGTGGTGCC |
| | AGTTCATCCTCCCCTGCGAGGTATGGGTCCTGATTCACTCTTCAA |
| | GTGCTGTGGTTTGACAGGGCCGGGGGTGACAAGGGGACACCTGG |
| | GAAGGAAAGCTGGGCTCCCTGCTGGCCATCCAGGCCAGTCCTTA |
| | CCAGGGGGTAGGCAATGATTGGGTCAAGTGGTTCCTGACCACTG |
| | GGCCTGAGACTTCAGGCCCAGAAACTATCTAATATTTCCTCAAAT |
| | GCATCCCATGAGCAGGCACTGTGTGAGTGAGCACACACATCTGA |
| | AGCCTCAAGCTAGGCAAGCCTACCATGACTTGTGGTCCAAGGGC |
| | TCACGGGTGACCTGGAGTTAGAGGGAGACATGGCTGCCAGGTGG |
| | CTTTAGAAAGAACACTCATCATGGCCAGGTGCGGTGGCTTACGC |
| | CTGTAATCCCAGCACTTTGGGAGGCCAAGGTGGGTGGATCATGA |
| | GGTCAGGAGTGAGACCAGCCTGACCAACATGCTGAAACCTGTCT |
| | CTCCTAAAAACACAAAAATTAGCTGGGCATGGAGGTGCACGCCT |
| | GTAATCCCAGCTACTCAGGAGGCTGAGGCAGGAGAATCACTTGA |
| | ACCCGGGAGGCGGAGGTTGCAATAAGCCTAGATTGTGCCACTGC |
| | ATTCCAGCCTGGGCAACAGAGCAAGACTCCGTCTCAGAAAAAAA |
| | AAAAAAAAGGAAGAACACTCATCCTATGACCTTGACCTCCAAGC |
| | TTTGCCTCCCTCAAGCAGAACAGAATGGAGCCTCCCTTAGGCAG |
| | AGGCGGAAGTTTGCCTCTCACCTAGTTCTCCATTCTTTTGTTCAG |
| | AGCCTGAATACCCTCAGGCTCTGTACTTGGGGTATTTCTGTTCTC |
| | TTGTTTTATGCTCACGGTTGTGAGGTTTGTTGTGAGTACCACGAT |
| | CCCTTCCTTCAGAGGAGTAAACTGAGGTTCCAAAAGGTTTAGCA |
| | GTTGCCCGAGGAATATTAAATTGGCAAAAGCAGGTAGAATATAA |
| | AGCAAGGAGTATTTGGCAACGGTTCTTTTTTATGATTAAAAACAG |
| | CCGAAGAAAGACTTCTACTTGTGCCTTTGAAGGAGTAACTGCATT |
| | TGACCTTCCCACCAGTAACAACCATCAAATCTCTATTAAATTAAA |
| | CACACACACACACAAACAAAAACAGCTATTGTGAAGGTATCAGC |
| | GACTAAGACAACTAAGGTTTGAGGGGCCAGGATCCTGGAGAGAT |
| | GGAAACTTCCCTGAGGTGAGCCCCACATTCTCAGACACTTTTCCT |
| | TGGATGTTTTGAGCACTGCTTTAATTCCTGGGAAAACAATTCCTT |
| | CCACTGTGCACAGACTCTGGGGCCAGACAGCTTGGGTTCAATCC |
| | CAGCTCTGCCACTTAATGTCTGTGTATCTGTGTAGGCAAGTTACC |
| | CTTTGGTGCGTCAGTTTCCTCATCTGTAAAACACAACTATAGTTG |
| | ATCCTCATTCGTTAAGAGTCTGTACTTGTTAATTTGCTCACTTGCT |
| | AAAATTTGTTACCCCAAATCAGTACCCCTAGCCTTTTGGGGTCG |
| | TTTCAAAGATGTGTGCAGAGCGGCAAAAAAATGTGAGCTCCTCC |
| | AGGCTCATGTTCCCAGCCAAGGTCCAACAAAGTGCTGCCCTGCC |
| | TTCTTATTTCAGCTGTCATAGTGTAAACTGTGTCCTTTTCACAGTC |
| | TGATTAGTGCCATGTTTTTCAGATTTTTATGCTTTTTTCTTGGTTA |
| | TTTCTCTGTTAAAATTGTCTCCAAGTGTAGTGCAAAGTTTAGCAC |
| | GAGGAGGCTGTGATGTTCCTTACAGAGAAAATGCATGTGTTAGA |
| | GAAGCTTTGTCAGGCATGAGTTAAGGTGCTGTTGTCCTGAGATCA |
| | ATTAATTTGTTGTTGTTGTTTGAGACAGGGTCTCCCTCTGTTG |
| | CCCAGGCTGCTGGAGTGCAATGGTGTAATCATAGCTCACTGCAG |
| | CCTCTACCTCTCTGGCTCAAGCAATCCTCCCACCTCGGCCTCCTG |
| | AGTAGCTGGGACTACAGGTACACCCCACCACACCCAGATAATGT |
| | TTTTGATATTTTTTAGGTGGAATTTTGCTCATCACCCAGGCTGG |
| | AGTGCAATGGTGCGATCCTGGCTCACTGCAACCTCCACCTCCCGG |
| | ATTCAAGCAATTCTTCTGCCTCAGCCTCCTGAGTAGCACAGATTA |
| | CAGGCACATGTCATCACGCCTTGCTAATTTTTGTGTTTTTAGTAG |
| | AGGCGGGGTTTCACCATGTTGGCCAGGCTAGTCTTGAACTCCTGA |
| | CCTCAGGTGATCCACCCGCCTCCGCCTCCCAAACTGCAGAGATTA |
| | TAGGCACGAACCACAATGCCCGGCCTCATGTTTTTTATTTTTCAA |

TABLE 1-continued

FXN intron 1 target nucleic acid sequences

| Target Region | Sequence (5'-3') |
|---|---|
| | GTTGAAATGAGGTCTCTCTATGTTGCCCAGGTTGGTCTCAAACTC<br>TTGAGCTCAAGTAATCCTCCCACCTTGGCCTCCCAAAGTGCGGG<br>ATTACAGGTGTGAGCTACCATGCCCAGCCAAGATCAGTGTTAAT<br>GAATCAACTATATATATTACATAAGGTGTCTTTAAACAGAAATA<br>AGGTTATATATTGATCGATTGGTAACAATGTTGTGACCAGCAGCT<br>TACAGGGTACCTAGCCTTGTATTTCTCCTATAAATAATTTGCTCG<br>TTGAGTGTTTGTGGCAACTTTGTAGCACATAACTACCAAGAATAA<br>GGACTGTAATAAGAGTACGTCCCTCACAGGATTGTAATGAAGAC<br>TGAGTCCATTTACATAAAGGCTGAGAGCAGTGTCAAGCAGATGG<br>AGAACACTGTAGAATGTGCGATAGCTCTAACAGTGGTTATCATG<br>GCTGCCCTCTCACTTCTTCAGAGACATGTGTTTCTAAGGTCTGCA<br>CTCTGCCCCACCCTCCCCATCCACTGTCCCCCAGCCCGTTTCCTCC<br>TCCACTTACTTCCCAGCCCTGTGCCTTCTGCCTTCTCTTTTCTGAG<br>TTTGCTAAGGGCACTGCTGGCTCAAGAGCAGTAACTAACAGTCT<br>CTCGCCTCTTCTCTCCATGGCAACCAGTGACCTTTGGAGAATGTA<br>AACCTTATCACCAATCTCTTAAAGCCCTTCGGTGCCTTCCCAGGA<br>TGACGTCCAGCTGAGGTCCTTGGCAAGACCCAGGGCGCCCCCTC<br>CTCGCTCCATCACCTCCCCTGTCACCTCCCCTGCATCTCCCTACTC<br>CAGCTGCACCACTCTTGTGCCCCAGTGGCTCTTGTCTGATTATTT<br>CCTTCATCTCCCCAGCTGGTCAGCAGAGCTGGTGGTAATCAACTC<br>AGACCCTGTCACCTGGATGTCCAGCAGTTAGGGACTAAAAAAAA<br>TCAACAGGTCACATTCTGTCCTGCAGATCATGATAATAAGATCTG<br>TCAGACAGCAGTCAGCAGTCAGAGCCAAATCTTCTGGACTTCAG<br>CAGGATTCTGCCTCTTGCTATTTCCTGTTGCCTCTCTTAGTGACCT<br>TTTAAGAGCATTGTGGATGCCTCCCAGCCTCCTGCTAACCACCCT<br>GTAACCTGAACAGCCTGCAGCAGCCCTGCCCAGTAGAACTTCCT<br>GATGTGATGGAAATGCTGTGTCTGCACCACTAGCCACATGTGGC<br>CACACAGGATTCTCGAAACTGGTGGTGCAGTTGAGGAGCTGACTTT<br>ATATTTTATCTCATTAAATTTAAATGTAAATAGCTACGTGTGGCT<br>TGTTGGCTAGCCTATTGGAAAACACGGGCTTAGAGAGACACAGG<br>GAGAATCACTGTAATGCACTAAAAGAAGGTAAAAAAAAAAAAA<br>TCCTAAGAAATATTCCTAAAATACTTTAATATAGGGCTGGGTGCG<br>GTGGCTCACATCCAGCATTTTGGGAAGCTGAGGAGGGCAGATCA<br>CTTGAGGCCAGGAGTTCAAGACCAGCCTGGCCAACATGGTGAAA<br>CCCCGTCTCTACTAAAAATACAAAAAATCGGGTGCGGTGGCGGG<br>TGCCTGTAATCCCAGCTACGCGGGAGGCTGAGGCACGAGAATCA<br>CTCGAACCCGGGAGGCGGGGGTTGCAGTGAGCCGAGATCGTGCC<br>ACTGCACTCCAGCCTGGGCGACAGAGCGAGACTTCATCTCAAAA<br>ACAAAAAACAAAAACCAAAAAAAAAAACTTCAGCATGATTATTT<br>AACCCAAAATGCAGGTTAGTTGTTCACCGGATGCAGAGTCCAATT<br>AACAAGAGCAAGGCCTGGTACCAAAAAAAGTGAATTTACTCCGA<br>AACTAGCTTGGGTGAGGGGTACAAAGCATCCTGCCTTTCTTTAAA<br>AGTGCTGCTTCCCCTTGGAAGTAGAAAGTGGACACTTTTATAAG<br>GTAAGGGGGGAAGTGTGCAAGGGCAAGTGGGGGGGTCCCTCTG<br>CTAGTTCCGTGCATACTCTACAGGACAGTTGACTTGGCACCTTCC<br>TGGTTAGTAATAAGCTGTAGCAGTGGCCAAGTGGGCATGCTTTC<br>AGTATGCCCTCCCAGTGAATGAAAGTCCTGAGGCAACCCCCAAG<br>GGTGGAAGTGCCAGGCCACCACCCACTGGAGGTGAAAGTTCCGT<br>GATGGGTTTGCTTTGGTCTGCGAATCTACTGTCATGTGGAGAGAT<br>CTGTGCTCTGGAAGAGCATACAGTTAGAAAAGCTTGCCCTGAAG<br>GGAATGTATGGTGAAGGGGAGGTGAAAGGTTATATTTGCATTTC<br>TGAAGGGCTAAGTAGGAAACCGGGAACCAGGGGAGAGGAGAAG<br>AGAAGAGAGGATAATTTTTTTTAAGAAAAGCAACATATTCCCTTT<br>TTCTTAGAAAAAATGGAGCACTCGGTTACAGGCACTCGAATGTA<br>GAAGTAGCAATATATAAATTATGCATTAATGGGTTATAATTCACT<br>GAAAAATAGTAACGTACTTCTTAACTTTGGCTTTCAGAGTTCGAA<br>CCAACGTGGCCTCAACCAGATTTGGAATGTCAAAAAGCAGAGTG<br>TCTATTTGATGAATTTGAGGAAATCTGGAACTTTGGGCCACCCAG<br>G (SEQ ID NO: 3) |
| FXN intron 1 (upstream of GAA repeat - partial sequence 1) | CCCCTTTCTTCCTTTGGGGGGTACAAAGAAATATCTGACCCAGTT<br>ACGCCACGGCTTGAAAGGAGGAAACCCAAAGAATGGCTGTGGG<br>GATGAGGAAGATTCCTCAAGGGGAGGACATGGTATTTAATGAGG<br>GTCTTGAAGATGCCAAGGAAGTGGTAGAGGGTGTTTCACGAGGA<br>GGGAACCGTCTGGGCAAAGGCCAGGAAGGCGGAAGGGGATCCC<br>TTCAGAGTGGCTGGTACGCCGCATGTATTAGGGGAGATGAAAGA<br>GGCAGGCCACGTCCAAGCCATATTTGTGTTGCTCTCCGGAGTTTG<br>TACTTTAGGCTTGAACTTCCCACACGTGTTATTTGGCCCACATTG<br>TGTTTGAAGAAACTTTGGGATTGGTTGCCAGTGCTTAAAAGTTAG<br>GACTTAGAAAATGGATTTCCTGGCAGGACGCGGTGGCTCATGCC<br>CATAATCTCAGCACTTTGGGAGGCCTAGGAAGGTGGATCACCTG<br>AGGTCCGGAGTTCAAGACTAACCTGGCCAACATGGTGAAACCCA<br>GTATCTACTAAAAATACAAAAAAAAAAAAAAA (SEQ ID NO: 4) |

TABLE 1-continued

FXN intron 1 target nucleic acid sequences

| Target Region | Sequence (5'-3') |
| --- | --- |
| FXN intron 1 (upstream of GAA repeat - partial sequence 2) | AGGCCAGGAAGGCGGAAGGGGATCCCTTCAGAGTGGCTGGTAC GCCGCATGTATTAGGGGAGATGAAAGAGGCAGGCCACGTCCAA GCCATATTTGTGTTGCTCTCCGGAGTTTGTACTTTAGGCTTGAAC TTCCCACACGTGTTATTTGGCCCACATTGTGTTTGAAGAAACTTT GGGATTGGTTGCCAGTGCTTAAAAGTTAGGACTTAGAAAATG (SEQ ID NO: 5) |
| FXN intron 1 (upstream of GAA repeat - partial sequence 3) | GTATTAGGGGAGATGAAAGAGGCAGGCCACGTCCAAGCCATATT TGTGTTGCTCTCCGGAGTTTGTACTTTAGGCTTGAACTTCCCACA CGTGTTATTTGGCCCACATTGTGTTTGAA (SEQ ID NO: 6) |
| FXN intron 1 (upstream of GAA repeat - partial sequence 4) | TGTTGCTCTCCGGAGTTTGTACTTTAGGCTTGAACTTC (SEQ ID NO: 7) |
| FXN intron 1 (upstream of GAA repeat - partial sequence 5) | GCTCTCCGGAGTTTGTAC (SEQ ID NO: 8) |
| FXN intron 1 (downstream of GAA repeat - partial sequence 1) | TTCACCCCATCACTGCCCTGTCCTCCCTGGAGGAATCTGCCAGCC CGAATTCTGTTCATCGTACCCTCCTTTTCTTAGAGTTTGACCTCCT CTGTATCTCCCCCAATCCATGTATTGCTTATATACAAGGTATTCT GCTGTATCTGTTCTGCTATGGCTTGCCCCTTTTGTTCAACACTGTT TTTGTGCGTCATCTGCATTGATGCATGCAGTTGTCC (SEQ ID NO: 9) |
| FXN intron 1 (downstream of GAA repeat - partial sequence 2) | TCTGTTCATCGTACCCTCCTTTTCTTAGAGTTTGACCTCCTCTGTA TCTCCCCCAATCCATGTATTGCTTATATACAAGGTATTCTGCTGT ATCTGTTCTGCTATGGCTTGCCCCTTT (SEQ ID NO: 10) |
| FXN intron 1 (downstream of GAA repeat - partial sequence 3) | TATCTCCCCCAATCCATGTATTGC (SEQ ID NO: 11) |
| FXN intron 1 (downstream of GAA repeat - partial sequence 4) | CCCCAATCCATGTATTGC (SEQ ID NO: 12) |

The FXN intron 1 target sequences of Table 1 represent the genomic target sequences, however it will be readily understood to those with skill in the art that the antisense compounds of the disclosure will comprise complementarity to the pre-mRNA transcribed from the FXN gene. Thymine nucleotides found in Table 1 will be uracil nucleotides in the context of a pre-mRNA target sequence.

The FXN intron 1 full sequence recited in Table 1 above as SEQ ID NO: 1 has the trinucleotide GAA repeat region in bold and underlined text. The trinucleotide GAA repeat region of SEQ ID NO: 1 above contains 6 GAA repeats, however, it will be readily understood to those with skill in the art that the GAA repeat region can contain between about 1 to about 3,000 or more GAA repeats.

In one aspect, the disclosure provides an antisense oligonucleotide comprising a region of complementarity to an intron of a FXN transcript, wherein the antisense oligonucleotide does not comprise a region of complementarity to another site in a human genome (i.e., the target sequence of the antisense oligonucleotide is unique in a human genome).

In another aspect, the disclosure provides an antisense oligonucleotide comprising a region of complementarity to intron 1 of a FXN transcript, wherein the antisense oligonucleotide does not comprise a region of complementarity to another site in a human genome (i.e., the target sequence of the antisense oligonucleotide is unique in a human genome).

In certain embodiments, the antisense oligonucleotide comprises a region of complementarity to SEQ ID NO: 1. In certain embodiments, the antisense oligonucleotide comprises a region of complementarity that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to SEQ ID NO: 1. In some embodiments, the antisense oligonucleotide comprises a region of complementarity that is perfectly complementary to SEQ ID NO: 1.

In another aspect, the disclosure provides an antisense oligonucleotide comprising a region of complementarity upstream of a trinucleotide repeat of a FXN transcript, wherein: the region of complementarity is within intron 1 of the FXN transcript; and the antisense oligonucleotide does not comprise a region of complementarity to another site in a human genome.

In certain embodiments, the antisense oligonucleotide comprises a region of complementarity to SEQ ID NO: 2. In certain embodiments, the antisense oligonucleotide comprises a region of complementarity that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to SEQ ID NO: 2. In some embodiments, the antisense oligonucleotide comprises a region of complementarity that is perfectly complementary to SEQ ID NO: 2.

In certain embodiments, the antisense oligonucleotide comprises a region of complementarity to SEQ ID NO: 4. In certain embodiments, the antisense oligonucleotide comprises a region of complementarity that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to SEQ ID NO: 4. In some embodiments, the antisense oligonucleotide comprises a region of complementarity that is perfectly complementary to SEQ ID NO: 4.

In certain embodiments, the antisense oligonucleotide comprises a region of complementarity to SEQ ID NO: 5. In certain embodiments, the antisense oligonucleotide comprises a region of complementarity that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to SEQ ID NO: 5. In some embodiments, the antisense oligonucleotide comprises a region of complementarity that is perfectly complementary to SEQ ID NO: 5.

In certain embodiments, the antisense oligonucleotide comprises a region of complementarity to SEQ ID NO: 6. In certain embodiments, the antisense oligonucleotide comprises a region of complementarity that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to SEQ ID NO: 6. In some embodiments, the antisense oligonucleotide comprises a region of complementarity that is perfectly complementary to SEQ ID NO: 6.

In certain embodiments, the antisense oligonucleotide comprises a region of complementarity to SEQ ID NO: 7. In certain embodiments, the antisense oligonucleotide comprises a region of complementarity that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to SEQ ID NO: 7. In some embodiments, the antisense oligonucleotide comprises a region of complementarity that is perfectly complementary to SEQ ID NO: 7.

In certain embodiments, the antisense oligonucleotide comprises a region of complementarity to SEQ ID NO: 8. In certain embodiments, the antisense oligonucleotide comprises a region of complementarity that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to SEQ ID NO: 8. In some embodiments, the antisense oligonucleotide comprises a region of complementarity that is perfectly complementary to SEQ ID NO: 8.

In one aspect, the disclosure provides an antisense oligonucleotide comprising a region of complementarity downstream of a trinucleotide repeat of a FXN transcript, wherein the region of complementarity is within intron 1 of the FXN transcript.

In certain embodiments, the antisense oligonucleotide comprises a region of complementarity to SEQ ID NO: 3. In certain embodiments, the antisense oligonucleotide comprises a region of complementarity that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to SEQ ID NO: 3. In some embodiments, the antisense oligonucleotide comprises a region of complementarity that is perfectly complementary to SEQ ID NO: 3.

In certain embodiments, the antisense oligonucleotide comprises a region of complementarity to SEQ ID NO: 9. In certain embodiments, the antisense oligonucleotide comprises a region of complementarity that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to SEQ ID NO: 9. In some embodiments, the antisense oligonucleotide comprises a region of complementarity that is perfectly complementary to SEQ ID NO: 9.

In certain embodiments, the antisense oligonucleotide comprises a region of complementarity to SEQ ID NO: 10. In certain embodiments, the antisense oligonucleotide comprises a region of complementarity that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to SEQ ID NO: 10. In some embodiments, the antisense oligonucleotide comprises a region of complementarity that is perfectly complementary to SEQ ID NO: 10.

In certain embodiments, the antisense oligonucleotide comprises a region of complementarity to SEQ ID NO: 11. In certain embodiments, the antisense oligonucleotide comprises a region of complementarity that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to SEQ ID NO: 11. In some embodiments, the antisense oligonucleotide comprises a region of complementarity that is perfectly complementary to SEQ ID NO: 11.

In certain embodiments, the antisense oligonucleotide comprises a region of complementarity to SEQ ID NO: 12. In certain embodiments, the antisense oligonucleotide comprises a region of complementarity that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to SEQ ID NO: 12. In some embodiments, the antisense oligonucleotide comprises a region of complementarity that is perfectly complementary to SEQ ID NO: 12.

In one aspect, the disclosure provides an antisense oligonucleotide comprising a region of complementarity to a purine-rich sequence within intron 1 of a FXN transcript. A purine-rich sequence is a segment or stretch of nucleotides that as a G/C nucleotide content greater than 50%. In certain embodiments, a purine-rich sequence comprises about 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, or more purine nucleotides. In certain embodiments, a purine-rich sequence comprises about 51% to about 60% purine nucleotides. In certain embodiments, a purine-rich sequence promotes the formation of a DNA:RNA hybrid R-loop. In certain embodiments, the antisense oligonucleotide comprises a region of complementarity to a purine-rich sequence within intron 1 of a FXN transcript that is capable of forming an R-loop.

In certain embodiments, the antisense oligonucleotide comprises a nucleic acid sequence with at least 90% sequence identity to the nucleic acid sequence set forth below:

5'GAUCAAACUCCGGAGAGC 3' (SEQ ID NO: 13),
5'GCAAUACATGGATTGGGG 3' (SEQ ID NO: 14),
5'GCAAUACAUGGAUUGGGG 3'(SEQ ID NO: 15).

In certain embodiments, the antisense oligonucleotide comprises a nucleic acid sequence with at least 90% sequence identity (i.e., 90%, 91%, 92%, 93%, 94%, 95%, 96%, 97%, 98%, 99%, or 100% sequence identity) to the nucleic acid sequence set forth in SEQ ID NO: 13. In certain embodiments, the antisense oligonucleotide comprises a nucleic acid sequence set forth in SEQ ID NO: 13.

In certain embodiments, the antisense oligonucleotide comprises a nucleic acid sequence with at least 90% sequence identity (i.e., 90%, 91%, 92%, 93%, 94%, 95%, 96%, 97%, 98%, 99%, or 100% sequence identity) to the nucleic acid sequence set forth in SEQ ID NO: 14. In certain embodiments, the antisense oligonucleotide comprises a nucleic acid sequence set forth in SEQ ID NO: 14.

In certain embodiments, the antisense oligonucleotide comprises a nucleic acid sequence with at least 90% sequence identity (i.e., 90%, 91%, 92%, 93%, 94%, 95%, 96%, 97%, 98%, 99%, or 100% sequence identity) to the nucleic acid sequence set forth in SEQ ID NO: 15. In certain embodiments, the antisense oligonucleotide comprises a nucleic acid sequence set forth in SEQ ID NO: 15.

In certain embodiments, the antisense oligonucleotide comprises a nucleic acid sequence with at least 90% sequence identity (i.e., 90%, 91%, 92%, 93%, 94%, 95%, 96%, 97%, 98%, 99%, or 100% sequence identity) to the nucleic acid sequence set forth in any one of SEQ ID NOs: 16-42 (i.e., SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

In certain embodiments, the antisense oligonucleotide comprises a nucleic acid sequence set forth in any one of SEQ ID NOs: 16-42 (i.e., SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

In certain embodiments, the antisense oligonucleotide comprises a sequence modification pattern of

[Xs]$_a$[Xs]$_b$[sX]$_c$, wherein

"a" represents an integer between 0-8;
"b" represents an integer between 6-18;
"c" represents an integer between 0-8;
"s" represents a phosphorothioate internucleoside linkage;
"X" is an adenosine, a guanosine, a cytidine, a thymine, or a uracil, wherein X comprises a 2'-O-(2-methoxyethyl) modification or a tricyclo-DNA modification (i.e., each of adenosine, guanosine, cytidine, thymine, and uracil comprises a 2'-O-(2-methoxyethyl) modification or a tricyclo-DNA modification);
"X" is an adenosine, a guanosine, a cytidine, a thymine, or a uracil, wherein X comprises a 2'-deoxy modification (i.e., each of adenosine, guanosine, cytidine, thymine, and uracil comprises a 2'-deoxy modification); and wherein the sum of a, b, and c is greater than or equal to 12.

In certain embodiments, the antisense oligonucleotide comprises a sequence modification pattern of XsXsXsXsXsXsXsXsXsXsXsXsXsXsXsXsX, wherein "s" represents a phosphorothioate internucleoside linkage;
"X" is an adenosine, a guanosine, a cytidine, a thymine, or a uracil, wherein X comprises a 2'-O-(2-methoxyethyl) modification or a tricyclo-DNA modification; and
"X" is an adenosine, a guanosine, a cytidine, a thymine, or a uracil, wherein X comprises a 2'-deoxy modification.

In certain embodiments, the antisense oligonucleotide comprises a sequence modification pattern of XsXsXsXsXsXsXsXsXsXsXsXsXsXsXsXsX, wherein "s" represents a phosphorothioate internucleoside linkage;
"X" is an adenosine, a guanosine, a cytidine, a thymine, or a uracil, wherein X comprises a 2'-O-(2-methoxyethyl) modification; and
"X" is an adenosine, a guanosine, a cytidine, a thymine, or a uracil, wherein X comprises a 2'-deoxy modification.

In certain embodiments, the antisense oligonucleotide comprises a sequence modification pattern of

[Xs]$_d$[sX]$_e$, wherein

"d" represents an integer between 0-40;
"e" represents an integer between 0-40;
"s" represents a phosphorothioate internucleoside linkage;
"X" is an adenosine, a guanosine, a cytidine, a thymine, or a uracil, wherein X comprises a 2'-O-(2-methoxyethyl) modification or a tricyclo-DNA modification; and wherein the sum of d and e is greater than or equal to 10.

In certain embodiments, the antisense oligonucleotide comprises a sequence modification pattern of XsXsXsXsXsXsXsXsXsXsXsXsXsXsXsXsX, wherein "s" represents a phosphorothioate internucleoside linkage; and "X" is an adenosine, a guanosine, a cytidine, a thymine, or a uracil, wherein X comprises a 2'-O-(2-methoxyethyl) modification or a tricyclo-DNA modification.

In certain embodiments, the antisense oligonucleotide comprises a sequence modification pattern of <u>X</u>s<u>X</u>s<u>X</u>s<u>X</u>s<u>X</u>sXsXsXsXsXsXsXsXs<u>X</u>s<u>X</u>s<u>X</u>s<u>X</u>, wherein "s" represents a phosphorothioate internucleoside linkage; and "<u>X</u>" is an adenosine, a guanosine, a cytidine, a thymine, or a uracil, wherein <u>X</u> comprises a 2'-O-(2-methoxyethyl) modification.

In certain embodiments, each cytosine is a 5-methylcytosine.

In one aspect, the disclosure provides an antisense oligonucleotide comprising the sequence <u>G</u>s<u>C</u>s<u>A</u>s<u>A</u>s<u>U</u>sAsCsAsTsGsGsAsTsTs<u>G</u>s<u>G</u>s<u>G</u>, wherein "s" represents a phosphorothioate internucleoside linkage;

"<u>A</u>" is an adenosine comprising a 2'-O-(2-methoxyethyl) modification;

"<u>G</u>" is a guanosine comprising a 2'-O-(2-methoxyethyl) modification;

"<u>C</u>" is a cytidine comprising a 2'-O-(2-methoxyethyl) modification;

"<u>U</u>" is a thymine comprising a 2'-O-(2-methoxyethyl) modification;

"A" is an adenosine comprising a 2'-deoxy modification;
"G" is a guanosine comprising a 2'-deoxy modification;
"C" is a cytidine comprising a 2'-deoxy modification; and
"T" is a thymine comprising a 2'-deoxy modification.

In one aspect, the disclosure provides an antisense oligonucleotide comprising the sequence <u>G</u>s<u>C</u>s<u>A</u>s<u>U</u>s<u>A</u>sCsAsUsGsGsAsUsUs<u>G</u>s<u>G</u>s<u>G</u>, wherein "s" represents a phosphorothioate internucleoside linkage;

"<u>A</u>" is an adenosine comprising a 2'-O-(2-methoxyethyl) modification;

"<u>G</u>" is a guanosine comprising a 2'-O-(2-methoxyethyl) modification;

"<u>C</u>" is a cytidine comprising a 2'-O-(2-methoxyethyl) modification; and

"<u>U</u>" is a thymine comprising a 2'-O-(2-methoxyethyl) modification.

In one aspect, the disclosure provides an antisense oligonucleotide comprising the sequence <u>G</u>s<u>U</u>s<u>A</u>s<u>C</u>s<u>A</u>sAsAsCsUsCsCsGsGsAs<u>G</u>s<u>A</u>s<u>G</u>s<u>C</u>, wherein "s" represents a phosphorothioate internucleoside linkage;

"<u>A</u>" is an adenosine comprising a 2'-O-(2-methoxyethyl) modification;

"<u>G</u>" is a guanosine comprising a 2'-O-(2-methoxyethyl) modification;

"<u>C</u>" is a cytidine comprising a 2'-O-(2-methoxyethyl) modification; and

"<u>U</u>" is a thymine comprising a 2'-O-(2-methoxyethyl) modification.

In another aspect, the disclosure provides a combination comprising one or more antisense oligonucleotides comprising a region of complementarity to a FXN transcript sequence of SEQ ID NO: 2 or 4-8, and one or more antisense oligonucleotides comprising a region of complementarity to a FXN transcript sequence of SEQ ID NO: 3 or 9-12.

In certain embodiments, the two or more antisense oligonucleotides are linked together through a linker. In certain embodiments, the linker is a cleavable linker. In certain embodiments, the cleavable linker degrades when cleaved. In certain embodiments, the cleavable linker is a nuclease-cleavable linker comprising a phosphodiester linkage. In certain embodiments, the nuclease-cleavable linker comprises from about 2 to about 8 nucleotides in length. In certain embodiments, the nuclease-cleavable linker comprises about 6 nucleotides. In certain embodiments, the cleavable linker is cleaved under reducing conditions or changing pH conditions. In certain embodiments, the cleavable linker is cleaved by an intracellular or endosomal nuclease. In certain embodiments, the cleavable linker is cleaved by an intracellular or endosomal protease.

Conjugated Antisense Oligonucleotides

Antisense oligonucleotides can be covalently linked to one or more moieties, ligands, or conjugates which enhance the activity, cellular distribution or cellular uptake of the resulting antisense oligonucleotides. Antisense oligonucleotides can be covalently linked to one or more moieties, ligands, or conjugates which enhance and/or optimize pharmacokinetic parameters. Various pharmacokinetic parameters are absorbance, concentration of a compound in the body, the degree to which a compound permeates the body, the rate of elimination/clearance of a compound, the volume of plasma cleared of a compound per unit time, and others.

Conjugate groups can include hydrophobic moieties. In a certain embodiment, the hydrophobic moiety is selected from the group consisting of fatty acids, steroids, secosteroids, lipids, gangliosides and nucleoside analogs, endocannabinoids, and vitamins. In a certain embodiment, the steroid selected from the group consisting of cholesterol and Lithocholic acid (LCA). In a certain embodiment, the fatty acid selected from the group consisting of Eicosapentaenoic acid (EPA), Docosahexaenoic acid (DHA) and Docosanoic acid (DCA). In a certain embodiment, the vitamin selected from the group consisting of choline, vitamin A, vitamin E, and derivatives or metabolites thereof. In a certain embodiment, the vitamin is selected from the group consisting of retinoic acid and alpha-tocopheryl succinate.

In a certain embodiment, an antisense compound of the disclosure is conjugated to a lipophilic moiety. In one embodiment, the lipophilic moiety is a ligand that includes a cationic group. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. Diverse lipid conjugates can preferentially drive oligonucleotide uptake into different tissues (Biscans et al, Nucleic Acids Res. 2019, 47, 1082-1096).

Additional conjugate groups include carbohydrates, phospholipids, antibodies, peptides, biotin, phenazine, folate, phenanthridine, anthraquinone, acridine, fluoresceins, rhodamines, coumarins, and dyes. In some embodiments, conjugation of a ligand to an antisense oligonucleotide allows recognition by cell-surface receptors (see, e.g., Wolfrum et al., *Nat. Biotechnol.* 2007, 25:1149-1157; Hostetler et al.,

*Antiviral Chem. Chemother.* 2001, 12:61-70; and Prakash et al., *Nucleic Acids Res.* 2014, 42:8796-807). In certain embodiments, the conjugate is a fibronectin type III (FN3) domain, such as a centyrin protein (see, e.g., Goldberg et al., *Protein Eng Des Sel.* 2016, 29(12):563-572). The various moieties, ligands, or conjugates of the disclosure and means to conjugate them to antisense compounds are described in further detail in WO2017/030973A1 and WO2018/031933A2, incorporated herein by reference.

Antisense oligonucleotides can also be modified to have one or more stabilizing groups that are generally attached to one or both termini of antisense oligonucleotides to enhance properties such as, for example, nuclease stability. Included in stabilizing groups are cap structures. These terminal modifications protect the antisense oligonucleotide having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps. Further 3' and 5'-stabilizing groups that can be used to cap one or both ends of an antisense oligonucleotide to impart nuclease stability include those disclosed in WO 03/004602 published on Jan. 16, 2003.

In some embodiments, an antisense oligonucleotide of the present disclosure comprises a conjugate. In one embodiment, an antisense oligonucleotide of the present disclosure comprises a antisense oligonucleotide sequence and a conjugate, wherein the conjugate is linked to the antisense oligonucleotide sequence. In some embodiments, the conjugate is selected from any of the conjugates described herein, for example, a hydrophobic conjugate, a tissue-targeting conjugate, or a conjugate designed to optimize pharmacokinetic parameters. A hydrophobic conjugate useful for conjugating to antisense oligonucleotides of the present disclosure, includes a hexadecyloxypropyl conjugate, a cholesterol conjugate, a polyunsaturated fatty acid conjugate, and others known in the art that can improve cellular uptake of a conjugate antisense oligonucleotide. In some embodiments, the conjugate can be a tissue-targeting conjugate, for example, a carbohydrate conjugate, or a peptide conjugate, or any conjugate known in the art that can target an antisense oligonucleotide of the present disclosure to a specific tissue. In some embodiments, an antisense oligonucleotide of the present disclosure is conjugated with a polyethylene glycol conjugate. In one embodiment, a polyethylene glycol conjugate antisense oligonucleotide optimizes pharmacokinetic properties of the antisense oligonucleotide.

In some embodiments, the present disclosure provides biocleavable analogues of antisense oligonucleotides described herein. In such cases, biocleavable analogues comprise a hydrophobic conjugate that leads to stronger association with cell membranes and a linker. In one embodiment, the linker is a cleavable linker that when cleaved, releases the antisense oligonucleotide, e.g., releases the antisense oligonucleotide into endosomes. In some embodiments, an antisense compound comprises a cleavable linker, wherein the cleavable linker degrades when cleaved. In some embodiments, the linker is a nuclease-cleavable linker comprising a phosphodiester linkage. In some embodiments, the nuclease-cleavable linker comprising a phosphodiester linkage is about 2 to about 8 nucleotides in length. For example, a nuclease-cleavable phosphodiester linker can be 3, 4, 5, 6, 7, 8 nucleotides in length, or longer, e.g., 9, 10, 11, 12, 13, 14, 15, 16, 17, 18 nucleotides in length, or longer. In one embodiment, the nuclease-cleavable linker comprises about 6 nucleotides. In some embodiments, the cleavable linker is cleaved after cellular internalization. In some embodiments, the cleavable linker is cleaved within an endosome. In some embodiments, the cleavable linker is cleaved under reducing conditions. In some embodiments, the cleavable linker is cleaved under changing pH conditions, for example the cleavable linker is cleaved when the pH decreases, or when the pH increases. In some embodiments, the cleavable linker is cleaved by an intracellular nuclease or protease. In some embodiments, the cleavable linker is cleaved by an endosomal nuclease or protease.

Pharmaceutical Compositions and Formulations

Provided herein are pharmaceutical compositions and formulations which include the antisense compounds described herein. For example, the antisense oligonucleotides described herein can be admixed, encapsulated, conjugated or otherwise associated with other molecules, molecule structures or mixtures of compounds. A pharmaceutical composition of the disclosure is formulated to be compatible with its intended route of administration. Examples of routes of of central nervous system administration include intrathecal administration, intraventricular administration or intrastriatal administration. In some embodiments, the administration can employ an implanted device such as an Ommaya reservoir or implanted intrathecal catheter. Examples of systemic administration include intravenous administration, subcutaneous administration, or intramuscular administration. The route of administration will be, in part, dictated by the target tissue for the antisense compounds. Solutions or suspensions used for administration can include the following components: a sterile diluent such as water for injection, saline solution, lactated Ringers solution, Elliotts B solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, carbonates or phosphates and agents for the adjustment of tonicity such as sodium chloride or dextrose. pH can be adjusted with acids or bases, such as hydrochloric acid or sodium hydroxide. The pharmaceutical compositions can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be suitable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, some methods of preparation are vacuum drying and freeze-drying which yields a powder of the active ingredient plus any additional desired ingredient from a previously sterile-filtered solution thereof.

The pharmaceutical compositions and formulations provided herein can, in some embodiments, be conveniently presented in unit dosage form and can be prepared according to conventional techniques. Such techniques can include bringing into association the active ingredients with the pharmaceutical carrier(s) or excipient(s). In general, the formulations can be prepared by uniformly and intimately bringing into association the active ingredients with liquid carriers, finely divided solid carriers, or both, and then, if necessary, shaping the product (e.g., into a specific particle size for delivery). In one embodiment, the pharmaceutical formulations are prepared for intrathecal, intraventricular or intrastriatal administration in an appropriate solvent, e.g., water or normal saline. In another embodiment, the pharmaceutical formulations are prepared for intravenous, subcutaneous or intramuscular administration in an appropriate solvent, e.g., water or normal saline.

An agent of the present disclosure, e.g., an antisense compound targeting a FXN transcript can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

An agent of the present disclosure, e.g., an antisense compound targeting a FXN transcript can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are suitable. Although compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies within a range of circulating concentrations that include the ED50 with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma can be measured, for example, by high performance liquid chromatography.

The pharmaceutical compositions can be included in a container, pack, or dispenser together with instructions for administration.

An antisense compound targeted to a FXN nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a FXN nucleic acid and a pharmaceutically acceptable diluent. In certain embodiments, the pharmaceutically acceptable diluent is PBS. In certain embodiments, the antisense compound is an antisense oligonucleotide.

In certain embodiments, the pharmaceutically acceptable diluent is designed to mimic the composition of cerebrospinal fluid. As such, it can contain divalent salts such as $Mg^+$ and $Ca^+$. Elliotts B solution is a diluent suitable for use in compositions to be delivered into the cerebrospinal fluid. A person of skill in the art will be able to see that other buffer solutions, with variations in the concentrations of different monovalent and divalent ions, can also be suitable as pharmaceutically acceptable diluents.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. A prodrug can include the incorporation of additional nucleosides at one or both ends of an antisense compound which are cleaved by endogenous nucleases within the body, to form the active antisense compound.

Methods of Treatment

The present disclosure provides a method of treating a subject having a FXN-related disorder. Methods of treatment include administering to the subject in need thereof an effective amount of an antisense compound described herein. In certain embodiments, the antisense compound comprises a target-recognition sequence that is sufficiently complementary to a FXN nucleic acid (e.g., a FXN transcript) to direct cleavage of the FXN nucleic acid by RNase H. In certain embodiments, the antisense compound comprises a target-recognition sequence that is sufficiently complementary to a FXN nucleic acid (e.g., a FXN transcript) to increase expression of the FXN nucleic acid.

Methods of treating a subject having a FXN-related disorder are useful in treating any FXN-related disorder known to those of ordinary skill in the art. For example, a FXN-related disorder includes, without limitation, e.g., Friedreich's ataxia (FRDA) and cancer.

In another aspect, the disclosure provides a method for reducing the growth of a cancer cell, the method comprising: (a) introducing into the cancer cell an antisense oligonucleotide described above; and (b) maintaining the cell produced in step (a) for a time sufficient to increase expression of the transcript of the FXN gene, or increase expression of the frataxin protein, thereby reducing the growth of the cancer cell.

Any suitable method for monitoring the growth of a cancer cell or plurality of cancer cells may be used. A non-limiting example includes counting the number of cells before introducing the antisense oligonucleotide of the disclosure, followed by counting the number of cells after introducing the antisense oligonucleotide of the disclosure a time sufficient to increase expression of the transcript of the FXN gene.

In another aspect, the disclosure provides a method of treating cancer comprising administering a therapeutically effective amount of the antisense oligonucleotide described above to a patient in need of such treatment.

In one aspect, the disclosure provides a method for reducing the growth of a cancer cell, the method comprising: (a) introducing into the cancer cell an antisense oligonucleotide comprising a region of complementarity to an intron of a FXN transcript; and (b) maintaining the cell produced in step (a) for a time sufficient to increase expression of the transcript of the FXN gene, or increase expression of the frataxin protein, thereby reducing the growth of the cancer cell.

In one aspect, the disclosure provides a method of treating cancer comprising administering a therapeutically effective amount of the antisense oligonucleotide comprising a region of complementarity to an intron of a FXN transcript, to a patient in need of such treatment.

In certain embodiments, the antisense oligonucleotide comprises a nucleic acid sequence with at least 90% sequence identity to the nucleic acid sequence set forth in any one of SEQ ID NOs: 13-42.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present disclosure has been described with reference to the specific embodiments thereof, it should be understood by those skilled in the art that various changes can be made and equivalents can be substituted without departing from the true spirit and scope of the disclosure. It will be readily apparent to those skilled in the art that other suitable modifications and adaptations of the methods described herein can be made using suitable equivalents without departing from the scope of the embodiments disclosed herein. In addition, many modifications can be made to adapt a particular situation, material, composition of matter, process, process step or steps, to the objective, spirit and scope of the present disclosure. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

The present disclosure is further illustrated by the following examples which should not be construed as further limiting.

Example 1—Materials and Methods

Antisense Oligonucleotides

Phosphoramidites used in this disclosure were purchased from ChemGenes. 0.1M DDTT (ChemGenes) was used as the sulfurising reagent and 0.25M BTT (AIC) as the activator. ASOs were synthesized on Dr. Oligo 48, ABI394, AKTA Oligopilot 10 or AKTA Oligopilot 100 synthesizers, according to the required scale. MOE phosphoramidites were coupled for 8 minutes. Oligonucleotides were deprotected in concentrated aqueous ammonia at 55° C. for 18 h and purified using ion-exchange chromatography (eluting with 30% acetonitrile in water containing increasing gradients of $NaClO_4$). Final purification, desalting, concentration and pH adjustment were effected by diafiltration in an Amicon centrifugal filter. All oligonucleotides were characterized by LCMS.

Cell Culture

FRDA patient derived fibroblasts (GM03816) were used in all in vitro studies. Fibroblast cells (Coriell Institute) were cultured in minimum essential medium supplemented with 10% fetal bovine serum and 1% non-essential amino acid (NEAA). All cells were grown at 37° C. in 5% CO2. Lipofectamine RNAiMAX (Invitrogen) was used to transfect siRNAs or antisense oligonucleotides following the manufacturer's recommended protocol in OptiMEM low-serum medium (Invitrogen). The oligo-lipofectamine complex remained in the full medium for 72 hours. Transfected cells were harvested 72 hours after transfection for RNA extraction and quantitative PCR (qPCR) analyses or branched DNA (bDNA) analyses.

FRDA Transgenic Mice

The FRDA mouse model YG8R was used in the in vivo studies. Briefly, the YG8R mouse model is an Fxn-knockout mouse that is hemizygous for the YG8 transgene (which carries two tandem copies of the human FXN gene with two GAA trinucleotide repeat expansions of 90-190 repeats). The YG8R mouse is described in further detail in Virmouni et al. Dis Model Mech. 2015 Mar. 8(3): 225-235.

Stereotaxic Pump Implantation and Bolus Injection of ASO in the Mouse Brain

For intracerebroventricular (ICV) injection of antisense oligonucleotide or PBS vehicle, mice were injected with a syringe with the following protocol:

1. The syringe was flushed with PBS, then loaded with 10 µL of the antisense oligonucleotide-containing solution (or 10 µL of sterile 1×PBS). A MicroSyringe Pump was set to inject 10,000 nL at 400 nL/sec. (10 µl in 25 seconds).
2. The mouse was anesthetized with 100 µL per 10 g body weight of Fentanyl/Midazolam/Dexmedetomidine (0.1/5.0/0.25 mg/kg) IP.
3. Once toe pinch reflexes ceased, the mouse was secured in a stereotaxic frame (on heat pad).
4. The injection site was disinfected with iodine and ethanol, and a small incision was made on the midline of the scalp to expose the skull.
5. The syringe injection coordinates used the bregma suture as point zero, and a bur hole was drilled on the skull; for ventricular injections of B6 mice: +0.3 AP, −1.0 ML
6. The needle was lowered to the correct depth; for ventricular injections of B6 mice: −3.0 DV
7. The brain was allowed to close around the needle for 2 minutes, then the microinjector was run; the syringe was removed 15 minutes after injection.
8. The mouse was sutured, removed from the frame, and reverse anesthesia using 0.1 mL per 10 g body weight of Flumazenil/Atipamezole (5.0/0.5 mg/kg) IP, and administered 0.1 mL per 10 g body weight of Buprenorphine (0.3 mg/kg).

Mouse Tissue Collection

1. Mice were anesthetized using 0.1 mL per 10 g body weight of Fentanyl/Midazolam/Dexmedetomidine (0.1/5.0/0.25 mg/kg) or that of Ketamine/Xylazine (100/10 mg/kg) IP.
2. Blood was collected for the blood chemistry panel.
3. Brains were removed and sectioned for 2 mm punches of hippocampus, cortex, cerebellum, cervical spinal cord, and DRG.

RNA Extraction and qPCR

Total RNA was extracted by the RNeasy Plus Mini Kit (QIAGEN, Cat No: 74136), and was reverse-transcribed using the High Capacity cDNA Reverse Transcription Kit (Applied Biosystems). qPCR was performed using SYBR Supermix (Biorad) with ~50 ng of cDNA as template. Data were normalized relative to measured HPRT levels.

bDNA Protocol

The branched DNA (bDNA) assay was performed by the QuantiGene™ Singleplex Assay Kit (Thermo Fisher Scientific, Cat No: QS0009) according to its protocol. Applied bDNA probe information is as follow: human FXN probe (Cat No: SA-6000968), human HPRT probe (Car No: SA-10030), mouse Ppib probe (Cat No: SB-10002)

Example 2—Screening of Antisense Oligonucleotides in Intron 1 of FXN

Target Sequence Selection in Intron 1 of FXN

Increased RNA/DNA hybrid (R-loop) formation in the GAA repeat region in the FXN locus is an initial event in FRDA (Groh et al. PLoS Genet. 2014 May. 10(5): e1004318). Studies have shown that antisense oligonucleotide targeting the transcripts from the GAA repeats can decrease the R-loop formation and restore FXN expression (Li et al. Nat Commun. 2016. 7:10606). Interestingly, the increased R-loop formation is not limited in the GAA-repeat region in FA (Groh et al., supra). Accordingly, the purine content of FXN intron 1 was bioinformatically analyzed to identified purine-rich sequences (FIG. 1). These purine-rich sequences can contribute to the increased R-loop formation and epigenetic silencing of FXN.

Figure 2:
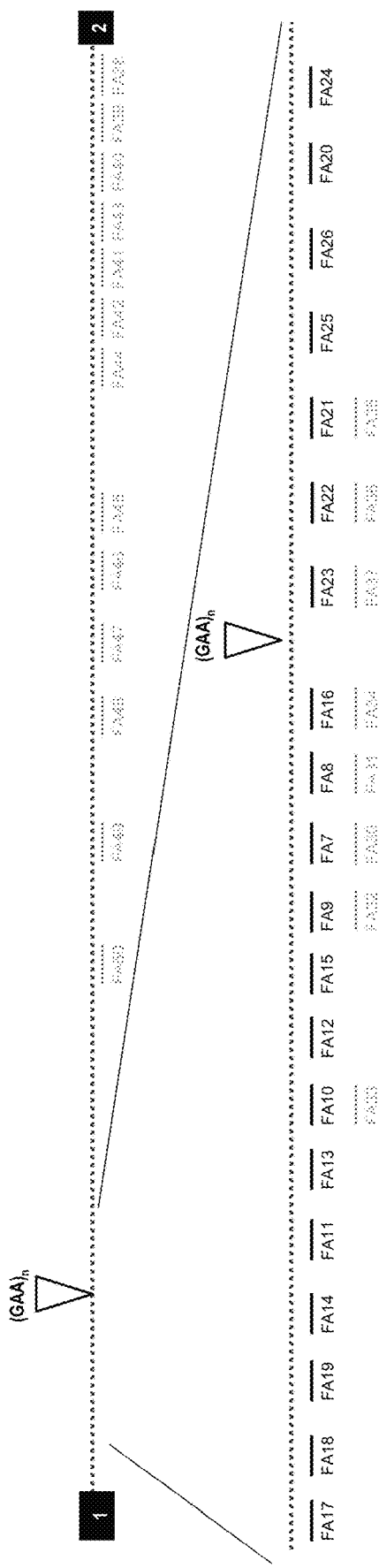
FIG. 2 depicts a schematic of FXN intron 1. Steric blocking antisense oligonucleotides are depicted in black and gapmer antisense oligonucleotides are depicted in grey.

To target FXN transcripts from these purine-rich sequences, antisense oligonucleotides were designed to target sequences upstream and downstream of the GAA repeat, but not within the repeat itself. Two types of antisense oligonucleotides were designed, steric blocking antisense oligonucleotides and gapmer antisense oligonucleotides (FIG. 2).

Testing FXN-Targeting Antisense Oligonucleotides in Cultured Cells

Figure 3:
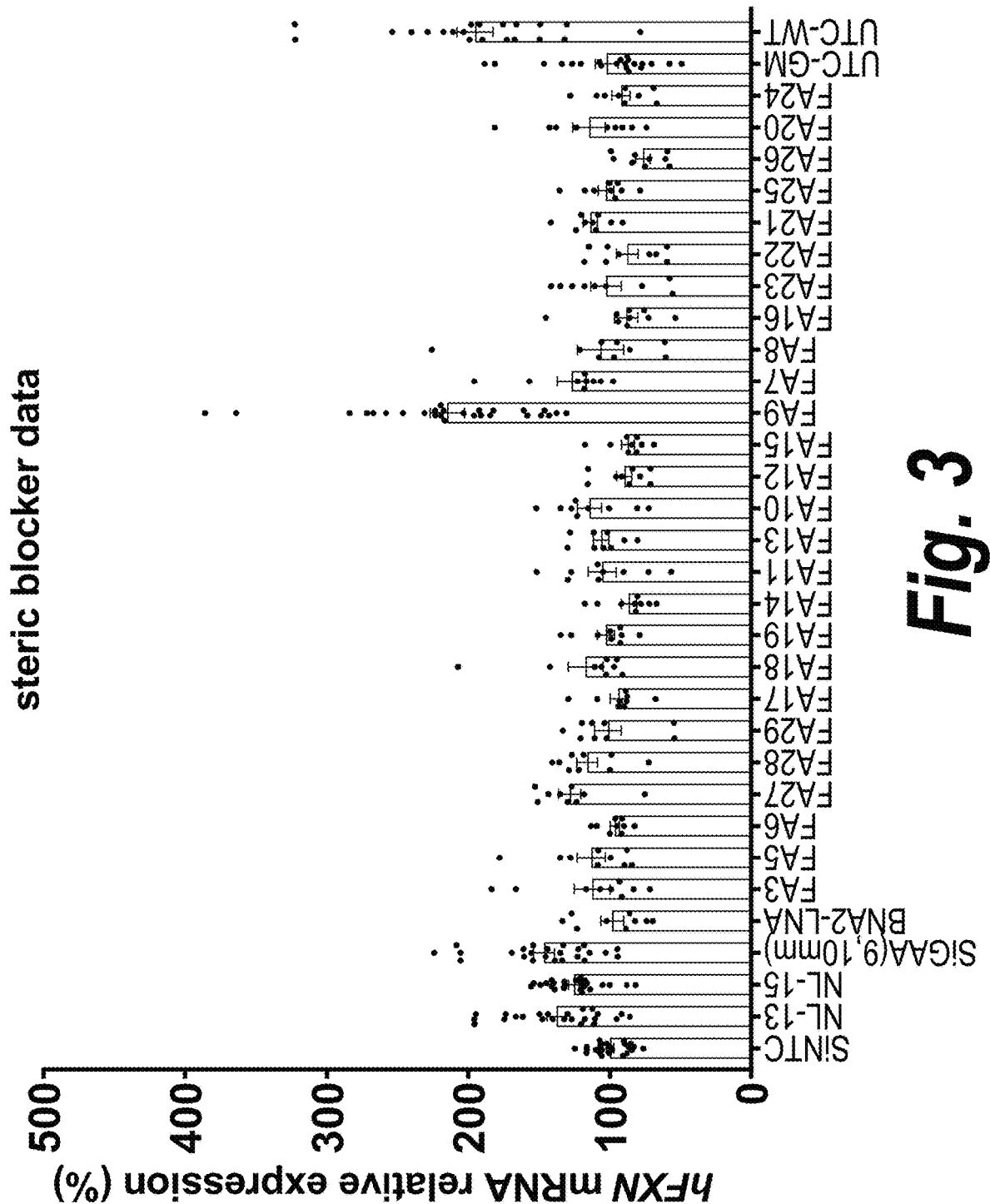
FIG. 3 depicts relative hFXN mRNA expression as measured by a bDNA assay. Steric blocking antisense oligonucleotides were used. SiNTC is a non-target siRNA negative control. SiGAA (9, 10 mm) is an siRNA targeting the GAA repeat with mismatches at position 9 and 10 in the guide strand and serves as a positive control. NL-13 and NL-15 are single-strand oligonucleotide non-target negative controls. BNA2_LNA is a LNA-containing ASO non-target negative control. UTC-GM is an untreated control of GM03816 cells (patient derived fibroblasts). UTC-WT is an untreated control of human wildtype fibroblasts.
Figure 4:
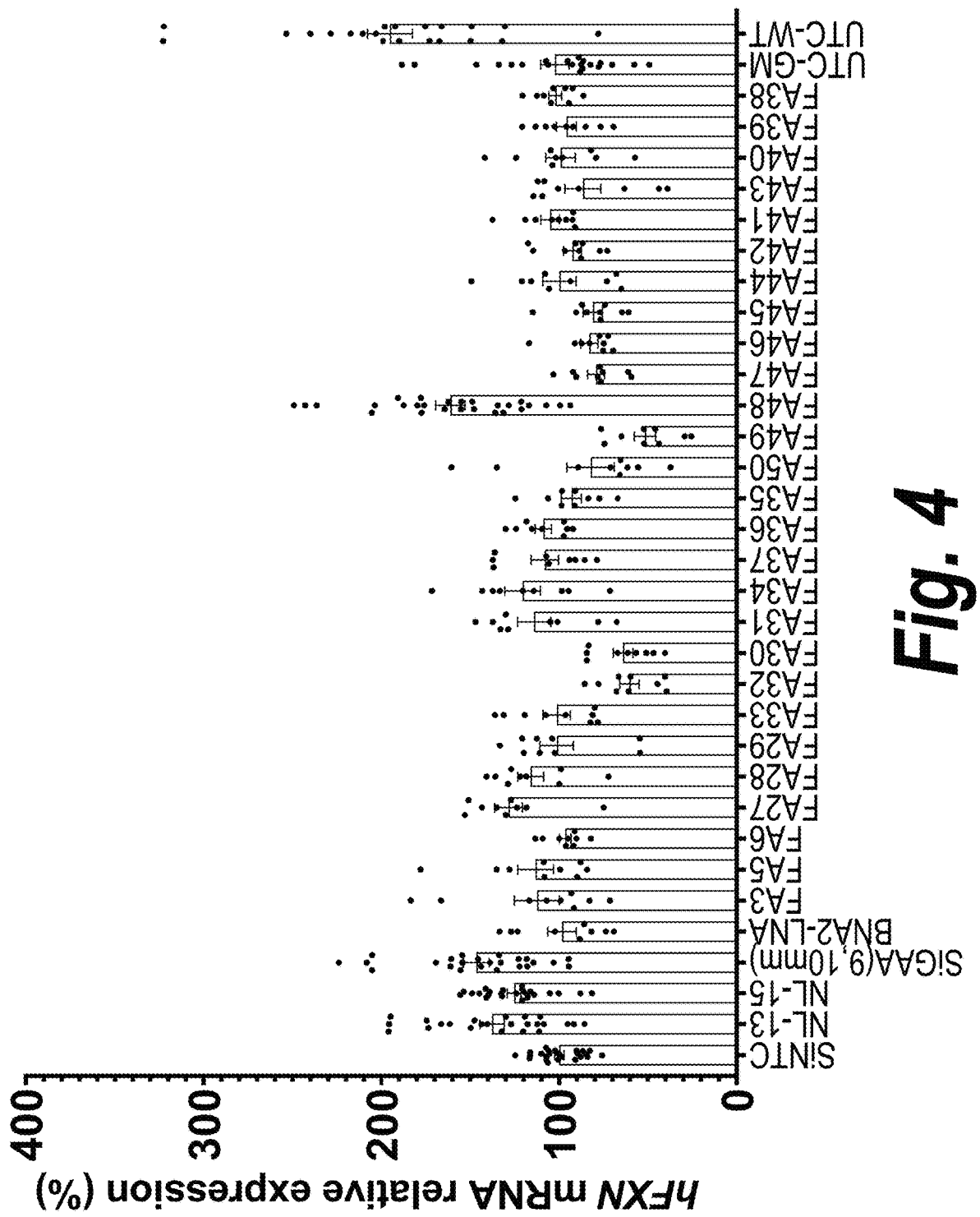
FIG. 4 depicts relative hFXN mRNA expression as measured by a bDNA assay. Gapmer antisense oligonucleotides were used. SiNTC is a non-target siRNA negative control. SiGAA (9, 10 mm) is an siRNA targeting the GAA repeat with mismatches at position 9 and 10 in the guide strand and serves as a positive control. NL-13 and NL-15 are single-strand oligonucleotide non-target negative controls. BNA2_LNA is a LNA-containing ASO non-target negative control. UTC-GM is an untreated control of GM03816 cells (patient derived fibroblasts). UTC-WT is an untreated control of human wildtype fibroblasts.

FRDA patient derived fibroblasts (GM03816) were used to evaluate the efficacy of the FXN-targeting antisense oligonucleotides designed above. FXN mRNA was measured by the Quantigene singleplex gene expression assay. The steric blocking antisense oligonucleotide designs demonstrated that antisense oligonucleotide FA9 was able to increase FXN mRNA up to and above wild type levels (FIG. 3). The gapmer antisense oligonucleotide designs demonstrated that antisense oligonucleotide FA48 was able to similarly increase FXN mRNA up to and above wild type levels (FIG. 4). The sequence of antisense oligonucleotides FA9 and FA48 are shown below in Table 2. Different chemical modification patterns than those recited in Table 2 are envisioned. For example, but in no way limiting, the steric blocking antisense oligonucleotide can comprise a mixture of different types of modifications, such as a mixture of 2'-O-(2-methoxyethyl) modifications, LNA modifications, tricyclo-DNA modifications, and DNA modifications.

TABLE 2

Antisense oligonucleotides (ASOs) used in cultured cells

| Name | Sequence (5'-3') |
| --- | --- |
| FA9 | $G_sU_sA_sC_sA_sA_sA_sC_sU_sC_sC_sG_sG_sA_sG_sA_sG_sC$ |
| FA48 | $G_sC_sA_sA_sU_sA_sC_sA_sT_sG_sG_sA_sT_sT_sG_sG_sG$ | where "$s$" represents a phosphorothioate internucleoside linkage;
"A" is an adenosine comprising a 2'-O-(2-methoxyethyl) modification;
"G" is a guanosine comprising a 2'-O-(2-methoxyethyl) modification;
"C" is a cytidine comprising a 2'-O-(2-methoxyethyl) modification;
"U" is a thymine comprising a 2'-O-(2-methoxyethyl) modification;
"A" is an adenosine comprising a 2'-deoxy modification;
"G" is a guanosine comprising a 2'-deoxy modification;
"C" is a cytidine comprising a 2'-deoxy modification; and
"T" is a thymine comprising a 2'-deoxy modification.

Example 3—Optimization of Antisense Oligonucleotides and Combinations Thereof

Figure 5A:
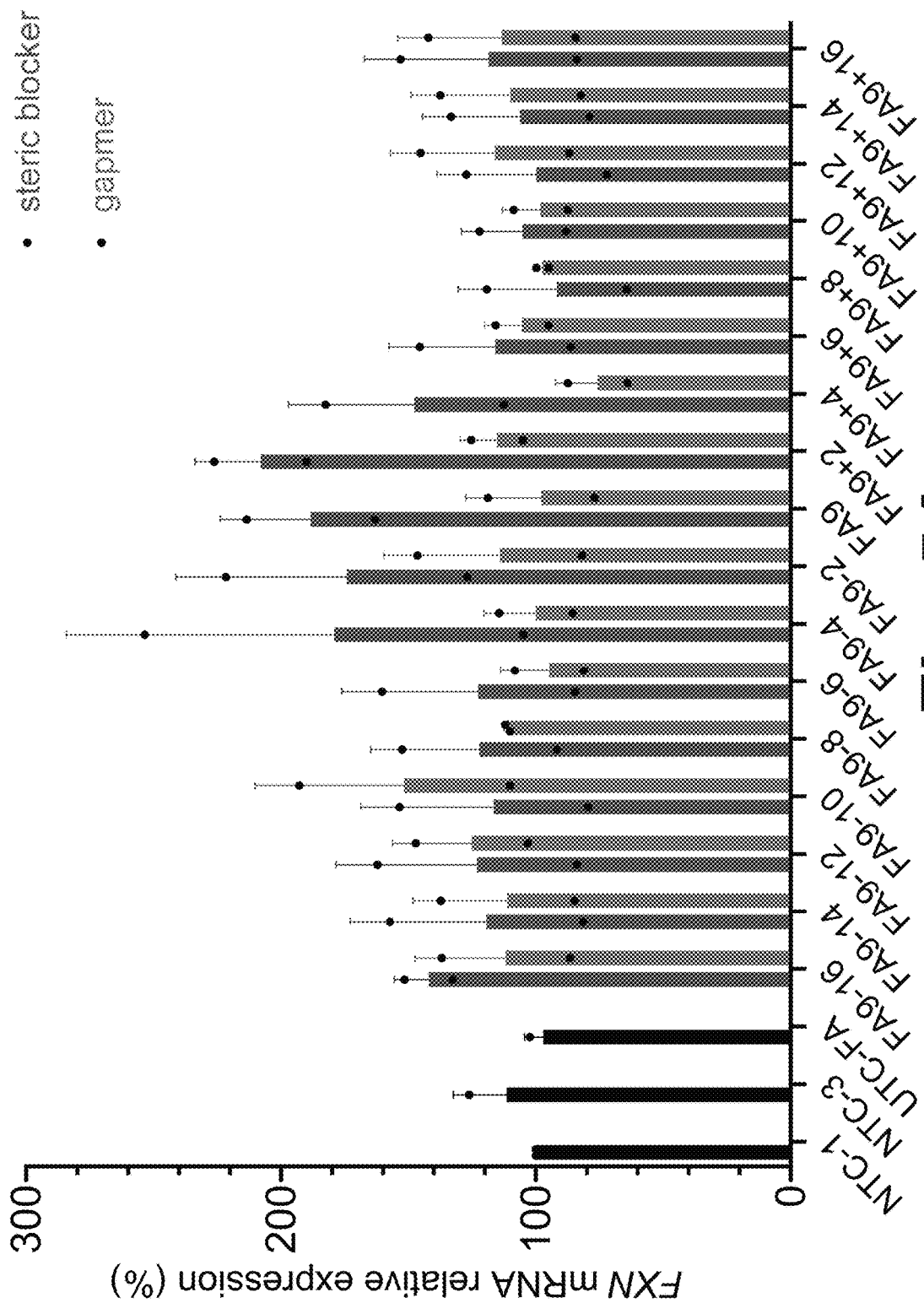
FIG. 5A-FIG. 5B depict relative hFXN mRNA expression as measured by a bDNA assay. The antisense oligonucleotide FA9 was used in a steric blocking format and a gapmer format. A 2-nucleotide oligonucleotide walk to the left and right of the FA9 sequence was also performed. For each set of data bars (i.e., FA9-16, FA9-14, etc.), the left bar represents the steric blocking format and the right bar represents the gapmer format. NTC-1 and NTC-3 are steric blockers serving as non-target controls. UTC-FA is an untreated control of GM03816 cells (patient derived fibroblasts) (FIG. 5A). Oligonucleotides in the group of FA9 micro-walk and FA9 long oligo groups represent variations on the parent FA9 sequence. 11627 and 11628 represent FA9+2 with LNA modifications incorporated. 11629 and 11630 represent FA9+2 with 1 nucleotide mismatch. MG2 is an ASO gapmer targeting human MALAT1 and the rightmost two bars demonstrate the expression of MALAT1; these two samples were included as a positive control for transfection efficiency. siNTC, NL-15 and mNTC-1 are steric blockers serving as non-target controls. UTC is an untreated control of GM03816 cells (patient derived fibroblasts) (FIG. 5B).
Figure 5B:
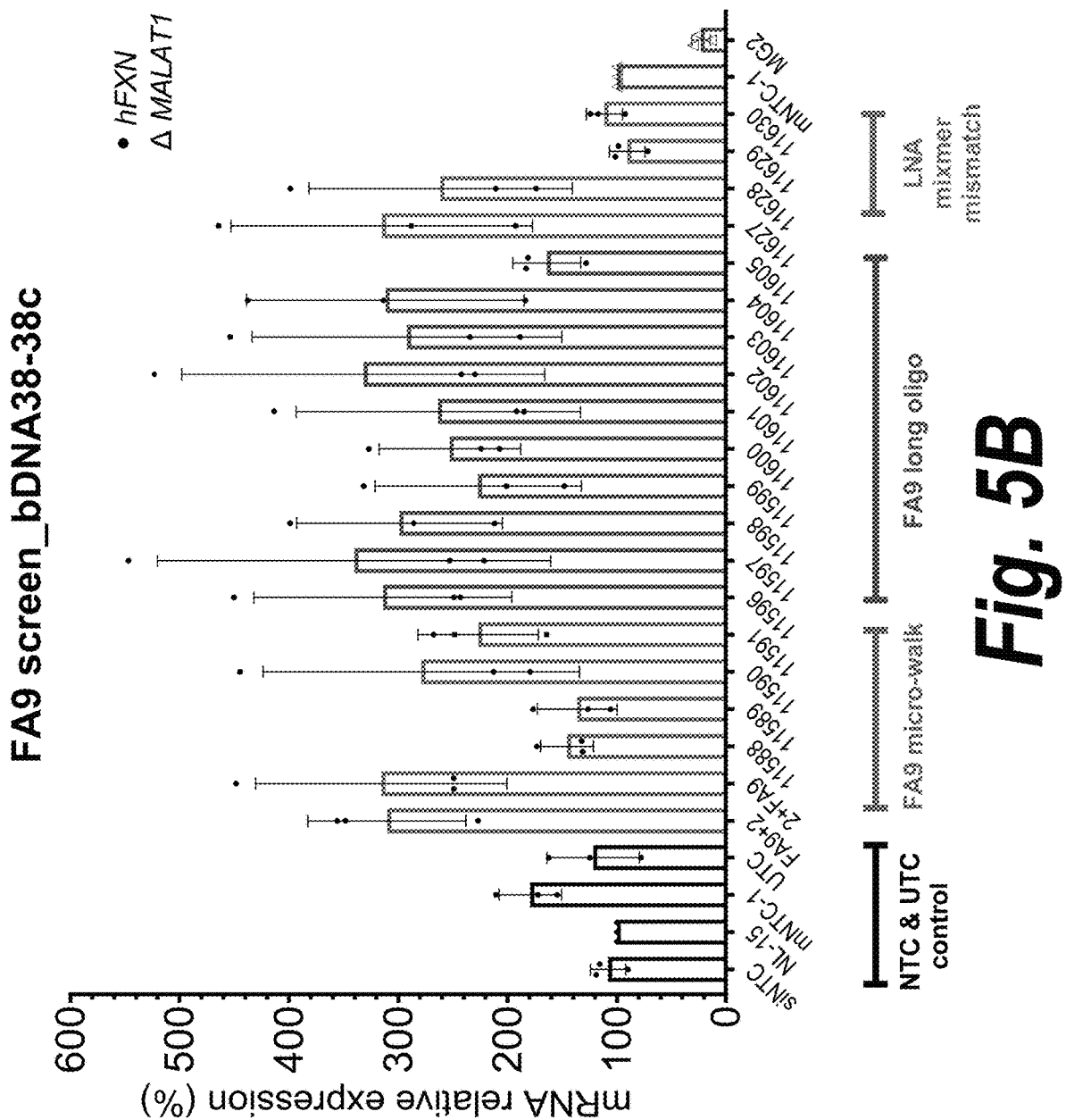
Figure 6B:
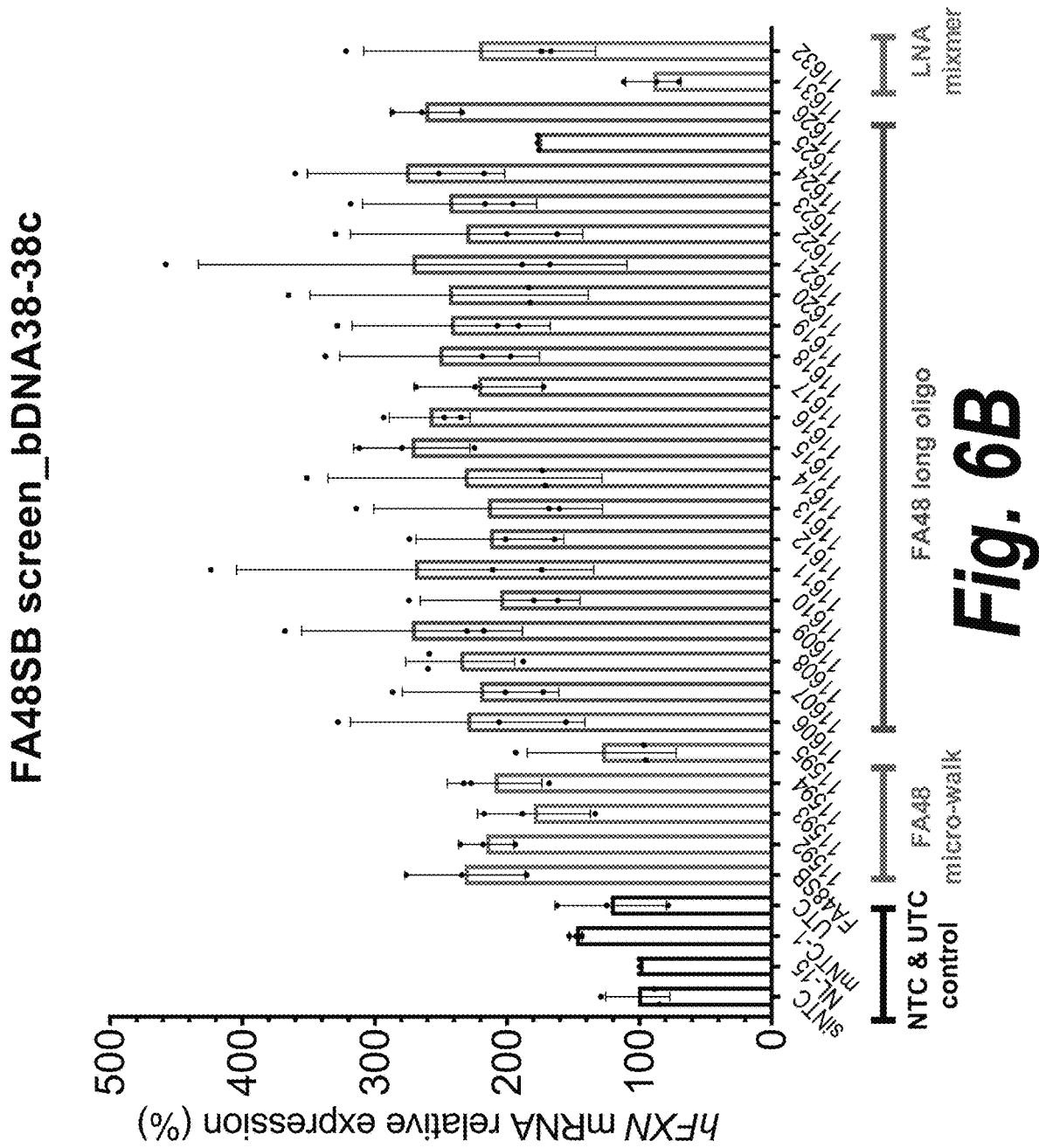

Having identified antisense oligonucleotides FA9 and FA48 as being efficacious, the FXN transcript target site for each antisense oligonucleotide was interrogated further. An oligonucleotide walk experiment was performed, where antisense oligonucleotides were designed to bind the FXN transcript within 16 nucleotides upstream and downstream of the FA9 and FA48 target sites, with 2-nucleotide increments. Each new antisense oligonucleotide was used in the steric blocking format and gapmer format described in Example 2. As demonstrated in FIG. 5A and FIG. 6A, shifting the target binding site to the left and right (upstream and downstream) of the FA9 and FA48 target sites retain a degree of the desired activity to increase FXN mRNA expression. Furthermore, it was surprisingly discovered that the FA48 antisense oligonucleotide was able to increase FXN mRNA expression in both the steric blocking and gapmer format. The two formats employ different mechanisms of action. The gapmer leads to RNase H-mediated cleavage of the target mRNA, while the steric blocker leads to a non-cleavage based interaction with the target mRNA. This data suggests that the FA48 antisense oligonucleotide target site can be bound with different oligonucleotide formats and still obtain the desired increase in FXN mRNA expression. As demonstrated in FIG. 5B and FIG. 6B, the micro-walk data represents variations of the FA9 and F48 oligonucleotides, each oligonucleotide in the micro-walk corresponding to moving the oligonucleotide one or two bases upstream and downstream of the target site. The long oligo group represents variations of FA9 and FA48 by increasing the total length of the oligonucleotide to greater than 18 nucleotides in length. 11627 and 11628 represent FA9+2 with LNA modifications incorporated. 11629 and 11630 represent FA9+2 with a 1 nucleotide mismatch.

The results of the oligonucleotide walk experiment reveal additional variations on the FA9 and FA48 sequences that are capable of increasing FXN mRNA expression. These sequences are recited below in Table 3. The sequences may be modified in any manner described above, including in a gapmer or steric blocking format.

TABLE 3

Antisense oligonucleotide sequences tested

| Name | Sequence (5'-3') |
| --- | --- |
| FA9 | GUACAAACUCCGGAGAGC (SEQ ID NO: 13) |
| FA9 extended 1 | AAGUACAAACUCCGGAGAGC (SEQ ID NO: 16) |
| FA9 extended 2 | GUACAAACUCCGGAGAGCAA (SEQ ID NO: 17) |
| FA9 extended 3 | AGUACAAACUCCGGAGAGCA (SEQ ID NO: 18) |
| FA9-2 | ACAAACUCCGGAGAGCAA (SEQ ID NO: 19) |
| FA9-4 | AAACUCCGGAGAGCAACA (SEQ ID NO: 20) |
| FA9-6 | ACUCCGGAGAGCAACACA (SEQ ID NO: 21) |
| FA9-8 | UCCGGAGAGCAACACAAA (SEQ ID NO: 22) |
| FA9-10 | CGGAGAGCAACACAAAUA (SEQ ID NO: 23) |
| FA9-12 | GAGAGCAACACAAAUAUG (SEQ ID NO: 24) |

TABLE 3-continued

Antisense oligonucleotide sequences tested

| Name | Sequence (5'-3') |
| --- | --- |
| FA9-14 | GAGCAACACAAAUAUGGC (SEQ ID NO: 25) |
| FA9-16 | GCAACACAAAUAUGGCUU (SEQ ID NO: 26) |
| FA9+2 | AAGUACAAACUCCGGAGA (SEQ ID NO: 27) |
| FA9+4 | UAAAGUACAAACUCCGGA (SEQ ID NO: 28) |
| FA9+6 | CCUAAAGUACAAACUCCG (SEQ ID NO: 29) |
| FA9+8 | AGCCUAAAGUACAAACUC (SEQ ID NO: 30) |
| FA9+10 | CAAGCCUAAAGUACAAAC (SEQ ID NO: 31) |
| FA9+12 | UUCAAGCCUAAAGUACAA (SEQ ID NO: 32) |
| FA9+14 | AGUUCAAGCCUAAAGUAC (SEQ ID NO: 33) |
| FA9+16 | GAAGUUCAAGCCUAAAGU (SEQ ID NO: 34) |
| FA48 | GCAAUACAUGGAUUGGGG (SEQ ID NO: 14) |
| FA48-2 | AAUACAUGGAUUGGGGGA (SEQ ID NO: 35) |
| FA48-4 | UACAUGGAUUGGGGGAGA (SEQ ID NO: 36) |
| FA48-6 | CAUGGAUUGGGGGAGAUA (SEQ ID NO: 37) |
| FA48-8 | TGGAUUGGGGGAGAUACA (SEQ ID NO: 38) |
| FA48-10 | GAUUGGGGGAGAUACAGA (SEQ ID NO: 39) |
| FA48-12 | TTGGGGGAGAUACAGAGG (SEQ ID NO: 40) |
| FA48-14 | GGGGGAGAUACAGAGGAG (SEQ ID NO: 41) |
| FA48-16 | GGGAGAUACAGAGGAGGU (SEQ ID NO: 42) |

Figure 7C:
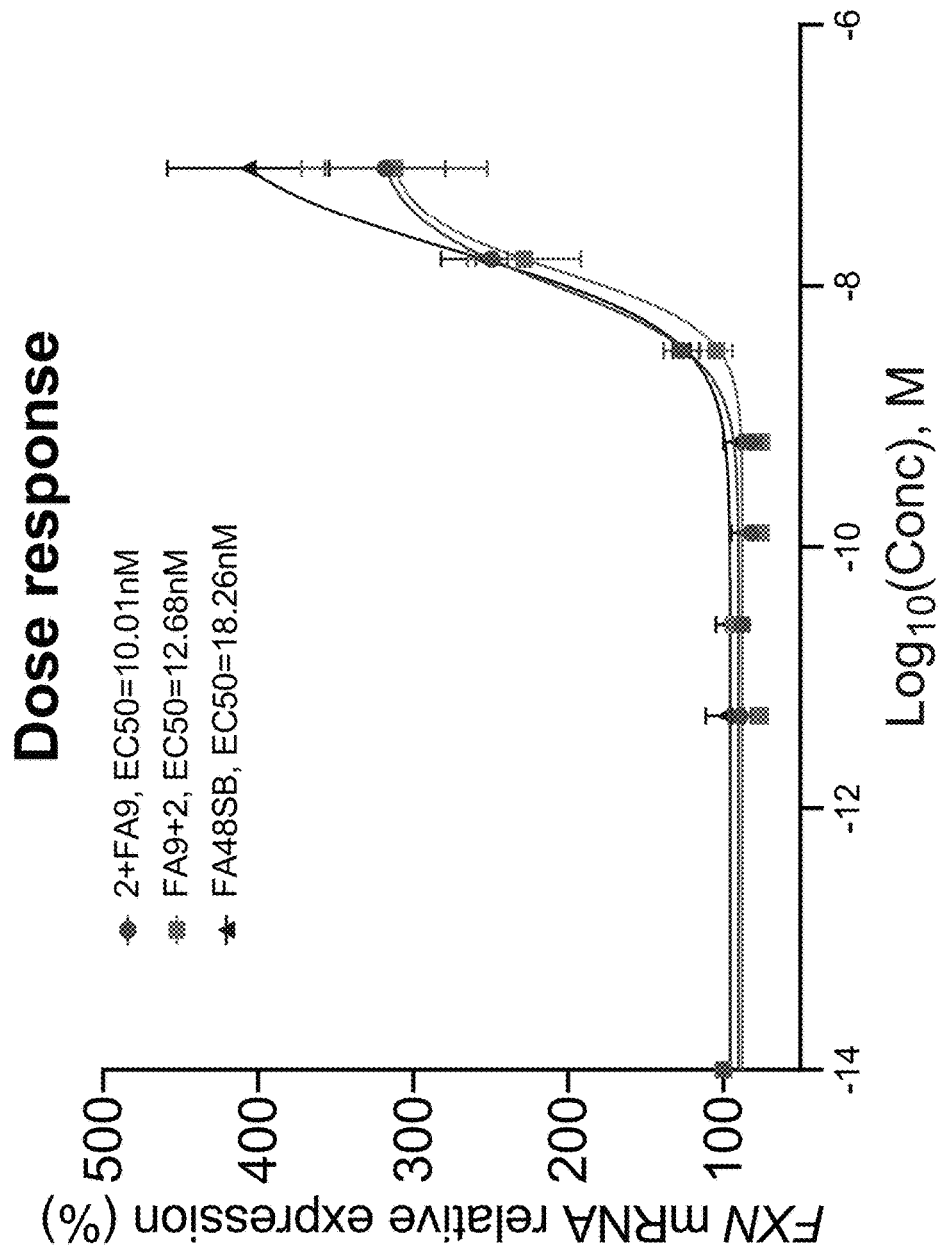
Figure 8C:
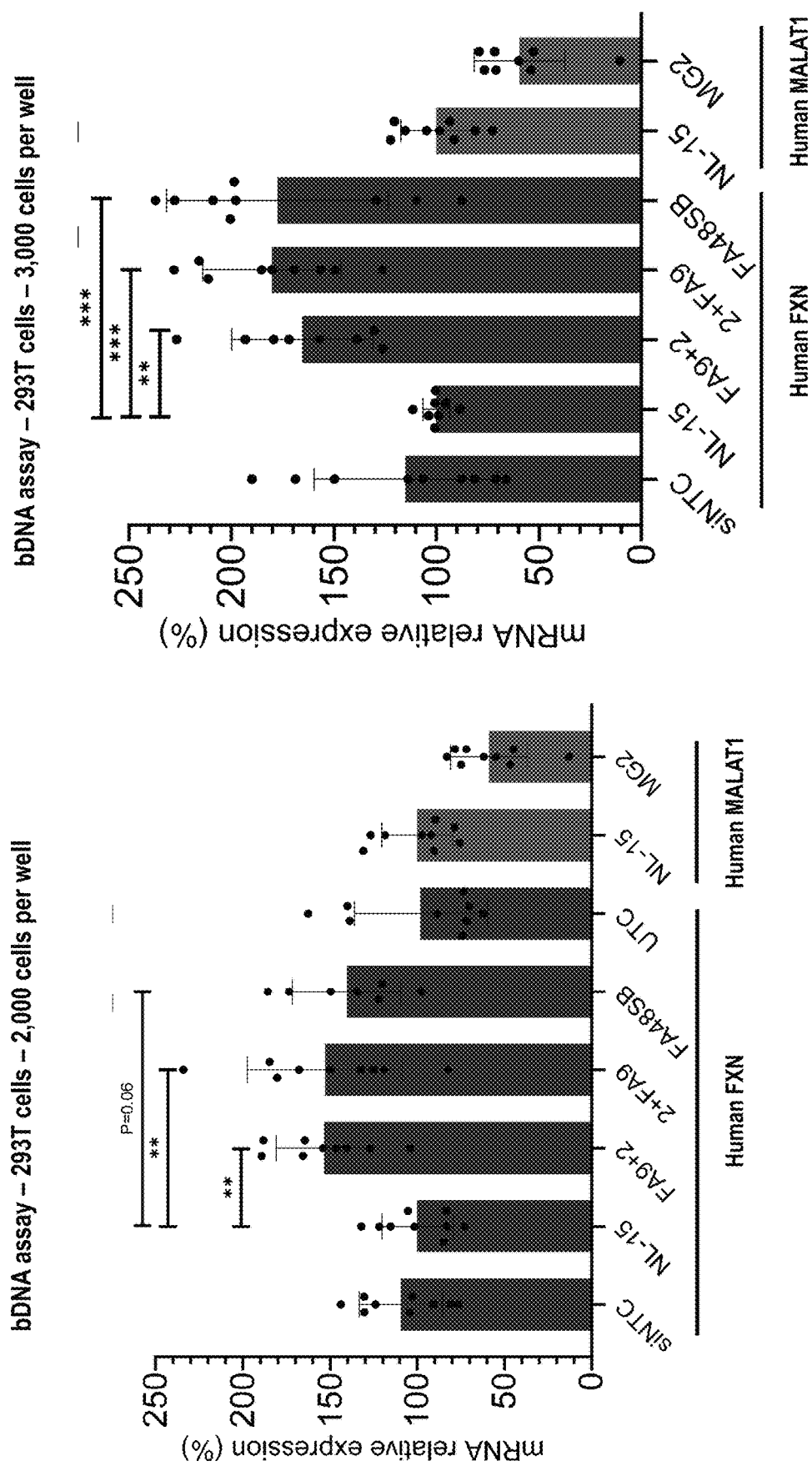
Figure 8D:
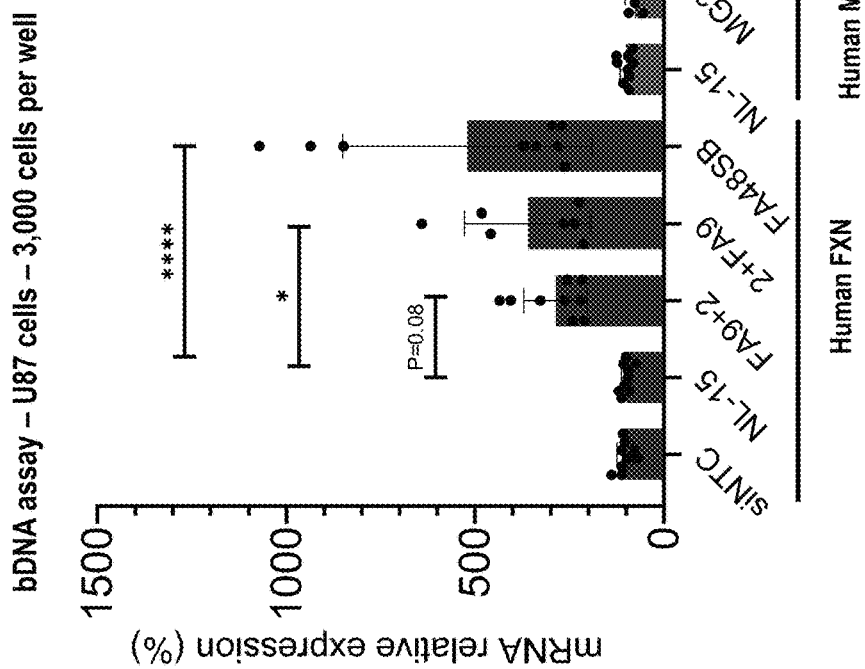
Figure 8D:
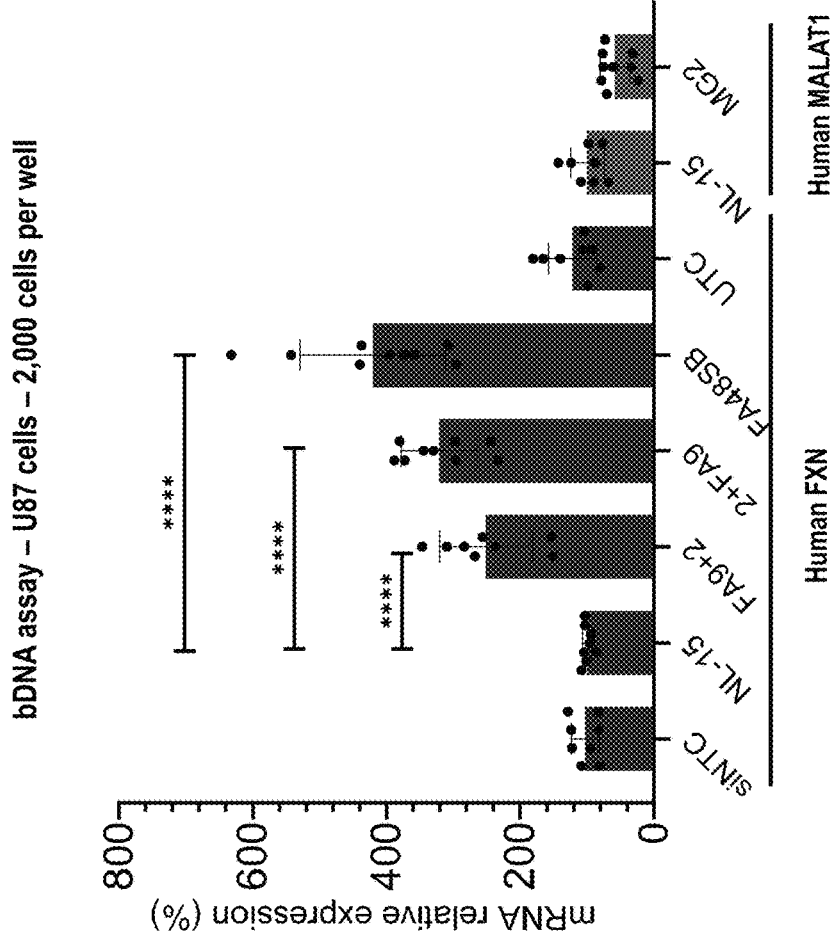

In addition to designing alternative antisense oligonucleotides, the antisense oligonucleotides FA9 and FA48 were used in combination. As shown in FIG. 7A and FIG. 7B, the combination led to an increase in FXN mRNA expression that reached or exceeded the expression level of each antisense oligonucleotide alone. A dose response curve was also generated using the FA9 antisense oligonucleotide shifted two nucleotides to the left and right, as well as FA48SB. Each antisense oligonucleotide demonstrated an ability to increase in FXN mRNA expression at multiple doses (FIG. 7C).

Example 4—FXN Antisense Oligonucleotides for Cancer Cell Growth Reduction

Figure 9A:
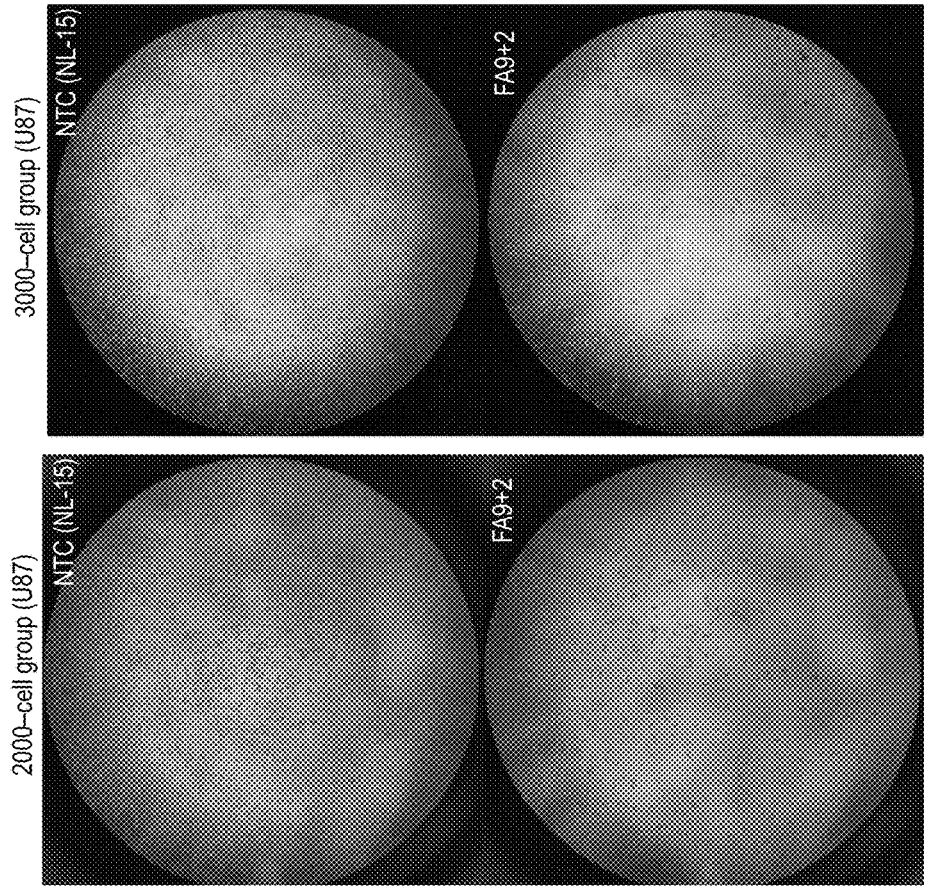
FIG. 9A-FIG. 9C depict evidence that FXN activation can reduce the growth of cancer cells in culture.
Figure 9C:
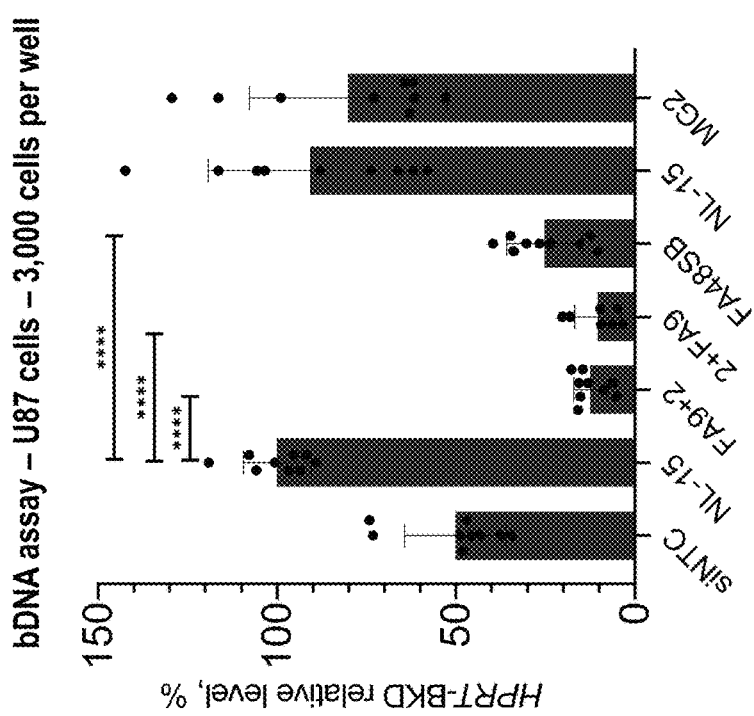
Figure 9B:
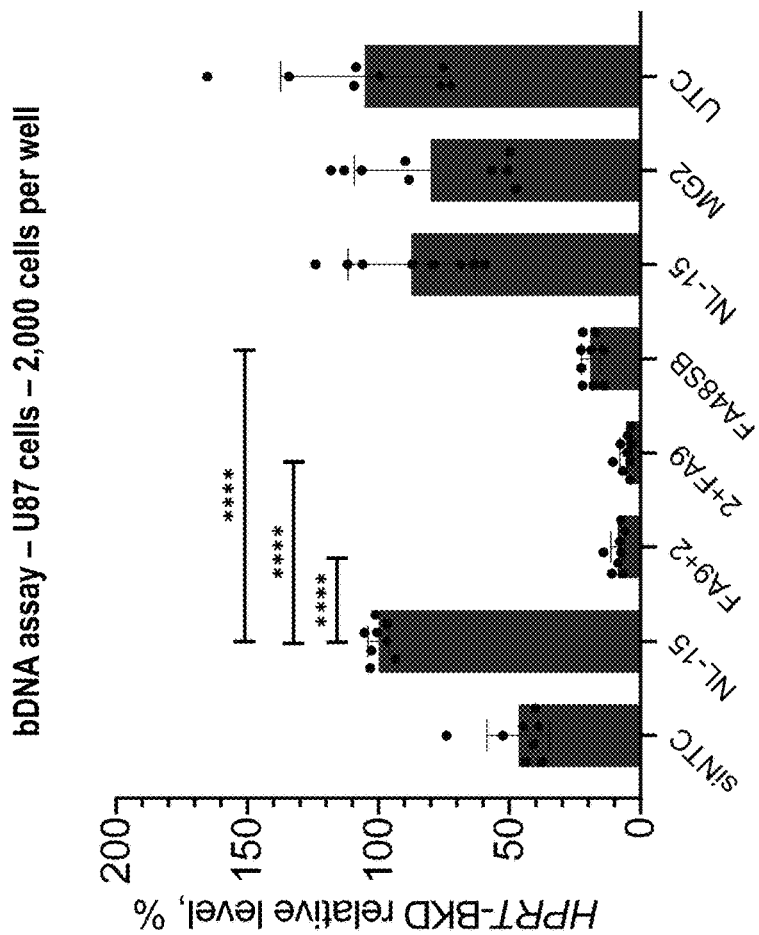

It has been previously demonstrated that FXN overexpression in a mouse cancer model and human cancer cells can decrease cancer cell growth (Schulz et al. J. Biol. Chem. 281(2): 977-981. 2006). The FXN-targeting antisense oligonucleotides of the disclosure were tested in the Human primary glioblastoma cell line, U87. Cells were seeded at 2000 cells per well or 3000 cells per well at the beginning of treatment. Cells were then incubated with select FXN-targeting antisense oligonucleotides for 72 hours and the plates were imaged and quantified. Quantification was performed by measuring relative HPRT-BKD values of the indicated treatments normalized by the NL-15 control group. SiNTC and NL-15 served as non-target controls. The antisense oligonucleotide MG2 is an ASO gapmer targeting human MALAT1 as a positive control for transfection efficiency. As shown in FIG. 9A-FIG. 9C, the FXN-targeting antisense oligonucleotides slowed the growth of the U87 cancer cell line.

What is claimed is:

1. An antisense oligonucleotide comprising a 3' end, a 5' end, a mixture of modified nucleotides, and a region of complementarity to an intron of a frataxin (FXN) pre-mRNA transcript,
   wherein the mixture of modified nucleotides comprises four consecutive 2'-O-methoxyethyl modified ribonucleotides located at the 3' end of the antisense oligonucleotide, five consecutive 2'-O-methoxyethyl modified ribonucleotides located at the 5' end of the antisense oligonucleotide, and at least one 2'-deoxy modified nucleotide, and
   wherein the antisense oligonucleotide is between 10 nucleotides to 30 nucleotides in length
   wherein the region of complementarity is at least 70% complementary to a target segment of SEQ ID NO: 6 or SEQ ID NO: 11.

2. An antisense oligonucleotide comprising a 3' end, a 5' end, a mixture of modified nucleotides, and a region of complementarity to an intron of a frataxin (FXN) pre-mRNA transcript,
   wherein the mixture of modified nucleotides comprises four consecutive 2'-O-methoxyethyl modified ribonucleotides located at the 3' end of the antisense oligonucleotide, five consecutive 2'-O-methoxyethyl modified ribonucleotides located at the 5' end of the antisense oligonucleotide, and at least one 2'-deoxy modified nucleotide,
   wherein the antisense oligonucleotide is between 10 nucleotides to 30 nucleotides in length wherein the region of complementarity is at least 70% complementary to a target segment of SEQ ID NO: 6 or SEQ ID NO: 10, and
   wherein the antisense oligonucleotide is fully complementary to the target segment of SEQ ID NO: 6 or SEQ ID NO:10.

3. The antisense oligonucleotide of claim 2, wherein the mixture of modified nucleotides comprises a modification of a phosphate group.

4. An antisense oligonucleotide comprising:
   a region of complementarity to an intron of a FXN pre-mRNA transcript; and
   the formula:

A-B-C, wherein:

A comprises about 5 consecutive 2'-O-(2-methoxyethyl) (MOE) modified nucleotides, B comprises about 9 consecutive DNA-like nucleotides, and C comprises about 4 consecutive 2'-O-(2-methoxyethyl) (MOE) modified nucleotides; wherein the region of complementarity is at least 70% complementary to a target segment of 10 nucleotides to 30 nucleotides of SEQ ID NO: 6 or SEQ ID NO: 11.

5. An antisense oligonucleotide comprising a 3' end, a 5' end, a mixture of modified nucleotides, and a region of complementarity to an intron of a frataxin (FXN) pre-mRNA transcript,
  wherein the mixture of modified nucleotides comprises four consecutive 2'-O-methoxyethyl modified ribonucleotides located at the 3' end of the antisense oligonucleotide, five consecutive 2'-O-methoxyethyl modified ribonucleotides located at the 5' end of the antisense oligonucleotide, and at least one 2'-deoxy modified nucleotide,
  wherein the antisense oligonucleotide is between 10 nucleotides to 30 nucleotides in length wherein the region of complementarity is at least 70% complementary to a target segment of SEQ ID NO: 6 or SEQ ID NO: 10, and
  wherein the antisense oligonucleotide comprises a nucleic acid sequence with at least 90% sequence identity to the nucleic acid sequence set forth in any one of SEQ ID NOs: 13, 14, or 15 (SEQ ID NO: 13-GUACAAACUCCGGAGAGC), (SEQ ID NO: 14-GCAAUACATGGAUUGGGG), (SEQ ID NO: 15-GCAAUACAUGGAUUGGGG).

6. An antisense oligonucleotide comprising:
  a region of complementarity to an intron of a FXN pre-mRNA transcript; and
  a sequence modification pattern of:
  X̲sX̲sX̲sX̲sX̲sXsXsXsXsXsXsXsXsXsX̲sX̲sX̲sX̲,
    wherein
  s represents a phosphorothioate internucleoside linkage;
  X̲ comprises an adenosine, a guanosine, a cytidine, a thymine, or a uracil, wherein X comprises a 2'-O-(2-methoxyethyl) modification; and
  X comprises an adenosine, a guanosine, a cytidine, a thymine, or a uracil, wherein X comprises a 2'-deoxy modification;
    wherein the region of complementarity is at least 70% complementary to a target segment of 10 nucleotides to 18 nucleotides of SEQ ID NO: 6 or SEQ ID NO: 11.

7. An antisense oligonucleotide comprising the sequence:
  G̲sC̲sA̲sA̲sU̲sAsCsAsTsGsGsAsTsTsG̲sG̲sG̲sG̲ (SEQ ID NO: 14), wherein
  s represents a phosphorothioate internucleoside linkage;
  A̲ comprises an adenosine comprising a 2'-O-(2-methoxyethyl) modification;
  G̲ comprises a guanosine comprising a 2'-O-(2-methoxyethyl) modification;
  C̲ comprises a cytidine comprising a 2'-O-(2-methoxyethyl) modification;
  U̲ comprises a thymine comprising a 2'-O-(2-methoxyethyl) modification;
  A comprises an adenosine comprising a 2'-deoxy modification;
  G comprises a guanosine comprising a 2'-deoxy modification;
  C comprises a cytidine comprising a 2'-deoxy modification; and
  T comprises a thymine comprising a 2'-deoxy modification.

8. The antisense oligonucleotide of claim 1, wherein the antisense oligonucleotide is conjugated to a ligand.

9. The antisense oligonucleotide of claim 3, wherein each modification of the phosphate group comprises a phosphorothioate, a phosphonoacetate (PACE), a thiophosphonoacetate (thioPACE), an amide, a triazole, a phosphonate, a phosphotriester, or a combination thereof.

10. The antisense oligonucleotide of claim 3, wherein the modification of the phosphate group comprises a phosphorothioate or every nucleotide of the antisense oligonucleotide comprises a phosphorothioate.

11. The antisense oligonucleotide of claim 3, wherein each modification of the nucleobase comprises a 2-thiouridine, a 4-thiouridine, a $N^6$-methyladenosine, a pseudouridine, a 2,6-diaminopurine, inosine, a thymidine, a 5-methylcytosine, a 5-substituted pyrimidine, an isoguanine, an isocytosine, a halogenated aromatic group, or a combination thereof.

12. The antisense oligonucleotide of claim 6, wherein each cytosine comprises a 5-methylcytosine.

13. The antisense oligonucleotide of claim 8, wherein: the ligand directs uptake in at least on of skeletal muscle, cardiac muscle, and pancreatic beta cells; the ligand comprises at least one of a carbohydrate, a phospholipid, an antibody, a peptide, and a hydrophobic moiety; or a combination thereof.

14. The antisense oligonucleotide of claim 11, wherein the modification of the nucleobase group comprises a 5-methylcytosine modification.

15. An antisense oligonucleotide comprising a 3' end, a 5' end, a mixture of modified nucleotides, and a region of complementarity to an intron of a frataxin (FXN) pre-mRNA transcript,
  wherein the mixture of modified nucleotides comprises four consecutive 2'-O-methoxyethyl modified ribonucleotides located at the 3' end of the antisense oligonucleotide, five consecutive 2'-O-methoxyethyl modified ribonucleotides located at the 5' end of the antisense oligonucleotide, and at least one 2'-deoxy modified nucleotide,
  wherein the antisense oligonucleotide is between 10 nucleotides to 30 nucleotides in length wherein the region of complementarity is at least 70% complementary to a target segment of SEQ ID NO: 6 or SEQ ID NO:10, and
  wherein the region of complementarity is at least 70% complementary to a target segment of 10 nucleotides to 20 nucleotides of SEQ ID NO: 7 or SEQ ID NO: 11.

16. The antisense oligonucleotide of claim 1, wherein the mixture of modified nucleotides comprises nine consecutive 2'-deoxy modified nucleotides.

17. The antisense oligonucleotide of claim 15, wherein the modified nucleotides consist in four consecutive 2'-O-methoxyethyl modified ribonucleotides located at the 3' end of the antisense oligonucleotide, five consecutive 2'-O-methoxyethyl modified ribonucleotides located at the 5' end of the antisense oligonucleotide, and nine consecutive 2'-deoxy modified nucleotides.

18. The antisense oligonucleotide of claim 16, wherein the antisense oligonucleotide is 18 nucleotides in length.

* * * * *